(12) United States Patent  
Kim et al.

(10) Patent No.: US 10,087,145 B2  
(45) Date of Patent: Oct. 2, 2018

(54) CONDENSED CYCLIC COMPOUND AND ORGANIC LIGHT-EMITTING DEVICE COMPRISING THE SAME

(71) Applicants: SAMSUNG DISPLAY CO., LTD., Yongin, Gyeonggi-Do (KR); Research & Business Foundation SUNGKYUNKWAN UNIVERSITY, Suwon, Gyeonggi-do (KR)

(72) Inventors: Myeongsuk Kim, Yongin (KR); Sungwook Kim, Yongin (KR); Jinsoo Hwang, Yongin (KR); Seungsoo Yoon, Suwon (KR)

(73) Assignees: SAMSUNG DISPLAY CO., LTD., Yongin, Gyeonggi-do (KR); Research & Business Foundation SUNGKYUNKWAN UNIVERSITY, Suwon, Gyeonggi-do (KR)

( * ) Notice: Subject to any disclaimer, the term of this patent is extended or adjusted under 35 U.S.C. 154(b) by 368 days.

(21) Appl. No.: 14/701,088

(22) Filed: Apr. 30, 2015

(65) Prior Publication Data

US 2015/0318490 A1    Nov. 5, 2015

(30) Foreign Application Priority Data

May 2, 2014    (KR) .......................... 10-2014-0053610  
Apr. 30, 2015    (KR) .......................... 10-2015-0061881

(51) Int. Cl.
| | | |
|---|---|---|
| *H01L 51/00* | (2006.01) | |
| *C07D 221/18* | (2006.01) | |
| *C09K 11/06* | (2006.01) | |
| *C07D 471/04* | (2006.01) | |

(Continued)

(52) U.S. Cl.  
CPC ......... *C07D 221/18* (2013.01); *C07D 471/04* (2013.01); *C07D 471/14* (2013.01);  
(Continued)

(58) Field of Classification Search  
CPC . C07D 221/18; C07D 471/04; H01L 51/0052; H01L 51/0072; C09K 11/06  
(Continued)

(56) References Cited

U.S. PATENT DOCUMENTS 8,993,128 B2 * 3/2015 Lee ...................... C07D 401/14  
428/690  
2006/0251920 A1    11/2006 Azia et al.  
(Continued)

FOREIGN PATENT DOCUMENTS

KR    10-2006-0115663 A    11/2006  
KR    10-2011-0109060 A    10/2010  
(Continued)

*Primary Examiner* — Michael M Dollinger  
(74) *Attorney, Agent, or Firm* — Lee & Morse, P.C.

(57) ABSTRACT

A condensed cyclic compound represented by Formula 1 and an organic light-emitting device including the condensed cyclic compound are provided;

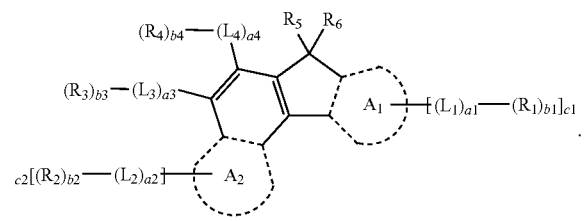

18 Claims, 1 Drawing Sheet

(51) Int. Cl.
*C07D 471/14* (2006.01)
*H01L 51/50* (2006.01)

(52) U.S. Cl.
CPC .......... *C09K 11/06* (2013.01); *H01L 51/0052* (2013.01); *H01L 51/0072* (2013.01); *C09K 2211/1007* (2013.01); *C09K 2211/1011* (2013.01); *C09K 2211/1029* (2013.01); *H01L 51/006* (2013.01); *H01L 51/0054* (2013.01); *H01L 51/5056* (2013.01); *H01L 51/5072* (2013.01)

(58) Field of Classification Search
USPC .......................................................... 428/690
See application file for complete search history.

(56) References Cited

U.S. PATENT DOCUMENTS

| 2012/0091885 | A1 | 4/2012 | Kim et al. |
| 2014/0131664 | A1* | 5/2014 | Yen ........................ C07C 13/62 257/40 |
| 2014/0249308 | A1* | 9/2014 | Parham ................ C07D 471/06 544/215 |

FOREIGN PATENT DOCUMENTS

| KR | 10-2010-0002156 A | | 1/2011 | |
| KR | 10-2011-0008892 A | | 1/2011 | |
| KR | 2013106255 A | * | 9/2013 | ........... C07D 209/82 |

* cited by examiner

10

| 190 |
| 150 |
| 110 |

CONDENSED CYCLIC COMPOUND AND ORGANIC LIGHT-EMITTING DEVICE COMPRISING THE SAME

CROSS-REFERENCE TO RELATED APPLICATIONS

Korean Patent Application No. 10-2014-0053610, filed on May 2, 2014, and Korean Patent Application No. 10-2015-0061881, filed on Apr. 30, 2015, in the Korean Intellectual Property Office, and entitled: "Condensed Cyclic Compound and Organic Light-Emitting Device Comprising the Same," are incorporated by reference herein in their entirety.

BACKGROUND

1. Field

Embodiments relate to a condensed cyclic compound and an organic light-emitting device including the same.

2. Description of the Related Art

Organic light-emitting devices (OLEDs) are self-emitting devices that have advantages such as wide viewing angles, excellent contrast, quick response, high brightness, excellent driving voltage characteristics, and can provide multicolored images.

An organic light-emitting device may have a structure in which a first electrode, a hole transport region, an emission layer, an electron transport region, and a second electrode are sequentially disposed on a substrate in this order. Holes injected from the first electrode move to the emission layer via the hole transport region, while electrons injected from the second electrode move to the emission layer via the electron transport region. Carriers such as the holes and electrons recombine in the emission layer to generate excitons. When the excitons drop from an excited state to a ground state, light is emitted.

SUMMARY

Embodiments are directed to a condensed cyclic compound represented by Formula 1:

<Formula 1>

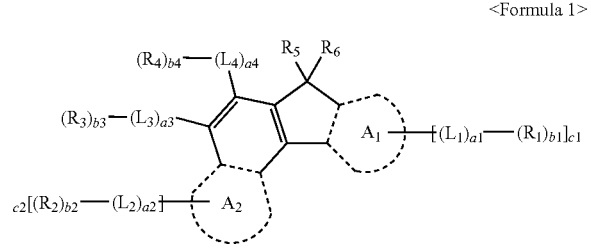

wherein, in Formula 1, $A_1$ ring is a $C_2$-$C_{20}$ heterocyclic group including at least one N as a ring member atom, and $A_2$ ring is a $C_6$-$C_{20}$ cyclic group, or a $C_2$-$C_{20}$ heterocyclic group including at least one N as a ring member atom, wherein $A_2$ ring is not a benzene when $A_1$ ring is a pyridine, $L_1$ to $L_4$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a4 are each independently selected from 0, 1, 2, and 3, $R_1$ to $R_6$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), b1 to b4 are each independently an integer selected from 0 to 3, c1 and c2 are each independently an integer selected from 0 to 10, and at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted a divalent non-aromatic condensed polycyclic group, the substituted a divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), or —B($Q_{36}$)($Q_{37}$);

wherein $Q_1$ to $Q_7$, $Q_{11}$ to $Q_{17}$, $Q_{21}$ to $Q_{27}$ and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Embodiments are also directed to an organic light-emitting device comprising a first electrode; a second electrode disposed opposite to the first electrode; and an organic layer disposed between the first electrode and the second electrode and comprising an emission layer, wherein the organic layer comprises at least one of the condensed cyclic compounds of claim 1 above.

BRIEF DESCRIPTION OF THE DRAWING

Features will become apparent to those of skill in the art by describing in detail exemplary embodiments with reference to the attached drawing in which:

FIG. 1 illustrates a schematic view of a structure of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an embodiment, there is provided a condensed cyclic compound represented by Formula 1.

<Formula 1>

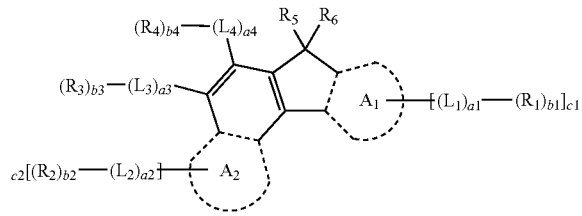

wherein, in Formula 1, $A_1$ ring is a $C_2$-$C_{20}$ heterocyclic group including at least one N as a ring member atom, and $A_2$ ring is a $C_6$-$C_{20}$ cyclic group, or a $C_2$-$C_{20}$ heterocyclic group including at least one N as a ring member atom, wherein $A_2$ ring is not a benzene when $A_1$ ring is a pyridine.

In Formula 1, $A_1$ ring may be a ring condensed to an adjacent 5-membered ring while sharing carbon with the same, and $A_2$ ring may be a ring condensed to a 6-membered ring while sharing carbon with the same.

For example, in Formula 1, $A_1$ ring may be a pyridine, and $A_2$ ring may be a naphthalene, a pyridine, a pyrimidine, a quinoline, an isoquinoline, a benzoquinoline, a quinoxaline, a quinazoline or a phenanthroline. In some embodiments, $A_1$ ring may be a pyrimidine, a quinoline, an isoquinoline, a benzoquinoline, a quinoxaline, a quinazoline, or a phenanthroline, and $A_2$ ring may be a benzene, a naphthalene, a pyridine, a pyrimidine, a quinoline, an isoquinoline, a benzoquinoline, a quinoxaline, a quinazoline, or a phenanthroline.

For example, in Formula 1, $A_1$ ring may be a pyridine, and $A_2$ ring may be a naphthalene or a pyridine. In some embodiments, $A_1$ ring may be a quinoline, a benzoquinoline, or a phenanthroline, and $A_2$ ring may be a benzene, a naphthalene, a pyridine, or a quinoline. However, embodiments are not limited thereto.

In Formula 1, $L_1$ to $L_4$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, in Formula 1, $L_1$ to $L_4$ may be are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, a thiadiazolyene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a phenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, a thiadiazolyene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, an a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, in Formula 1, $L_1$ to $L_4$ may each independently be selected from groups represented by Formulae 3-1 to 3-33, but are not limited thereto:

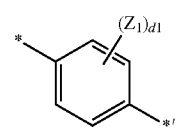

Formula 3-1

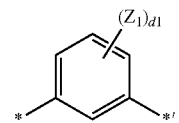

Formula 3-2

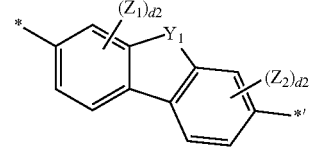

Formula 3-3

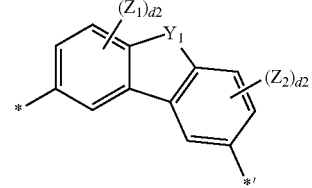

Formula 3-4

-continued
Formula 3-5
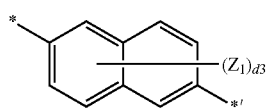
Formula 3-6
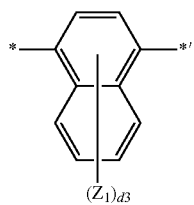
Formula 3-7
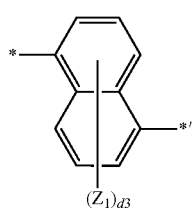
Formula 3-8
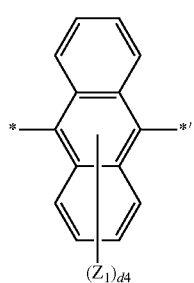
Formula 3-9
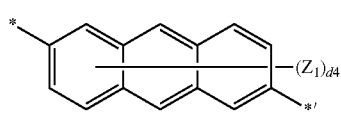
Formula 3-10
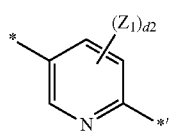
Formula 3-11
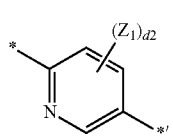
Formula 3-12
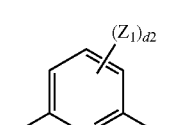
Formula 3-13
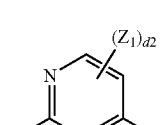
Formula 3-14
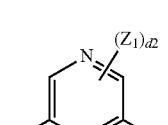
Formula 3-15
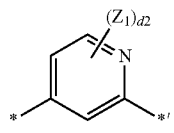
Formula 3-16
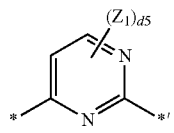
Formula 3-17
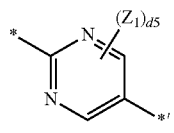
Formula 3-18
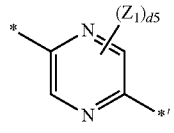
Formula 3-19
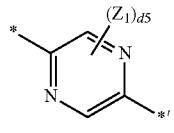
Formula 3-20
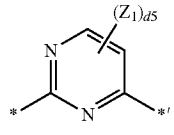
Formula 3-21
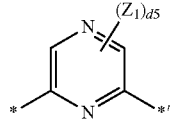
Formula 3-22
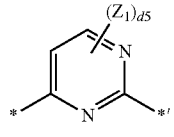
Formula 3-23
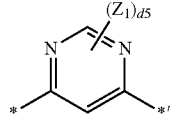
Formula 3-24
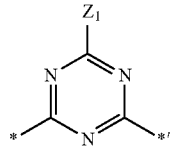
Formula 3-25
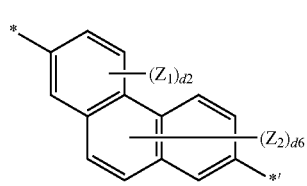

-continued

Formula 3-26
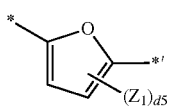

Formula 3-27
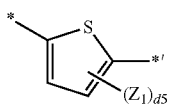

Formula 3-28
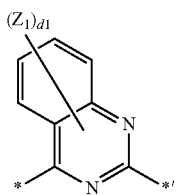

Formula 3-29
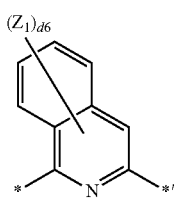

Formula 3-30
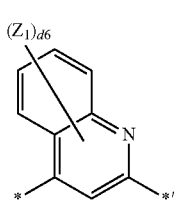

Formula 3-31
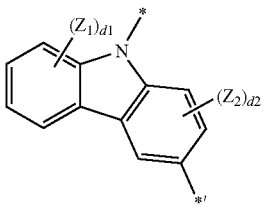

Formula 3-32
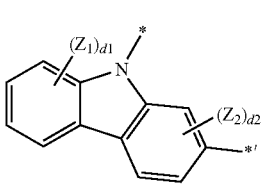

Formula 3-33
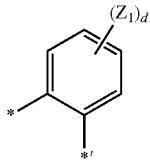

In Formulae 3-1 to 3-33, $Y_1$ may be O, S, $C(Z_3)(Z_4)$, $N(Z_5)$, or $Si(Z_6)(Z_7)$, $Z_1$ to $Z_7$ may each independently be selected from a hydrogen, a deuterium, —F, —Cl, —Br, —I, a hydroxyl group, a cyano group, a nitro group, an amino group, an amidino groups, a hydrazine, a hydrazone, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzo-fluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer selected from 1 to 4, d2 may be an integer selected from 1 to 3, d3 may be an integer selected from 1 to 6, d4 may be an integer selected from 1 to 8, d5 may be 1 or 2, d6 may be an integer selected from 1 to 5, and

* and *′ may be binding sites with adjacent atoms.

In some other embodiments, in Formula 1, $L_1$ to $L_4$ may each independently be selected from groups represented by one of Formulae 4-1 to 4-24, but are not limited thereto:

Formula 4-1
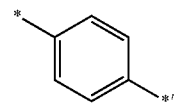

Formula 4-2
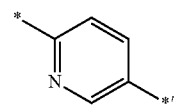

Formula 4-3
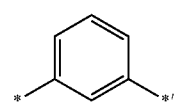

Formula 4-4
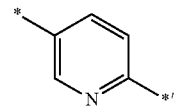

Formula 4-5
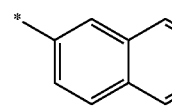

Formula 4-6
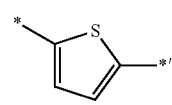

Formula 4-7
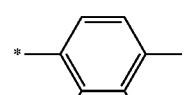

Formula 4-8
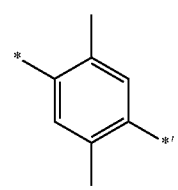

-continued

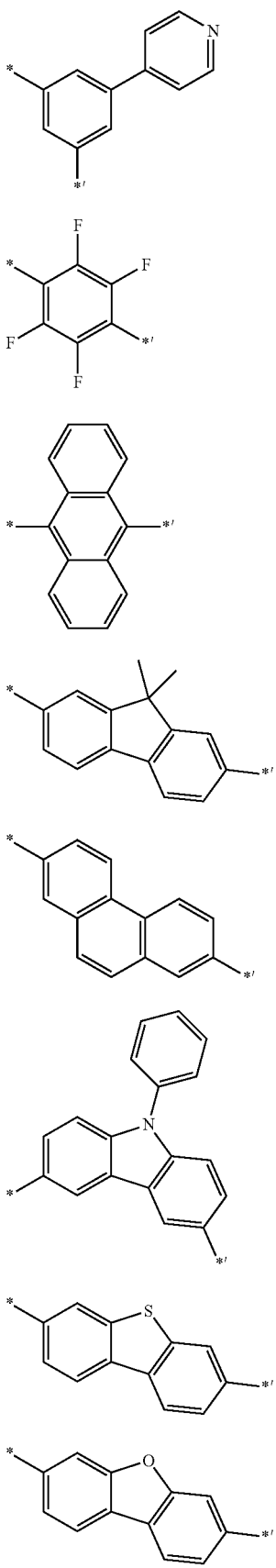

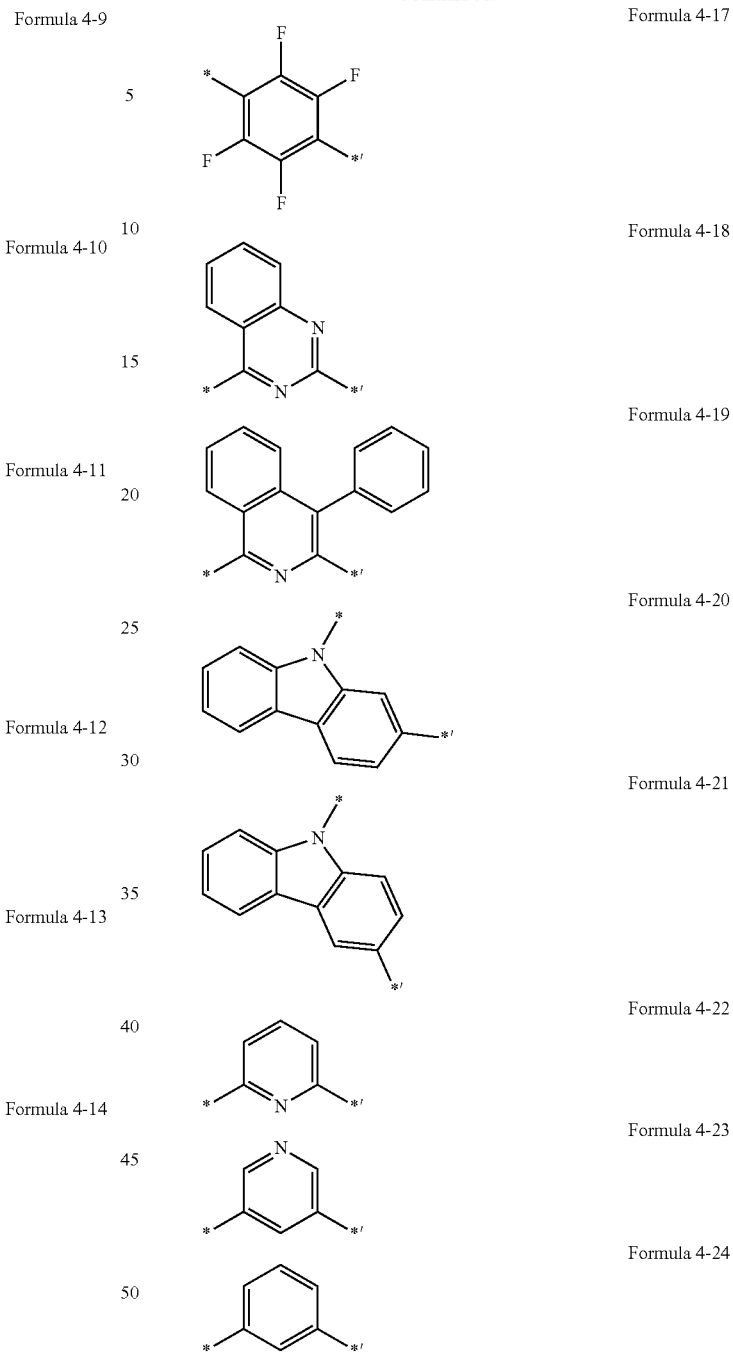

In Formulae 4-1 and 4-24, * and *' are binding sites with adjacent groups.

In Formula 1, a1, which indicates the number of $L_1$s, may be an integer selected from 0 to 3. For example, a1 in Formula 1 may be 0 or 1, but is not limited thereto. When a1 is 0, *-$(L_1)_{a1}$-*' is a single bond. When a1 is 2 or more, two or more $L_1$s may be identical or differ. In Formula 1, a2, a3, and a4 may be understood based on the description of a1 and the structure of Formula 1.

In Formula 1, a1 to a4 may each independently be 0 or 1.

In Formula 1, $R_1$ to $R_6$ may each independently be selected from a hydrogen, a deuterium, —F, —Cl, —Br, —I, a hydroxyl group, a cyano group, a nitro group, an amino group, an amidino group, a hydrazine group, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

In some embodiments, in Formula 1, $R_1$ to $R_4$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_3$)($Q_4$)($Q_5$). In Formula 1, $R_5$ and $R_6$ may each independently be selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or un substituted monovalent non-aromatic condensed heteropolycyclic group, but are not limited thereto.

For example, in Formula 1, $R_1$ to $R_4$ may each independently be a hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, cyclopentyl group, a cyclohexyl group, a cycloheptyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group; and $Si(Q_3)(Q_4)(Q_5)$, wherein $Q_3$ to $Q_5$ may each independently be selected from a $C_1$-$C_{20}$ alkyl group, a $C_1$-$C_{20}$ alkoxy group, a phenyl group, and a naphthyl group. However, embodiments are not limited thereto.

In some other embodiments, in Formula 1, $R_1$ to $R_4$ may each independently be selected from a hydrogen, a deuterium, —F, —Cl, —Br, —I, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group. However, embodiments are not limited thereto.

In some embodiments, in Formula 1, $R_5$ and $R_6$ may each independently be selected from a $C_1$-$C_{20}$ alkyl group and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group. However, embodiments are not limited thereto.

For example, in Formula 1, $R_1$ to $R_4$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by Formulae 6-1 to 6-62; and $R_5$ and $R_6$ may each independently be selected from a $C_1$-$C_{20}$ alkyl group, a $C_1$-$C_{20}$ alkoxy group, and groups represented by Formulae 6-1 to 6-62. However, embodiments are not limited thereto.

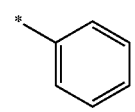

Formula 6-1

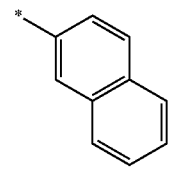

Formula 6-2

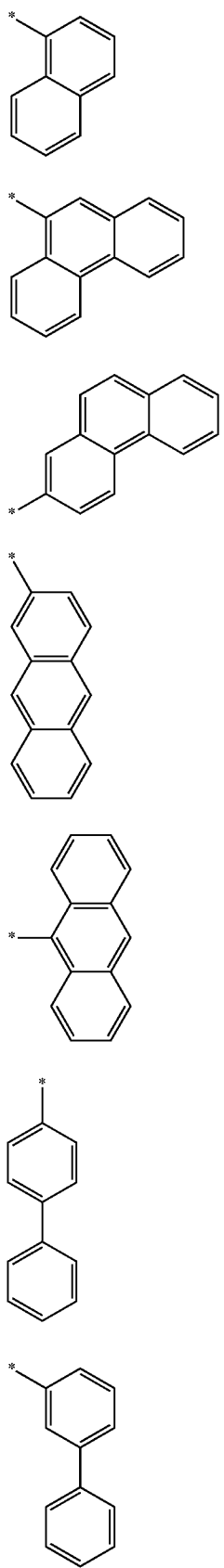
Formula 6-3
Formula 6-4
Formula 6-5
Formula 6-6
Formula 6-7
Formula 6-8
Formula 6-9
Formula 6-10
Formula 6-11
Formula 6-12
Formula 6-13
Formula 6-14
Formula 6-15
Formula 6-16

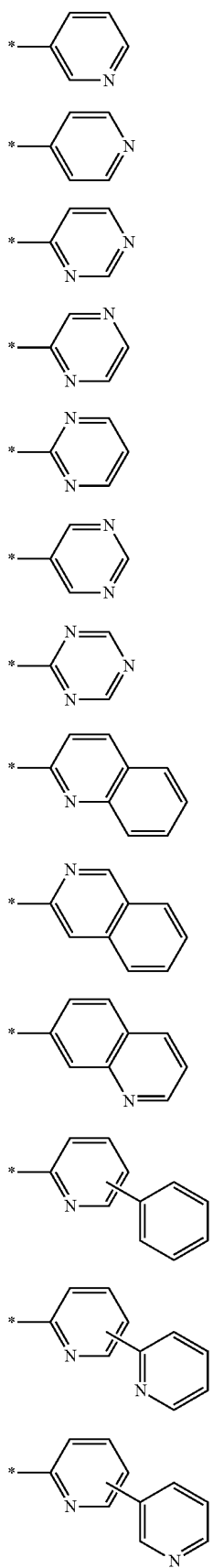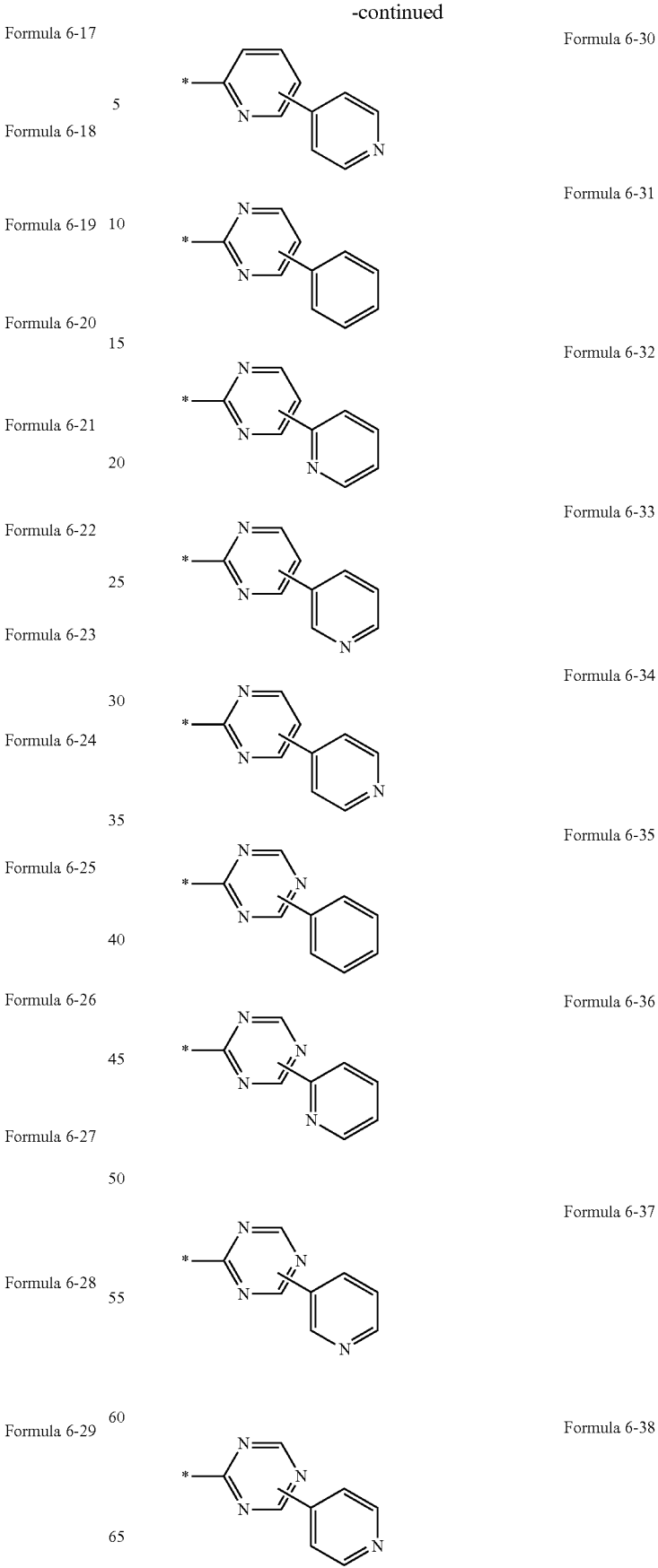

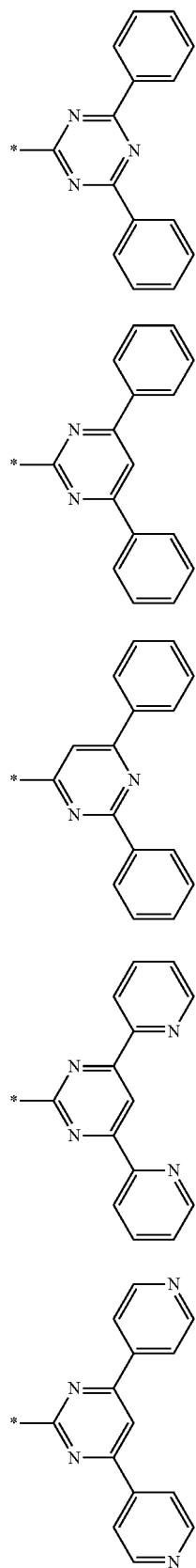
Formula 6-39
Formula 6-40
Formula 6-41
Formula 6-42
Formula 6-43
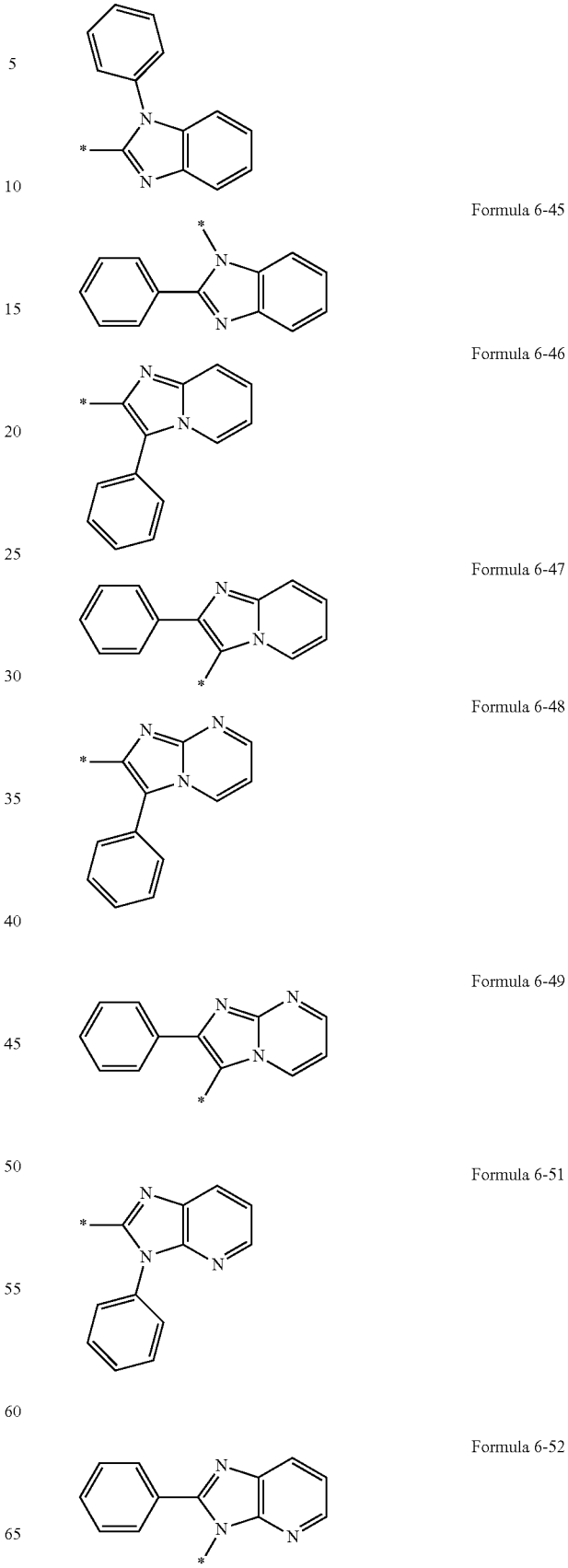
Formula 6-44
Formula 6-45
Formula 6-46
Formula 6-47
Formula 6-48
Formula 6-49
Formula 6-51
Formula 6-52

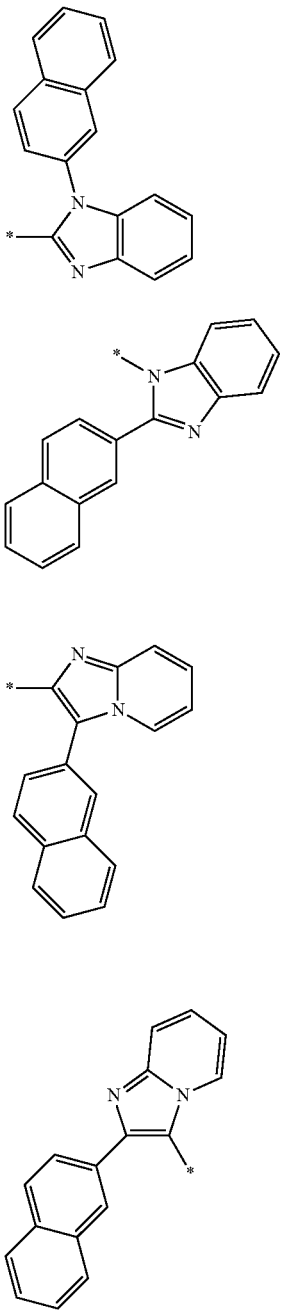

Formula 6-53

Formula 6-54

Formula 6-55

Formula 6-56

Formula 6-57

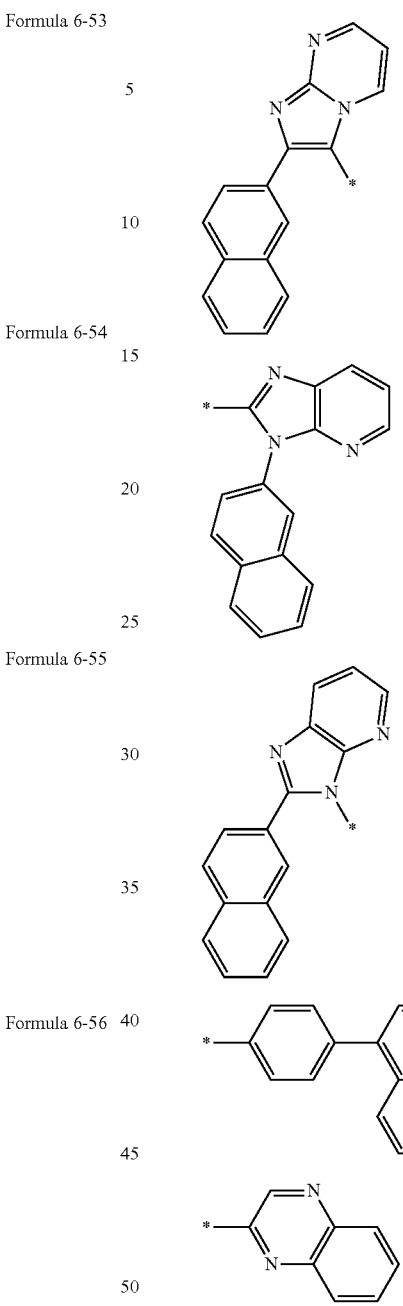

Formula 6-58

Formula 6-59

Formula 6-60

Formula 6-61

Formula 6-62

In Formulae 6-1 and 6-62, * is a binding site with an adjacent group.

In Formula 1, b1, which indicates the number of $R_1$s, may be an integer selected from 0 to 3. In some embodiments, b1 may be 1 or 2. Two or more $R_1$s may be identical or differ. In Formula 1, b2, b3, and b4 may be understood based on the description of b1 and the structure of Formula 1.

In Formula 1, c1, which indicates the number of *-[$(L_1)_{a1}$-$(R_1)_{b1}$]s, may be an integer selected from 1 to 4. In some embodiments, c1 may be 1, 2 or 3. When c1 is 2 or more, two or more *-[$(L_1)_{a1}$-$(R_1)_{b1}$]s may be identical or differ. In Formula 1, c2 may be understood based on the description of c1 and the structure of Formula 1.

In some embodiments, in Formula 1, $R_5$ and $R_6$ may each independently be selected from a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, and $R_5$ and $R_6$ may be linked to each other via a single bond or a substituted or unsubstituted $C_1$-$C_5$ alkylene group, for example, to form a structure as in Formula 1A.

In some embodiments, the condensed cyclic compound of Formula 1 may be represented by Formula 1A or 1B.

<Formula 1A>

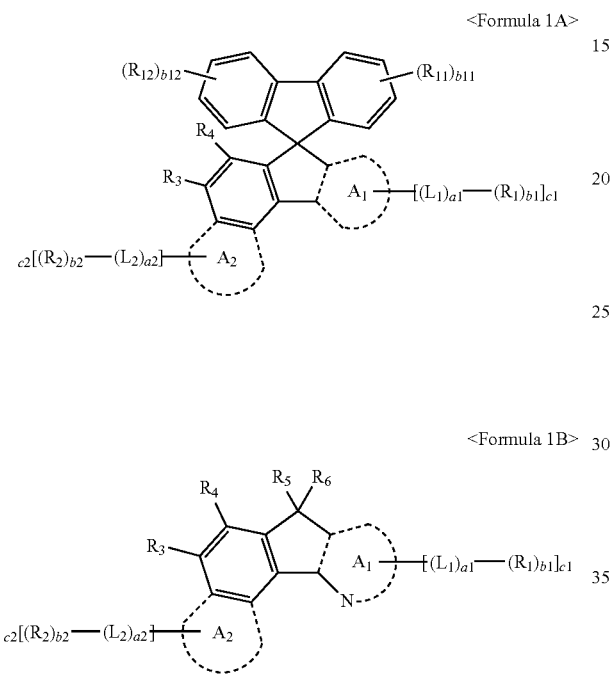

<Formula 1B>

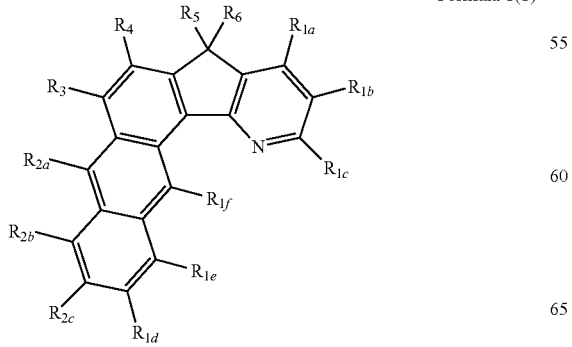

In Formulae 1A and 1B, $A_1$ ring, $A_2$ ring, $L_1$, $L_2$, a1, a2, $R_1$ to $R_6$, b1, b2, c1, and c2 may be defined the same as those described herein; $R_{11}$ and $R_{12}$ may be each independently defined the same as $R_1$ described herein; and b11 and b12 may each independently be an integer selected from 1 to 4.

In some embodiments, the condensed cyclic compound of Formula 1 may be represented by one of Formulae 1(1) to 1(13) and Formulae 1A(1) to 1A(13). However, embodiments are not limited thereto.

Formula 1(1)

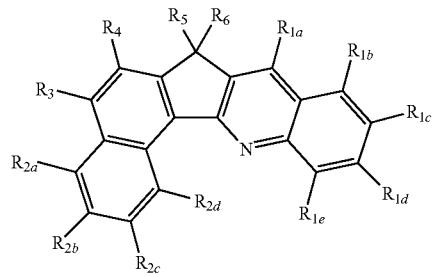

Formula 1(2)

Formula 1(3)

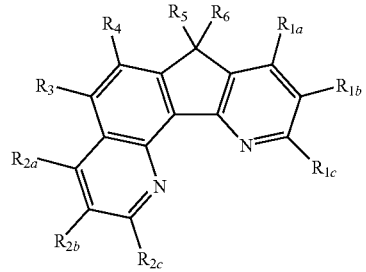

Formula 1(4)

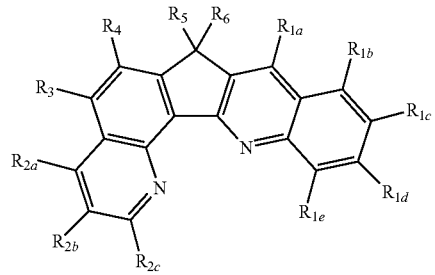

Formula 1(5)

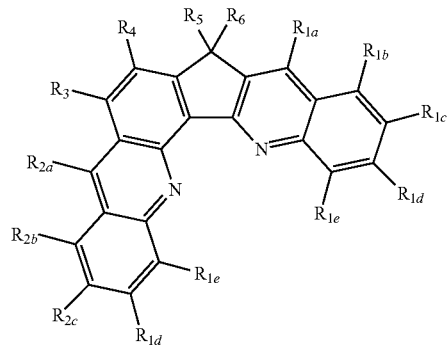

Formula 1(6)

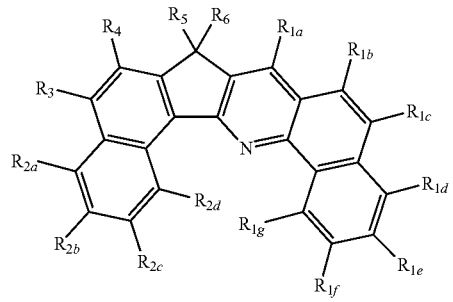

Formula 1(7)
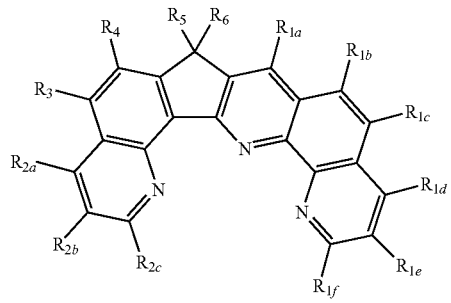
Formula 1(8)
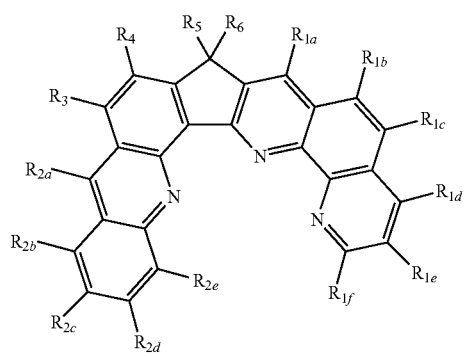
Formula 1(9)
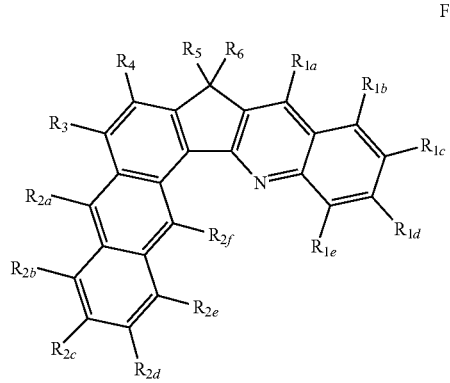
Formula 1(10)
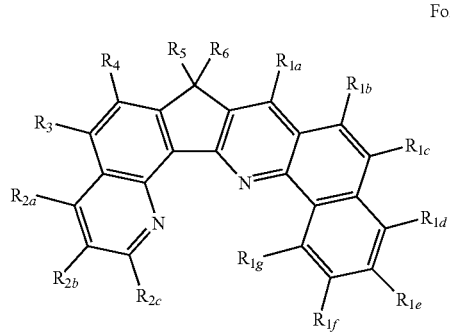
Formula 1(11)
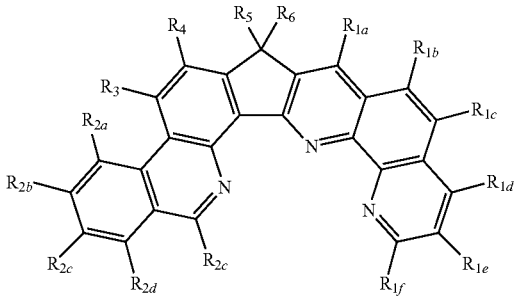
Formula 1(12)
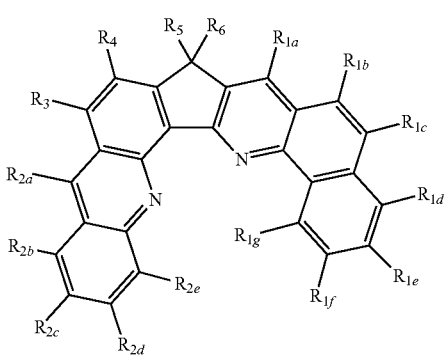
Formula 1(13)
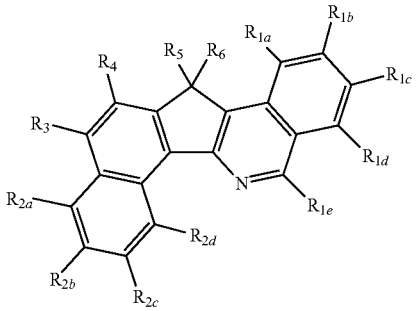
Formula 1A(1)
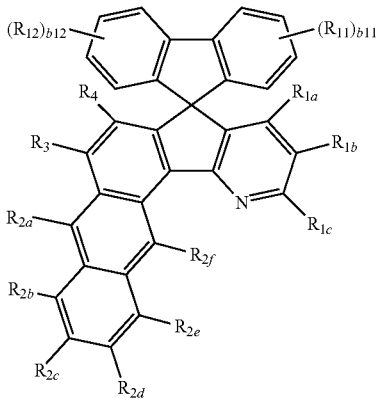

-continued
Formula 1A(2)
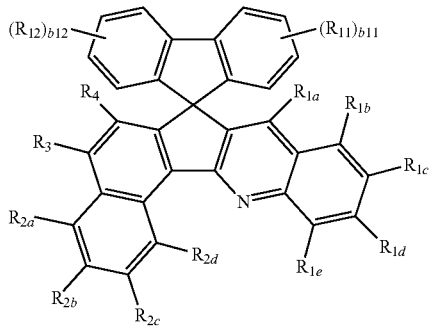
Formula 1A(3)
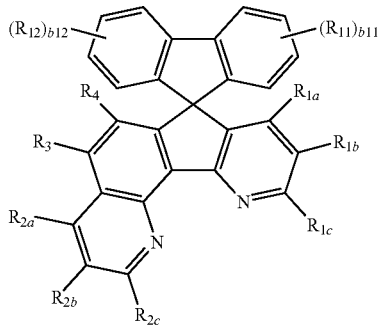
Formula 1A(4)
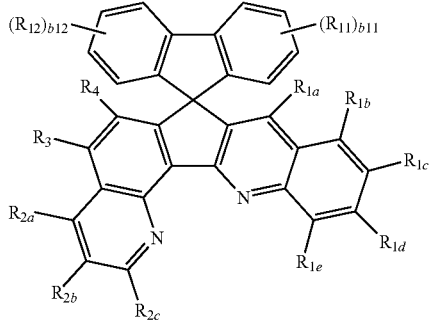
Formula 1A(5)
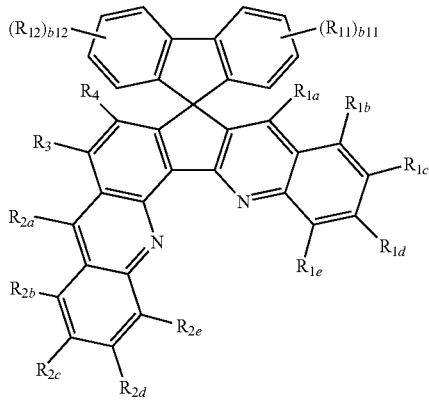
-continued
Formula 1A(6)
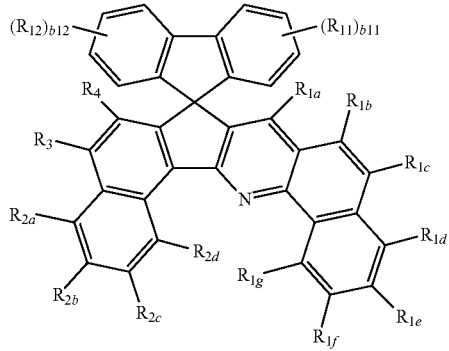
Formula 1A(7)
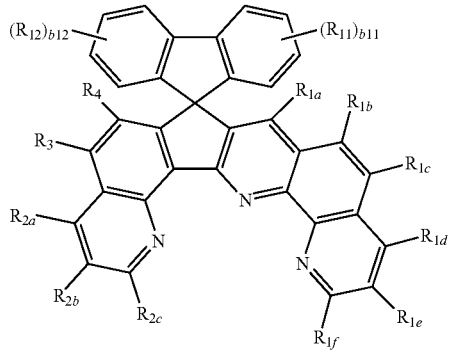
Formula 1A(8)
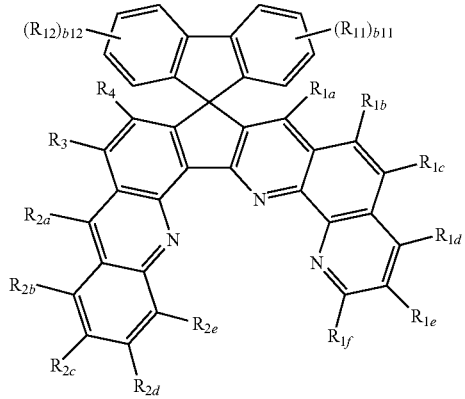
Formula 1A(9)
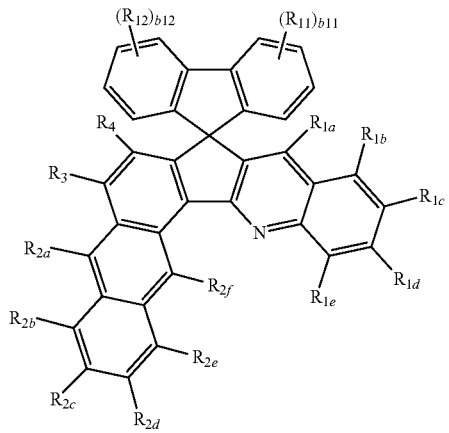

Formula 1A(10)

Formula 1A(11)

Formula 1A(12)

Formula 1A(13)

In Formulae 1(1) to 1(13) and Formula 1A(1) to 1A(13), $R_3$ and $R_4$ may be defined the same as those described herein, $R_{1a}$ to $R_{1g}$, $R_{11}$, and $R_{12}$ may each independently be defined the same as $R_1$ described herein, and $R_{2a}$ to $R_{2f}$ may each independently be defined the same as $R_2$ described herein.

For example, in Formulae 1A(1) to 1A(13) of Formulae 1(1) to 1(13), $R_{1a}$ to $R_{1g}$, $R_{2a}$ to $R_{2f}$, $R_{11}$, and $R_{12}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group and an imidazopyrimidinyl group; and a phenyl group, a naphthyl group, a fluorenyl group, a Spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, in Formulae 1A(1) to 1A(13) of Formulae 1(1) to 1(13), $R_{1a}$ to $R_{1g}$, $R_{2a}$ to $R_{2f}$, $R_{11}$, and $R_{12}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by Formulae 6-1 to 6-62. However, embodiments are not limited thereto.

In some embodiments, the condensed cyclic compound represented by Formula 1 may be one of Compounds 1 to 67.

1

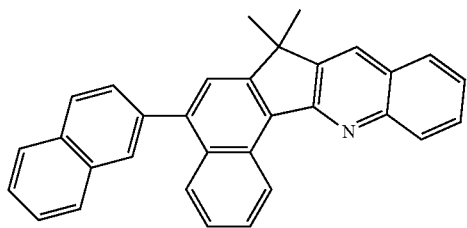

2

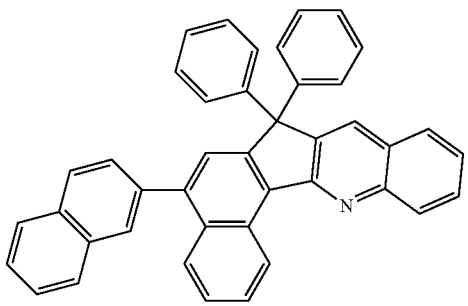

3

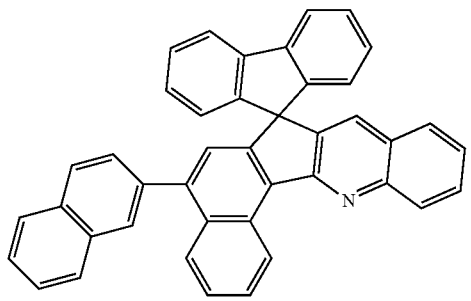

4

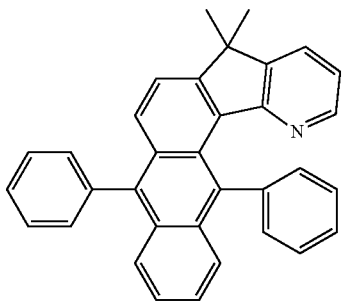

5

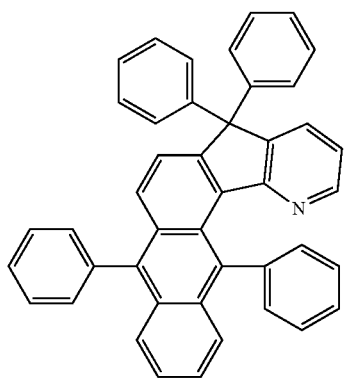

6

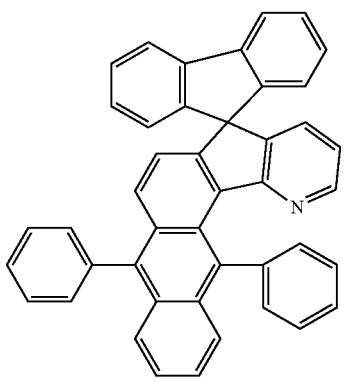

-continued
7
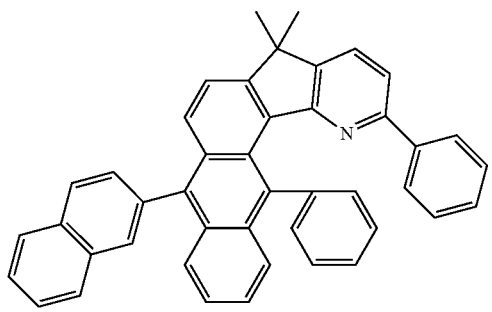
8
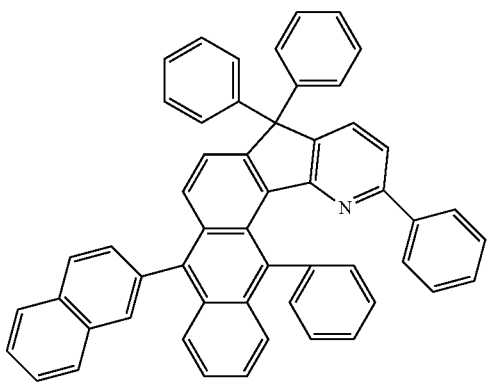
9
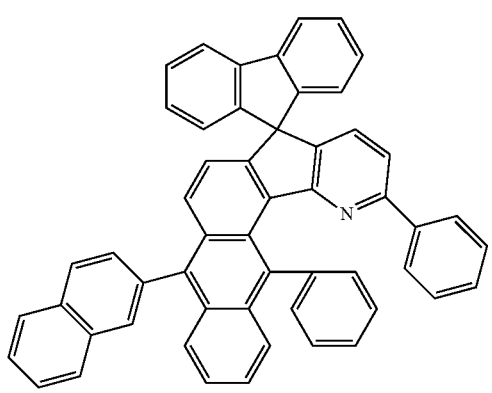
10
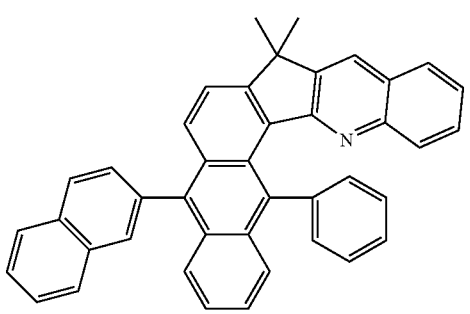
11
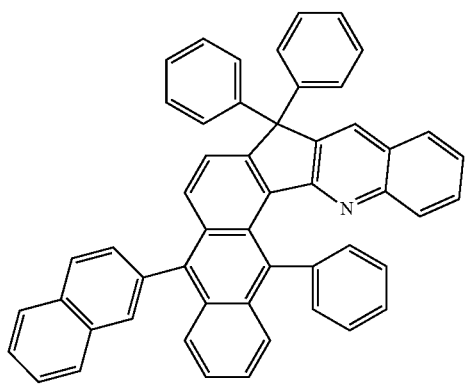
12
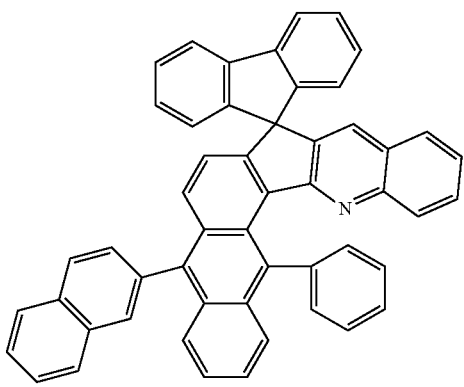
13
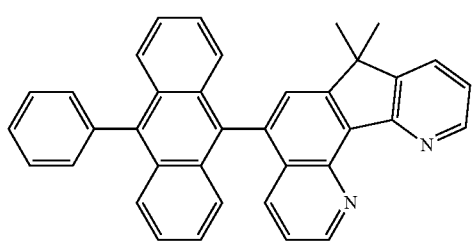
14
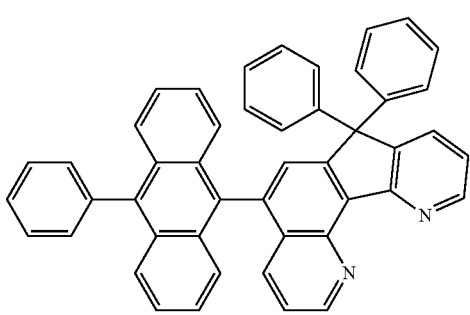

-continued
15
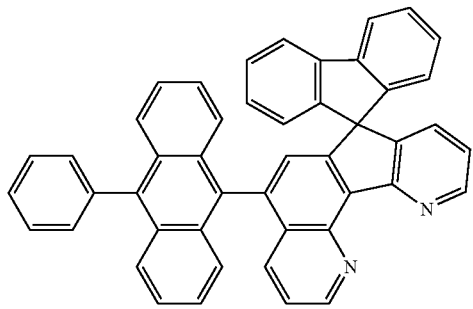
16
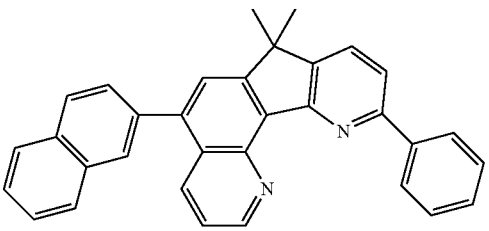
17
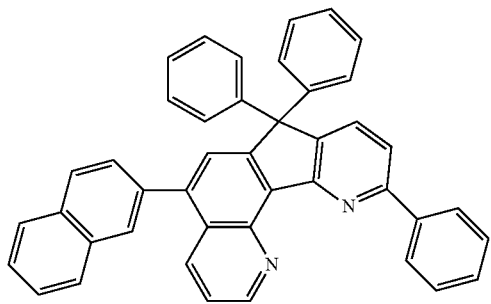
18
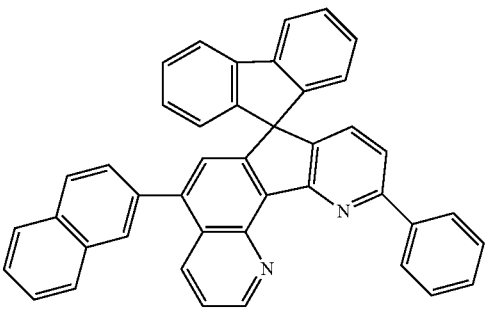
19
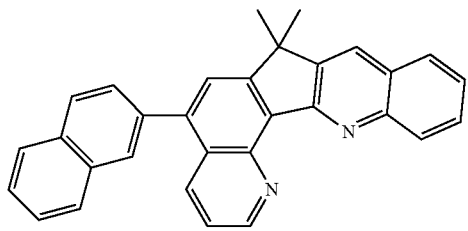
20
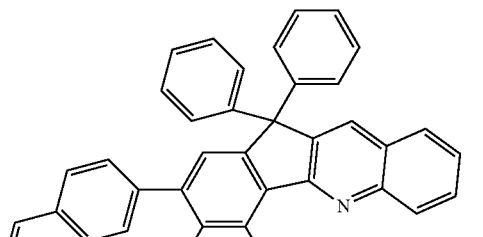
21
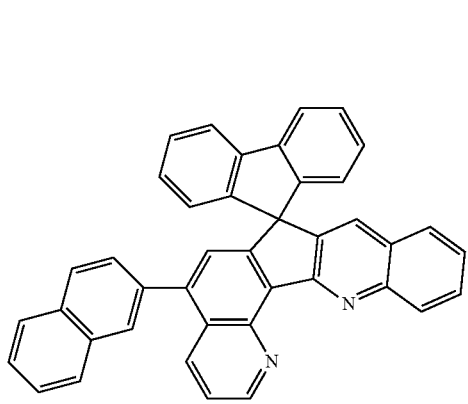
22
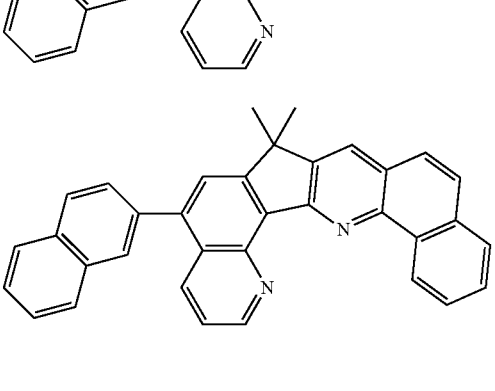
23
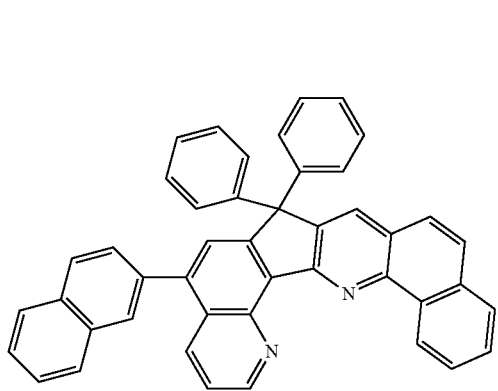
24
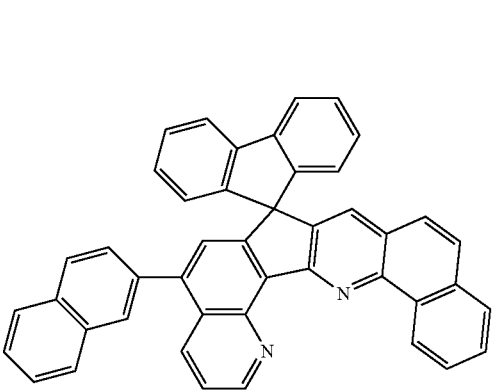

-continued
25
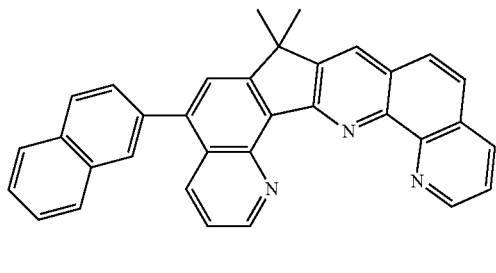
26
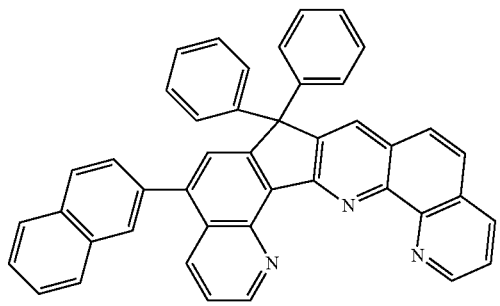
27
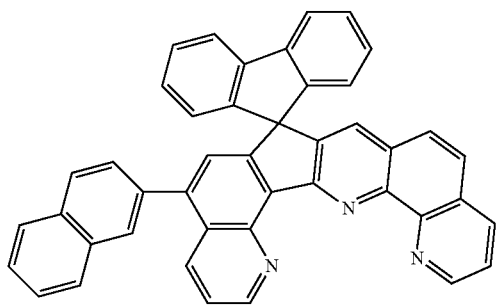
28
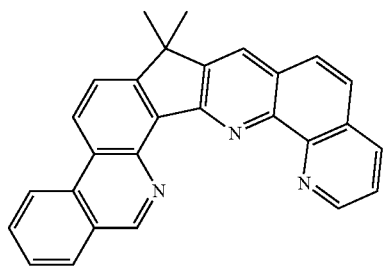
29
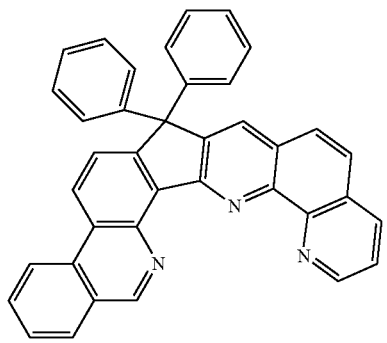
30
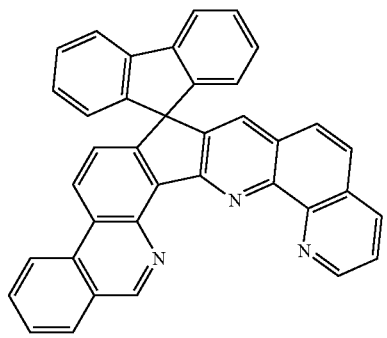
31
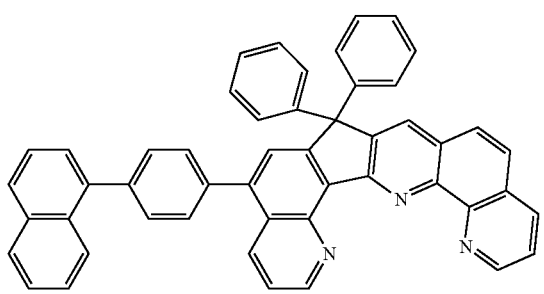
32
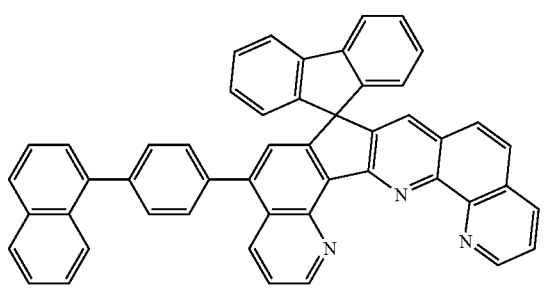
33
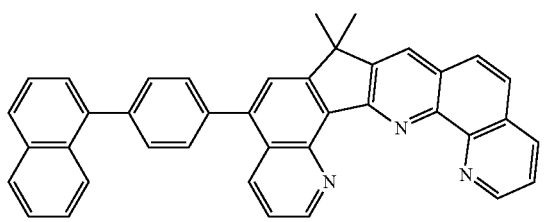
34
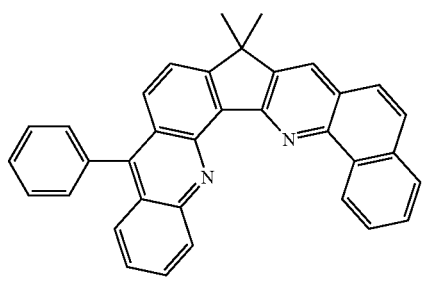

-continued
35
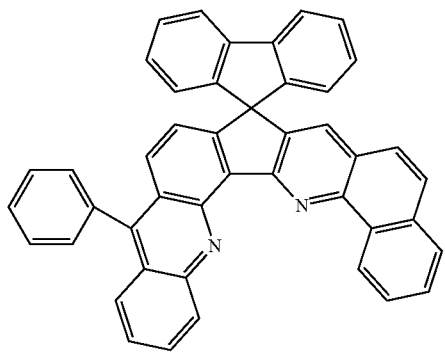
36
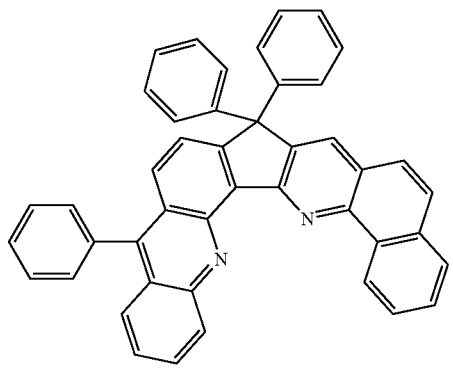
37
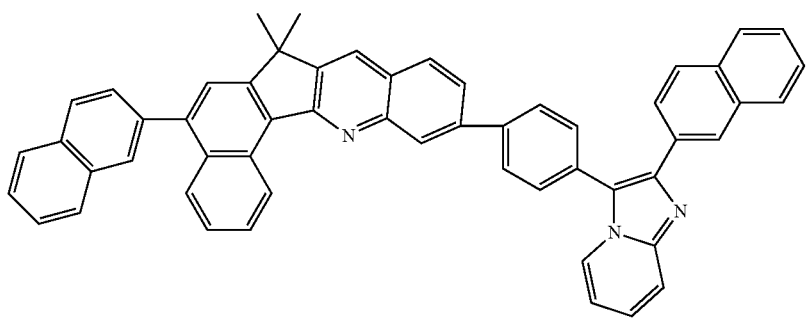
38
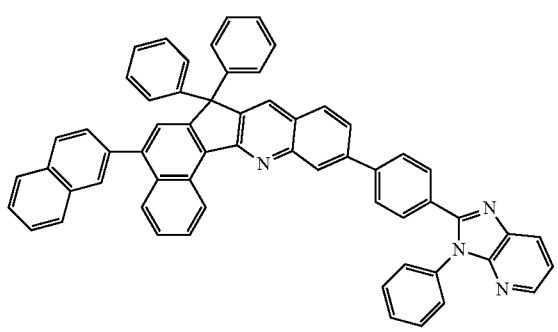
39
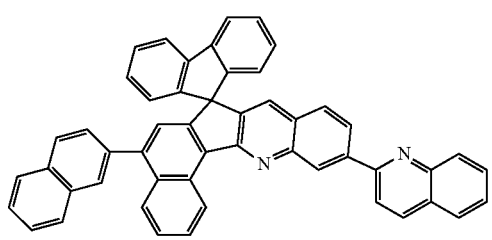
40
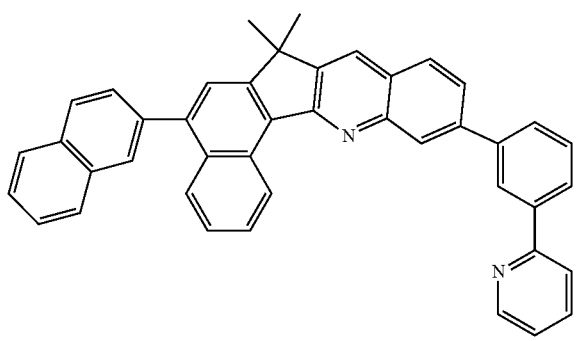

41
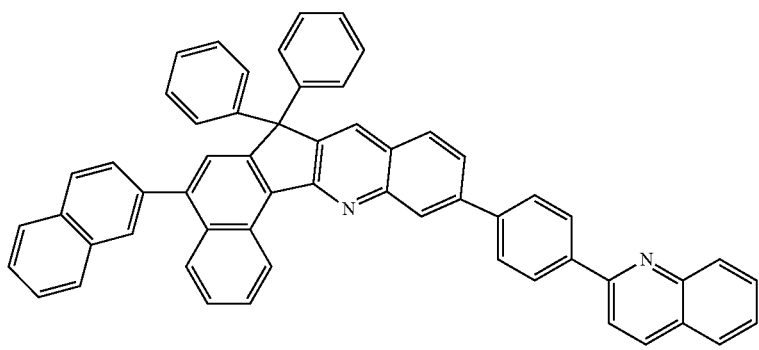
42
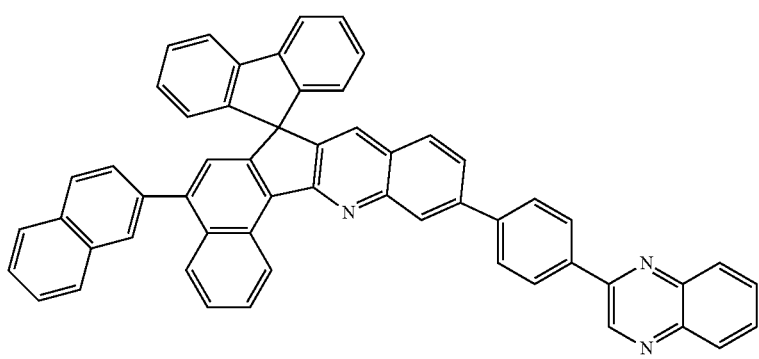
43
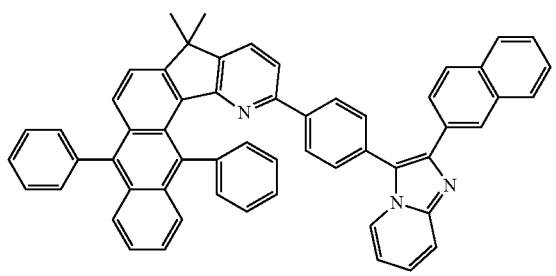
44
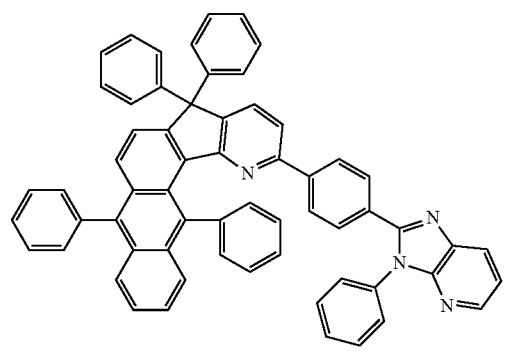
45
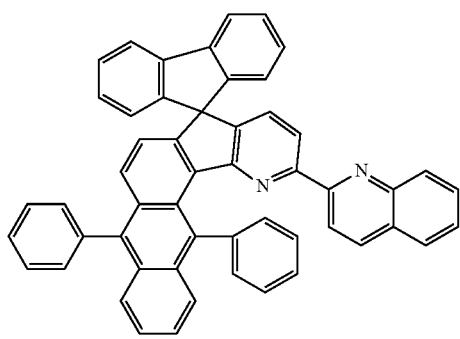
46
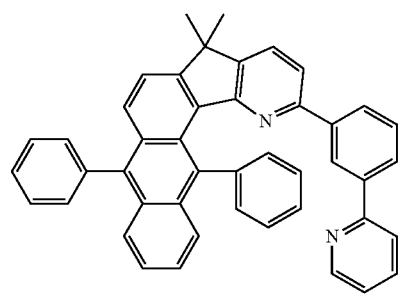

-continued
47
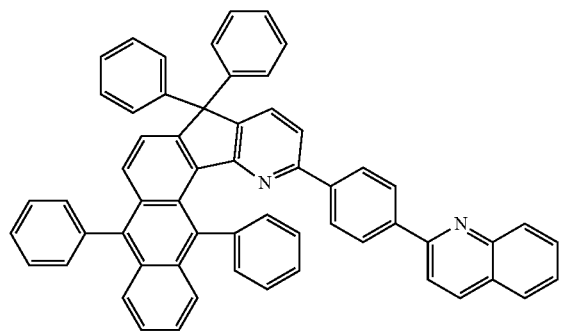
48
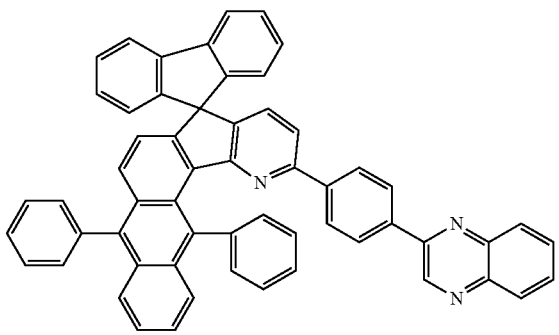
49
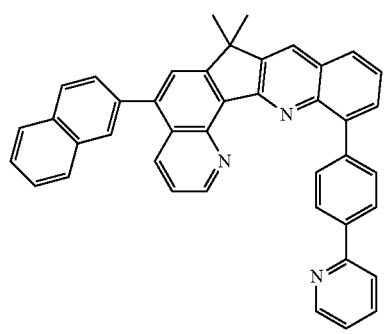
50
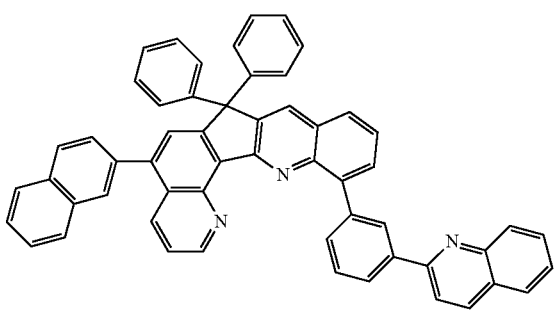
51
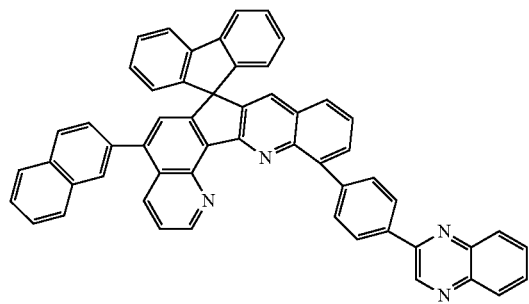
52
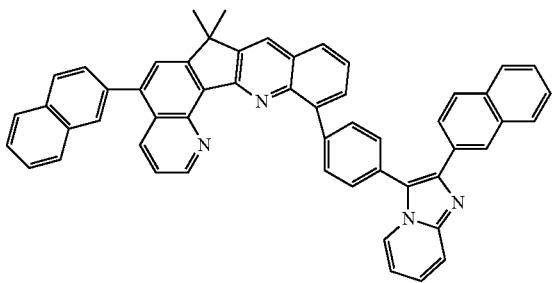
53
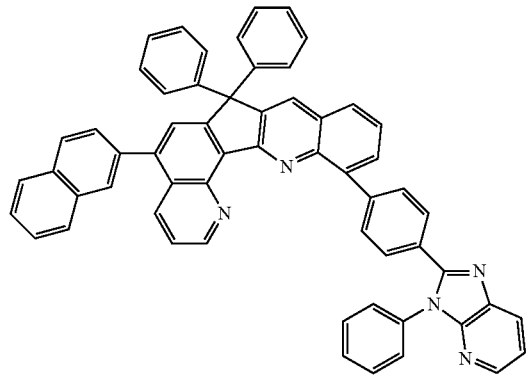
54
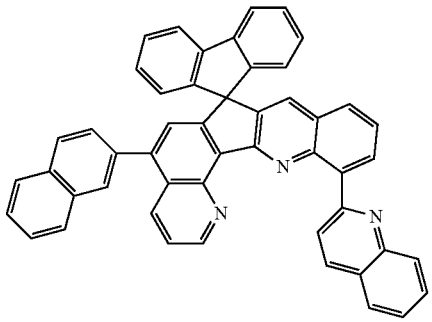

-continued
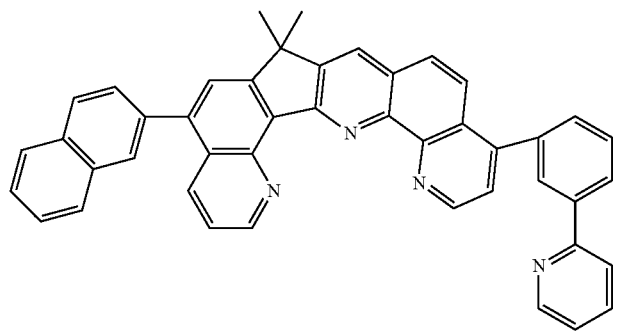
55
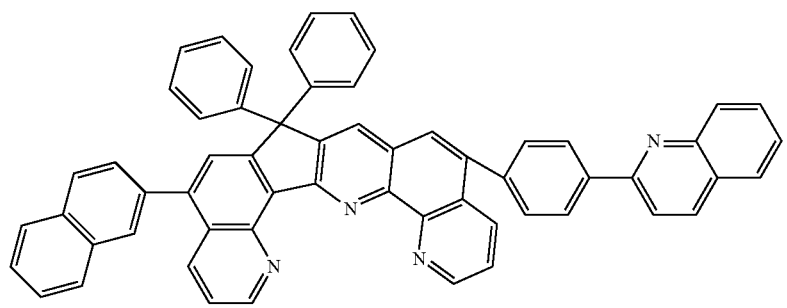
56
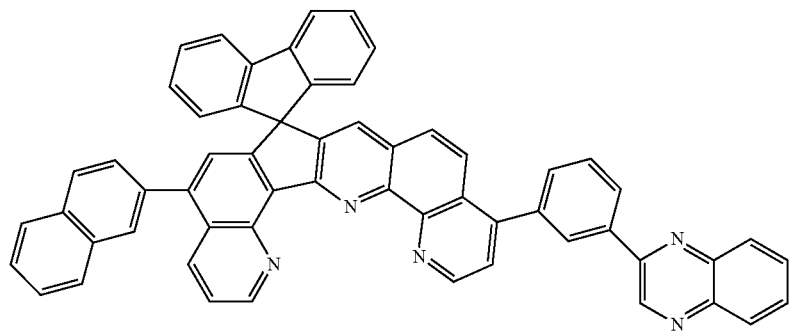
57
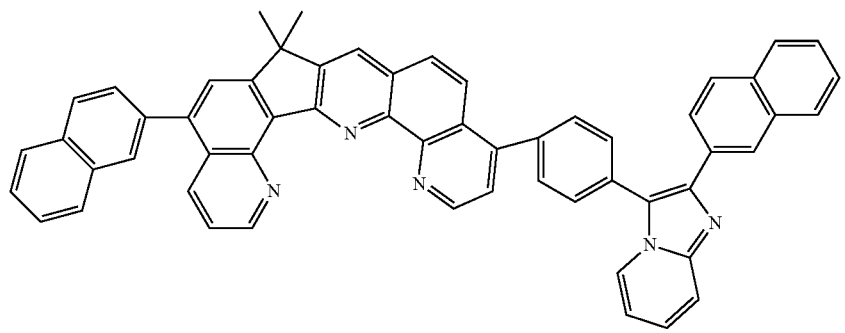
58

-continued
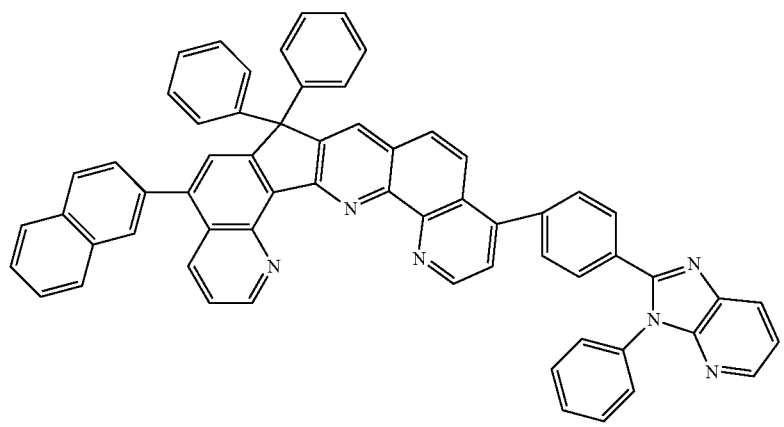
59
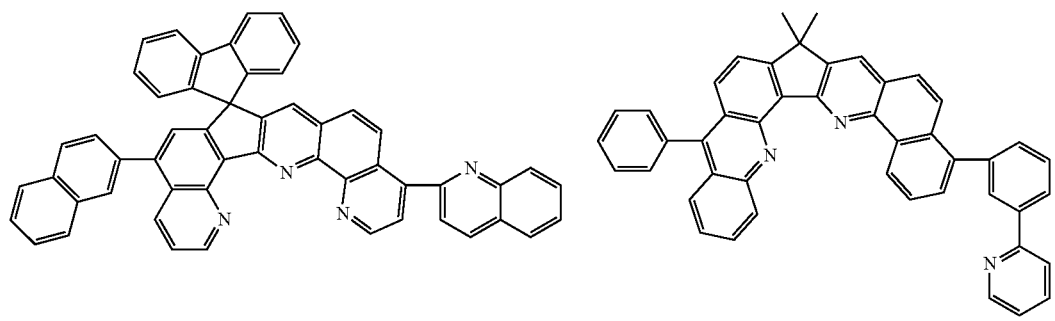
60
61
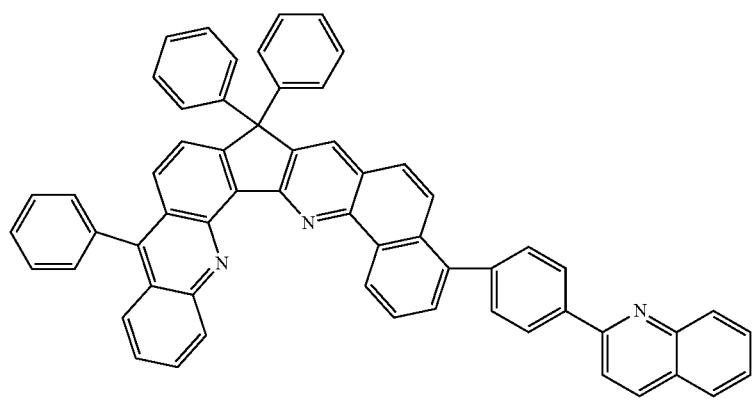
62
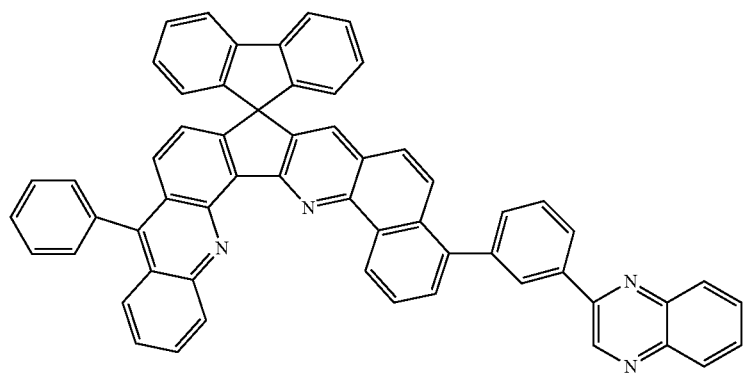
63

64

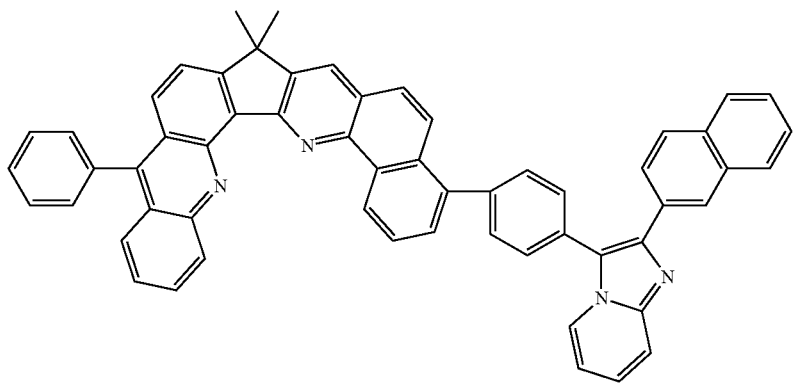

65

66

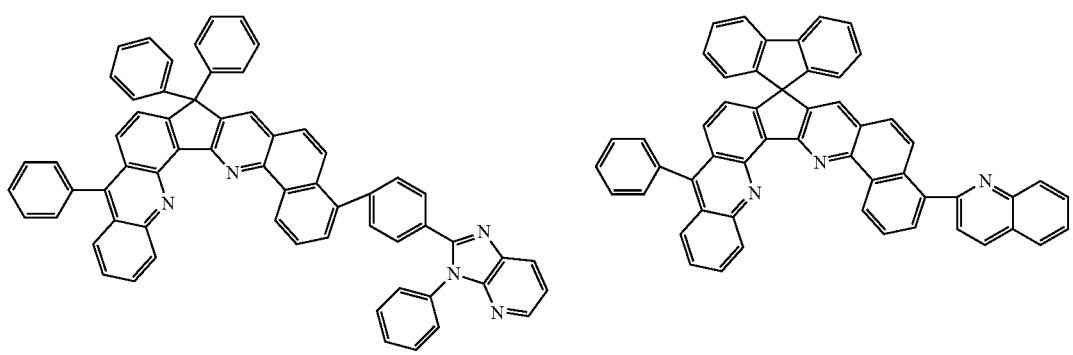

67

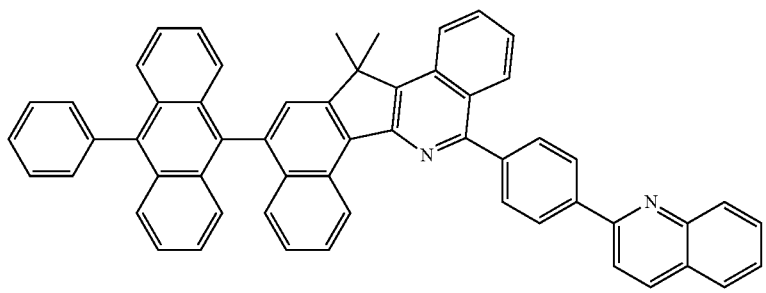

The condensed cyclic compound of Formula 1 may be synthesized using a general organic synthesis method. Methods of synthesizing the condensed cyclic compound of Formula 1 may be understood by based on the examples that will be described below.

At least one of the condensed cyclic compounds of Formula 1 may be used between a pair of electrodes of an organic light-emitting device. For example, the at least one of the condensed cyclic compounds of Formula 1 may be in an electron transport region, for example, in an electron transport layer.

According to another embodiment, an organic light-emitting device includes a first electrode, a second electrode disposed opposite to the first electrode, and an organic layer disposed between the first electrode and the second electrode and including an emission layer, wherein the organic layer includes at least one of the condensed cyclic compounds of Formula 1 described above.

As used herein, "[the organic layer (for example)] including at least one condensed cyclic compound means "[the organic layer] including one of the condensed cyclic compounds of Formula 1, or at least two different condensed cyclic compounds of Formula 1."

In some embodiments, the organic layer may include only Compound 1 as the condensed cyclic compound. In this regard, Compound 1 may be present in the emission layer of the organic light-emitting device. In some embodiments, the organic layer may include Compounds 1 and 2 as the condensed cyclic compounds. In this regard, Compounds 1 and 2 may be present both in the same layer (for example, in the electron transport layer) or may be present in different layers (for example, in the emission layer and the electron transport layer, respectively).

The organic layer may include i) a hole transport region disposed between the first electrode (anode) and the emission layer and including at least one of a hole injection layer, a hole transport layer, a buffer layer, and an electron blocking layer; and ii) an electron transport region disposed between the emission layer and the second electrode (cathode) and including at least one of a hole blocking layer, an electron transport layer, and an electron injection layer. The electron transport region may include at least one of the condensed cyclic compounds of Formula 1. For example, the electron transport region may include the electron transport layer, wherein the electron transport layer may include the at least one of the condensed cyclic compounds of Formula 1.

As used herein, the term "organic layer" refers to a single layer and/or a plurality of layers disposed between the first and second electrodes of the organic light-emitting device. A material in the "organic layer" is not limited to an organic material.

Hereinafter, a structure of an organic light-emitting device according to an embodiment and a method of manufacturing the same will now be described with reference to FIG. 1.

FIG. 1 is a schematic sectional view of an organic light-emitting device 10 according to an embodiment. Referring to FIG. 1, the organic light-emitting device 10 includes a first electrode 110, an organic layer 150, and a second electrode 190.

A substrate (not shown) may be disposed under the first electrode 110 or on the second electrode 190 in FIG. 1. The substrate may be a glass or transparent plastic substrate with good mechanical strength, thermal stability, transparency, surface smoothness, ease of handling, and water resistance.

For example, the first electrode 110 may be formed by depositing or sputtering a first electrode-forming material on the substrate 11. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO, but is not limited thereto.

The organic layer 150 may be disposed on the first electrode 110. The organic layer 150 may include an emission layer (EML).

The organic layer 150 may include a hole transport region disposed between the first electrode and the EML, and an electron transport region between the EML and the second electrode.

For example, the hole transport region may include at least one of a hole injection layer (HIL), a hole transport layer (HTL), a buffer layer, and an electron blocking layer (EBL). For example, the electron transport layer may include at least one of a hole blocking layer (HBL), an electron transport layer (ETL), and an electron injection layer (EIL). However, embodiments are not limited thereto.

The hole transport region may have a single-layered structure including a single material, a single-layered structure including a plurality of materials, or a multi-layered structure including a plurality of layers including different materials.

In some embodiments, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially disposed on the first electrode 110 in the order stated above. However, embodiments are not limited thereto.

When the hole transport region includes a HIL, the HIL may be formed on the first electrode 110 by using any of a variety of methods, for example, by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to about 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 rpm and a heat treatment temperature of about 800° C. to about 200° C.

When the hole transport region includes a HTL, the HTL may be formed on the first electrode 110 or the HIL by using any of a variety of methods, for example, by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL, and accordingly will not be described in detail.

In some embodiments, the hole transport region may include at least one of m-MTDATA, TDATA, 2-TNATA, NPB, (3-NPB, TPD, Spiro-TPD, Spiro-NPB, α-NPB, TAPC, HMTPD, 4,4',4''-tris(N-carbazolyl)triphenylamine (TCTA), polyaniline/dodecylbenzene sulfonic acid (Pani/DBSA), poly(3,4-ethylenedioxythiophene)/poly(4-styrene-sulfonate)(PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

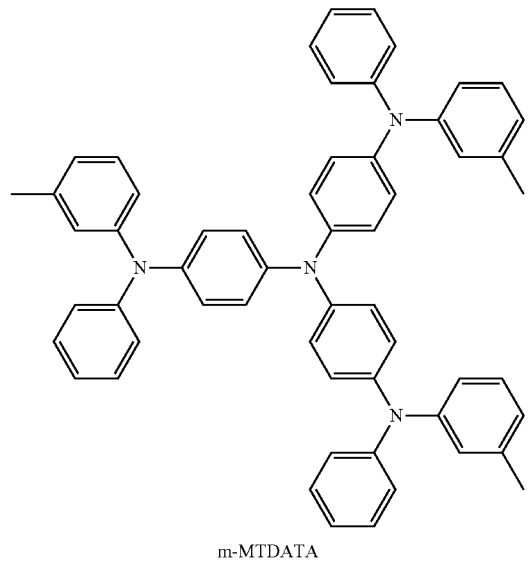

m-MTDATA

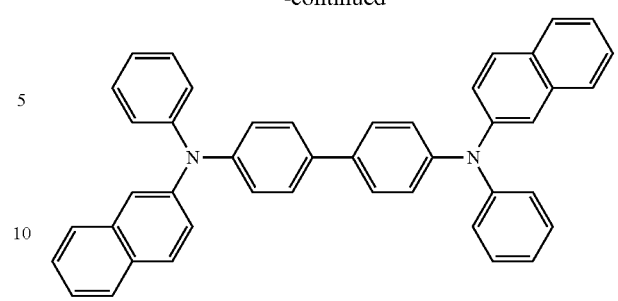
β-NPB
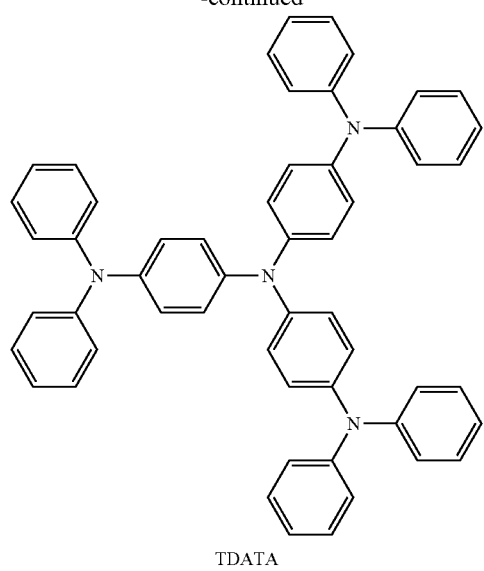
TDATA
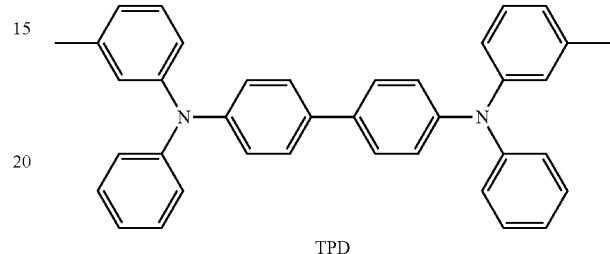
TPD
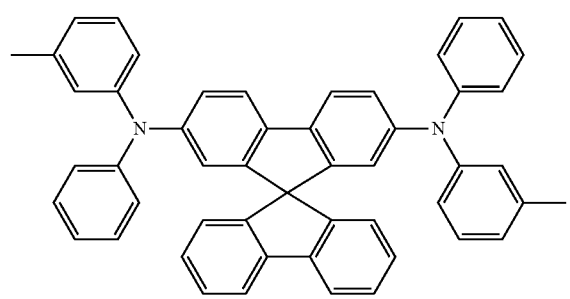
Spiro-TPD
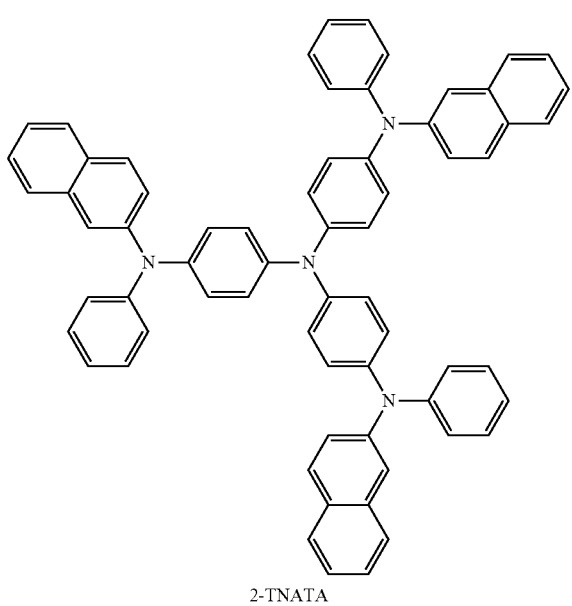
2-TNATA
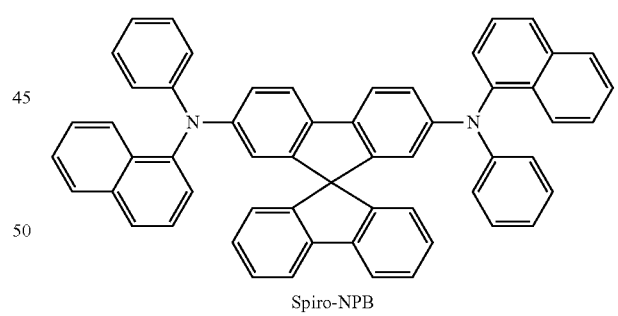
Spiro-NPB
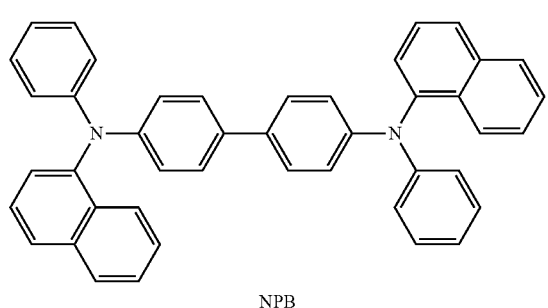
NPB
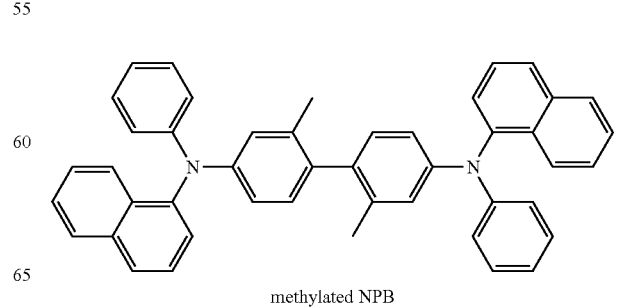
methylated NPB

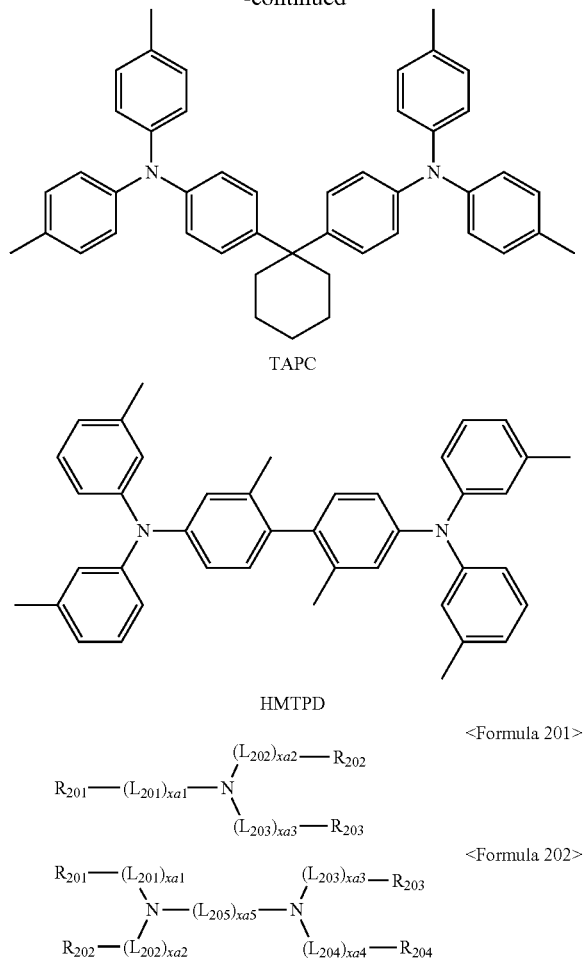

TAPC

HMTPD

<Formula 201>

R$_{201}$—(L$_{201}$)$_{xa1}$—N(L$_{202}$)$_{xa2}$—R$_{202}$ / (L$_{203}$)$_{xa3}$—R$_{203}$

<Formula 202>

R$_{201}$—(L$_{201}$)$_{xa1}$\ N—(L$_{205}$)$_{xa5}$—N /(L$_{203}$)$_{xa3}$—R$_{203}$ \(L$_{204}$)$_{xa4}$—R$_{204}$
R$_{202}$—(L$_{202}$)$_{xa2}$

In Formulae 201 and 202,

L$_{201}$ to L$_{205}$ may each independently be defined as described above in conjunction with L$_1$ in Formula 1;

xa1 to xa4 are each independently selected from 0, 1, 2, and 3;

xa5 may be selected from 1, 2, 3, 4, and 5;

R$_{201}$ to R$_{204}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202,

L$_{201}$ to L$_{205}$ may each independently be selected from a phenylene group, a naphthylene group, a fluorenylene group, a Spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may each independently be 0, 1, or 2;

xa5 may be 1, 2, or 3;

R$_{201}$ to R$_{204}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group. However, embodiments are not limited thereto.

The compound of Formula 201 may be represented by Formula 201A:

<Formula 201A>

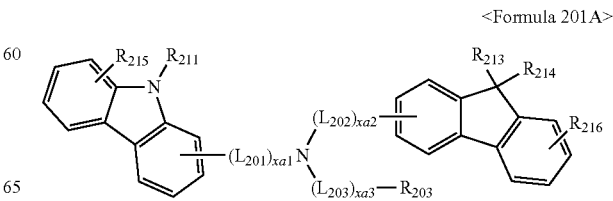

For example, the compound of Formula 201 may be represented by Formula 201A-1, but is not limited thereto:

<Formula 201A-1>

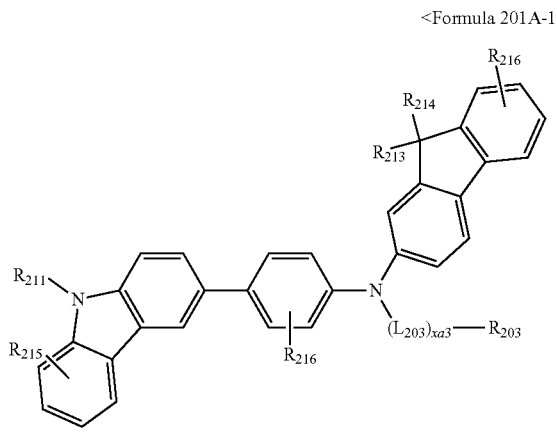

The compound of Formula 202 may be represented by Formula 202A, but is not limited thereto:

<Formula 202A>

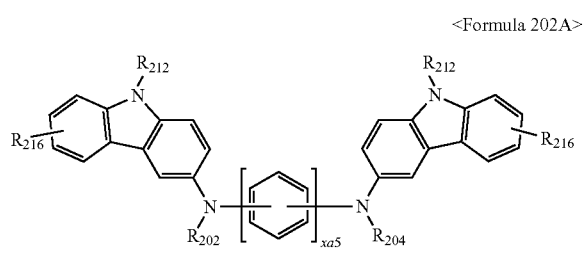

In Formulae 201A, 201A-1, and 202A, $L_{201}$ to $L_{203}$, xa1 to xa3, xa5, and $R_{202}$ to $R_{204}$ may be defined as described in conjunction with Formula 201;

$R_{211}$ and $R_{212}$ may be defined as described in conjunction with $R_{203}$ in Formula 201;

$R_{213}$ to $R_{216}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group.

In some other embodiments, in Formulae 201A, 201A-1, and 202A, $L_{201}$ to $L_{203}$ may each independently be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xa1 to xa3 may each independently be 0 or 1, $R_{202}$ to $R_{204}$, $R_{211}$, and $R_{212}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{213}$ and $R_{214}$ may each independently be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{215}$ and $R_{216}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xa5 may be 1 or 2.

In Formulae 201A and 201A-1, $R_{213}$ and $R_{214}$ may be linked to each other to form a saturated or unsaturated ring.

The compound represented by Formula 201, and the compound represented by Formula 202 may be compounds HT1 to HT20 illustrated below, but are not limited thereto.

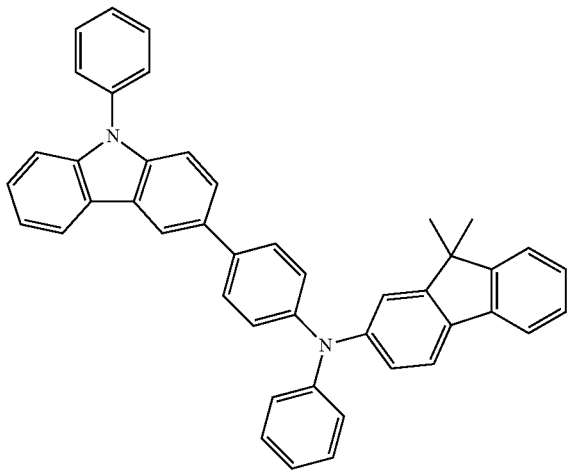

HT1

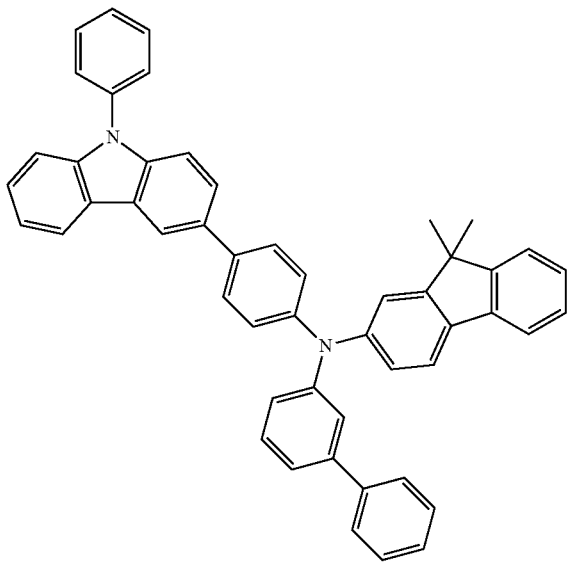

HT2

HT3
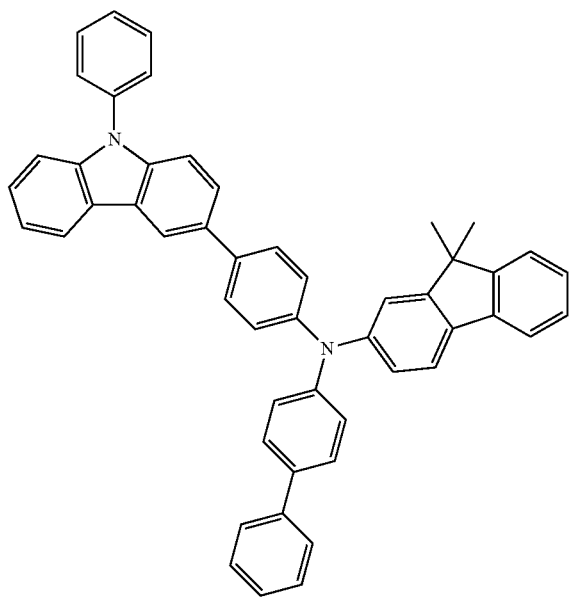
HT5
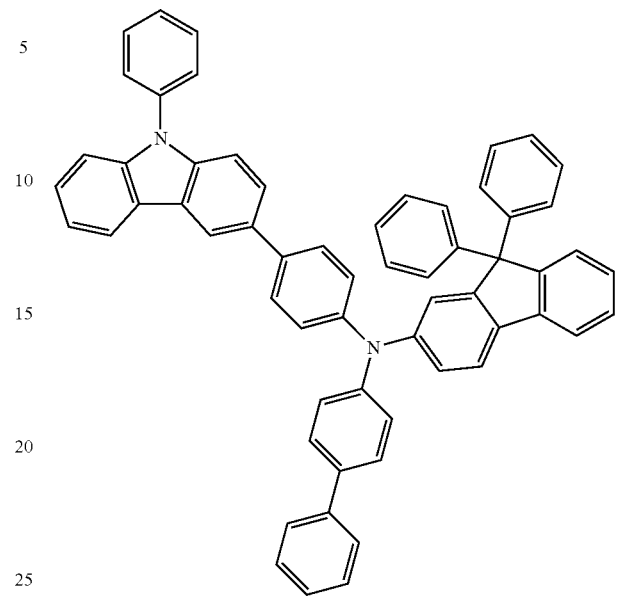
HT4
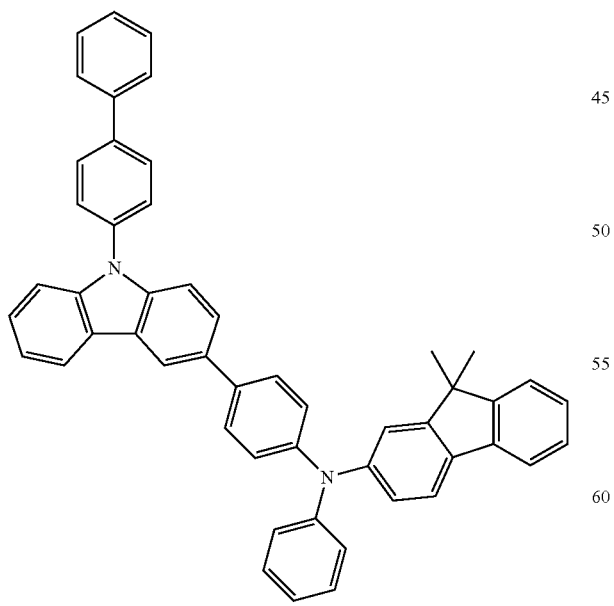
HT6

HT7
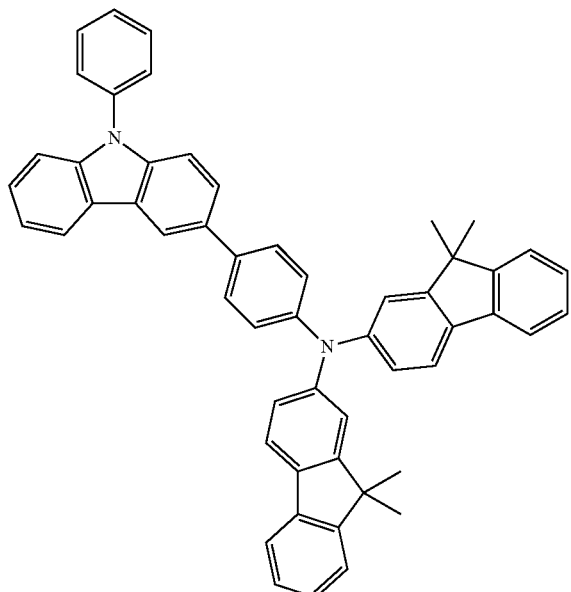
HT9
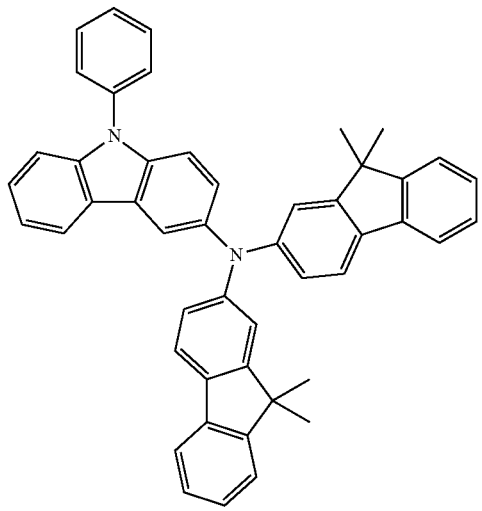
HT8
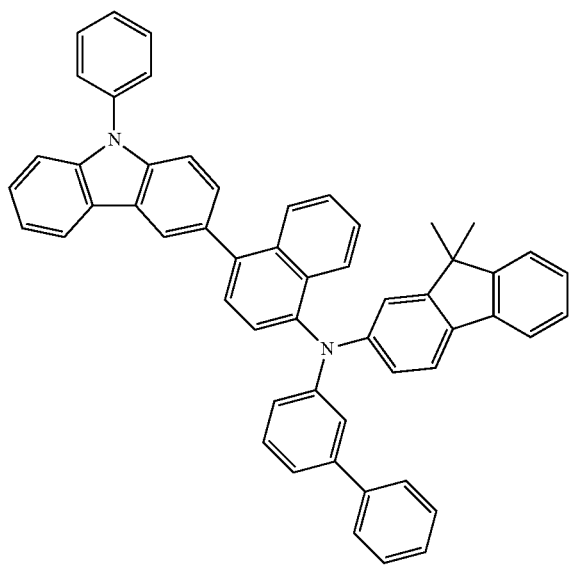
HT10
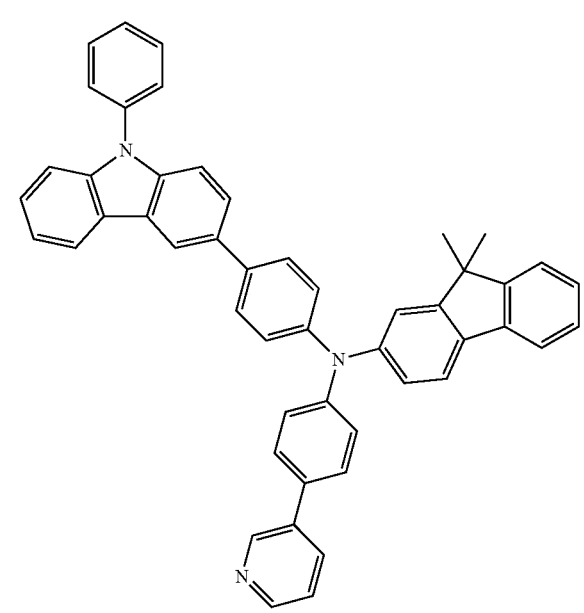

HT11
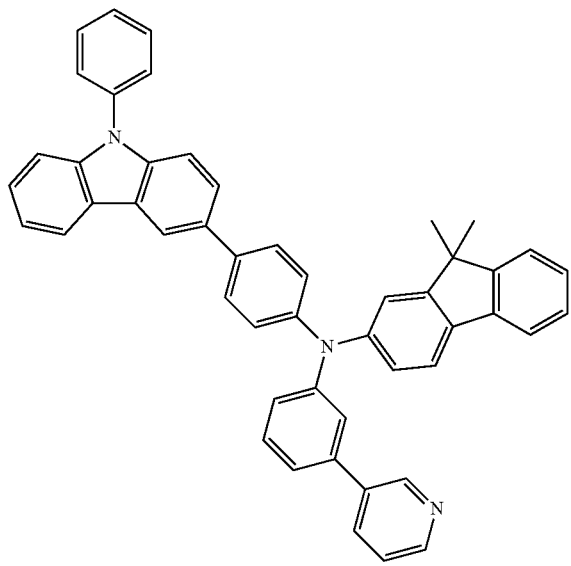
HT12
HT13
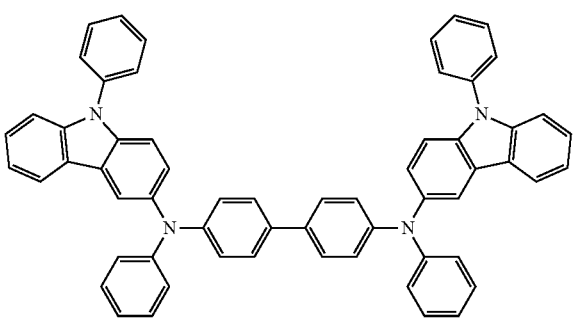
HT14
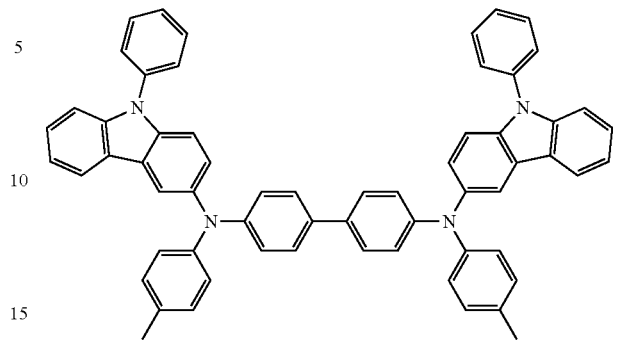
HT15
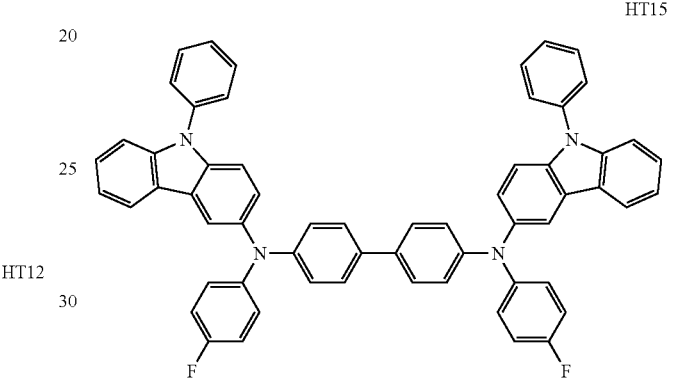
HT16
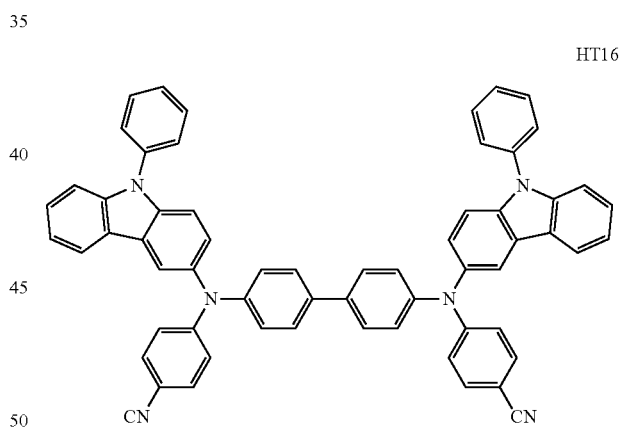
HT17

-continued

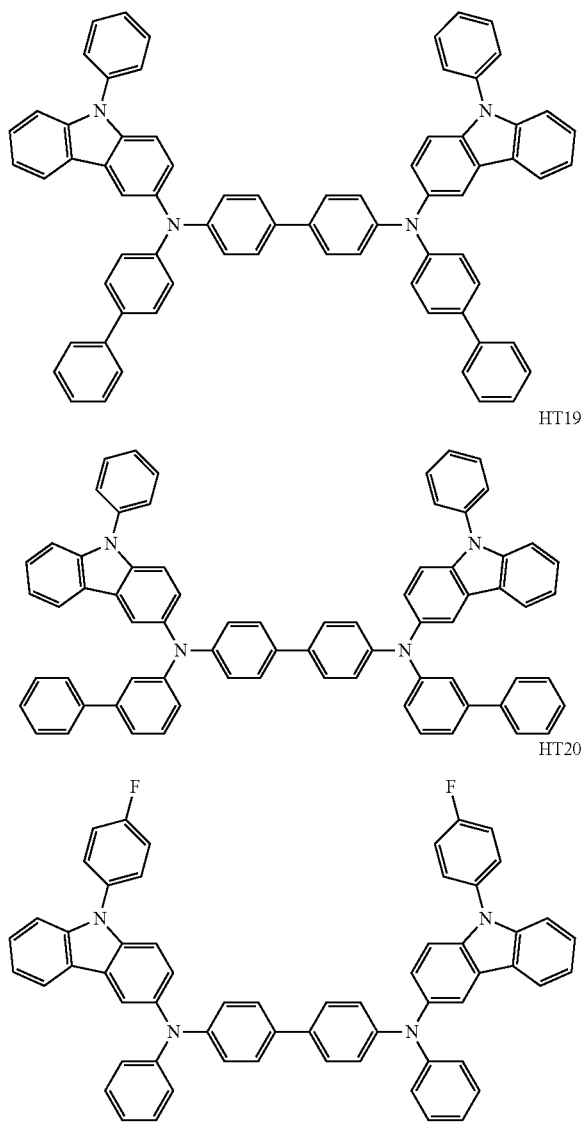

HT18

HT19

HT20

The thickness of the hole transport region may be from about 100 Å to about 10000 Å, and in some embodiments, from about 100 Å to about 1000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or inhomogeneously dispersed in the hole transport region.

The charge-generating material may be, for example, a p-dopant. The p-dopant may be one of quinine derivatives, metal oxides, and compounds with a cyano group, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and Compound HT-D1.

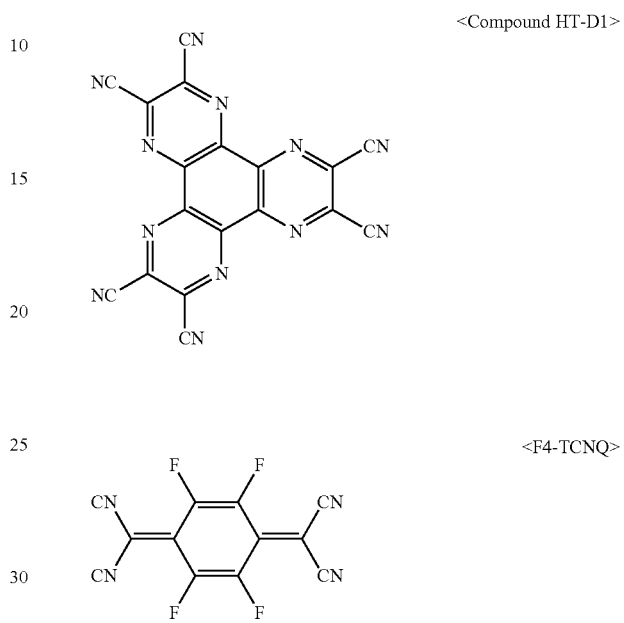

<Compound HT-D1>

<F4-TCNQ>

The hole transport region may further include at least one of a buffer layer and an EBL, in addition to the HIL and HTL described above. The buffer layer may compensate for an optical resonance distance of light according to a wavelength of the light emitted from the EML, and thus may improve light-emission efficiency. A material in the buffer layer may be any material used in the hole transport region. The EBL may block migration of electrons from the electron transport region into the EML.

The EML may be formed on the first electrode 110 or the hole transport region by using any of a variety of methods, for example, by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL, and accordingly will not be described in detail When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another, or a structure including a mixture of a red light-emitting material, a green light-emitting material, and a blue light-emitting material, and thus may emit white light.

The EML may include a host and a dopant.

The host may include at least one of TPBi, TBADN, AND (also referred to as "DNA"), CBP, CDBP, and TCP.

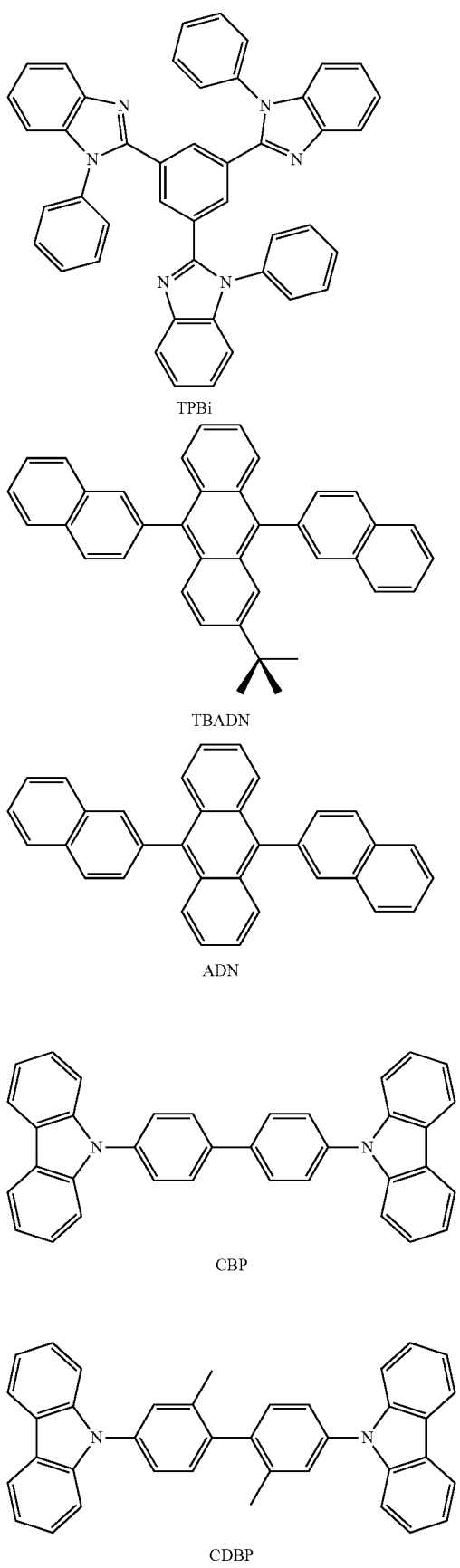

TPBi

TBADN

ADN

CBP

CDBP

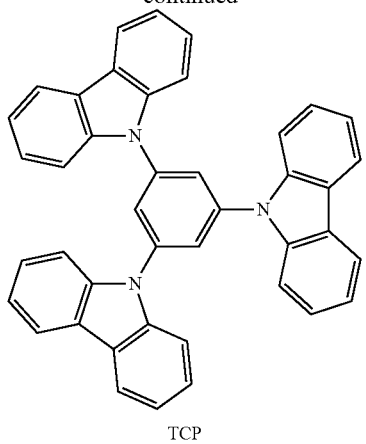

TCP

For example, the host may include a compounds represented by Formula 301.

$$Ar_{301}-[(L_{301})_{xb1}-R_{301}]_{xb2}$$  <Formula 301>

In Formula 301, $Ar_{301}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$aryloxy group, a $C_6$-$C_{60}$arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ may each independently be selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{301}$ may be defined the same as $L_{201}$ described herein, $R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, or a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

For example, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, $R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group. However, embodiments are not limited thereto.

For example, the host may include a compound represented by Formula 301A.

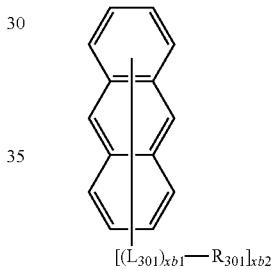

<Formula 301A>

Substituents $R_{301}$, $L_{301}$, Xb1, and xb2 in Formula 301A may be defined the same as those described herein.

The compound of Formula 301 may include at least one of compounds H1 to H42, but is not limited thereto.

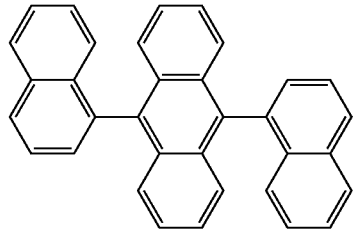

H1

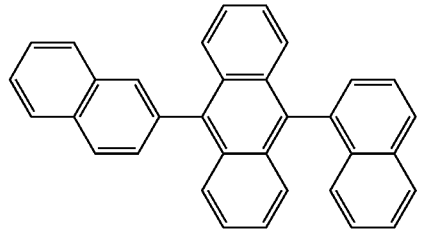

H2

75
-continued
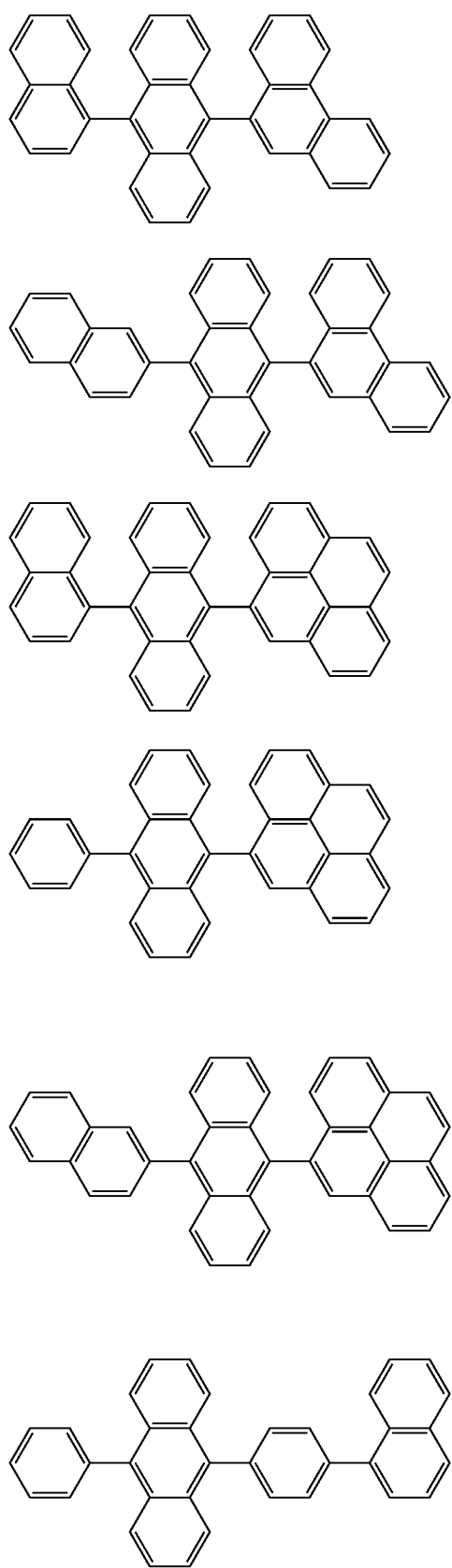
H3
H4
H5
H6
H7
H8
76
-continued
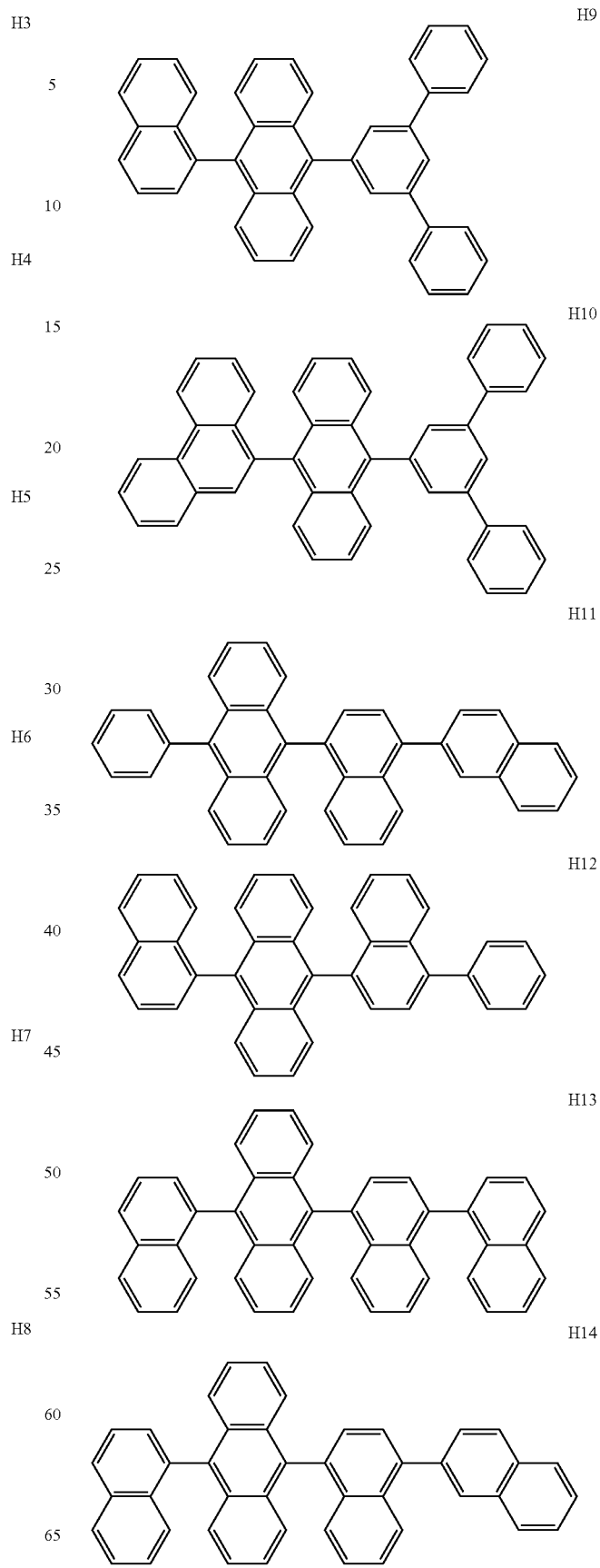
H9
H10
H11
H12
H13
H14

H15
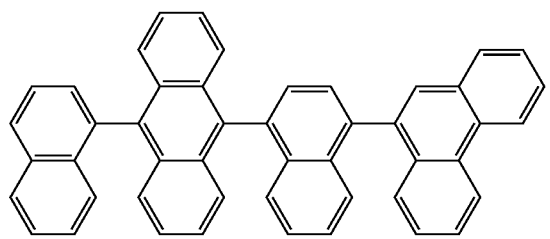
H16
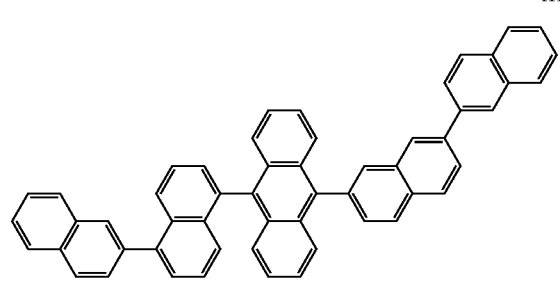
H17
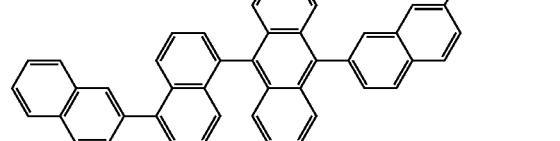
H18
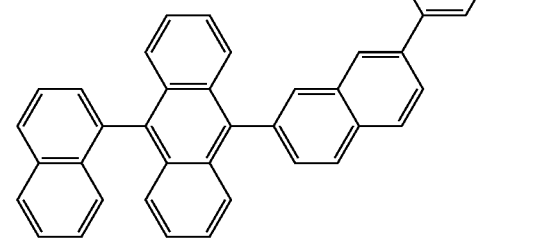
H19
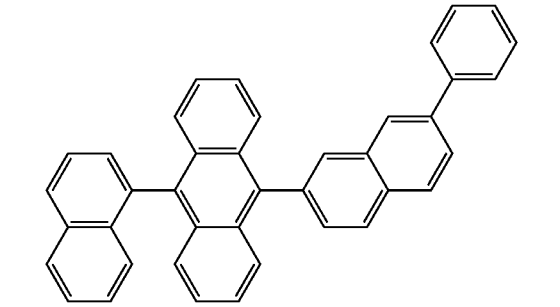
H20
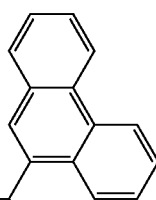
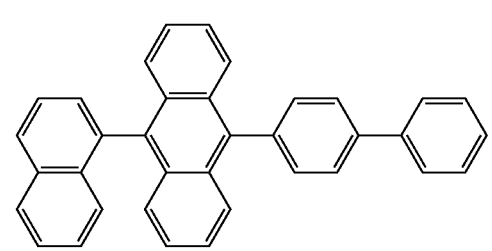
H21
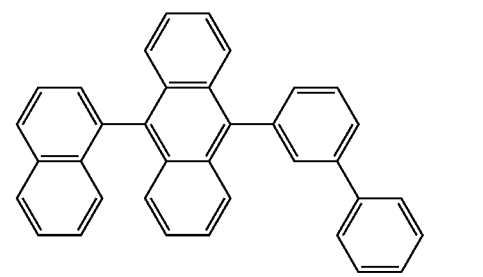
H22
H23
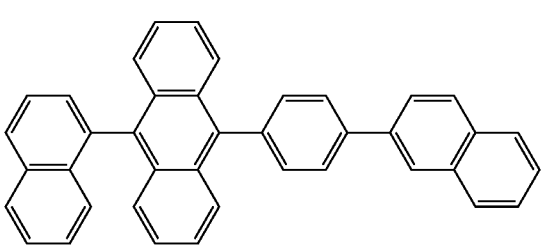
H24
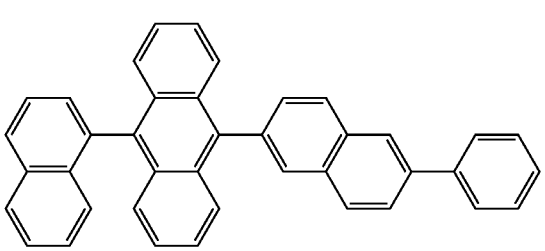

-continued
H25
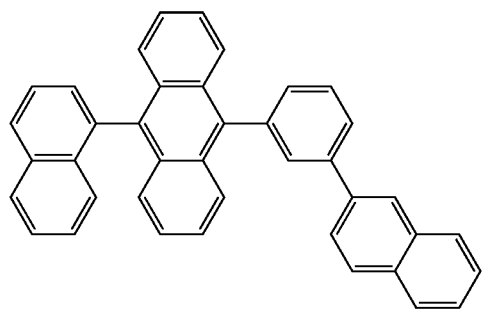
H26
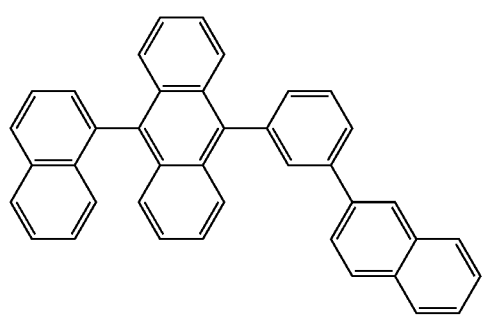
H27
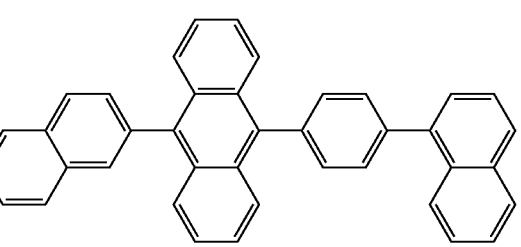
H28
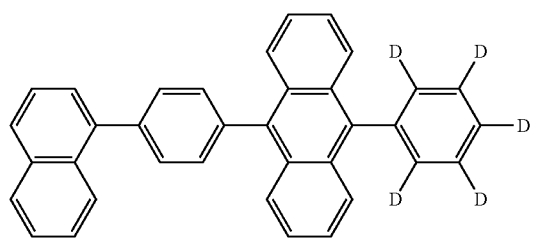
H29
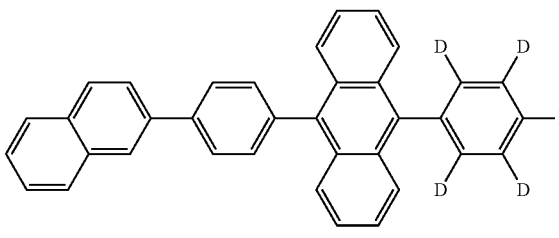
H30
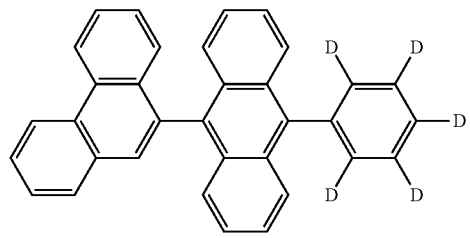
-continued
H31
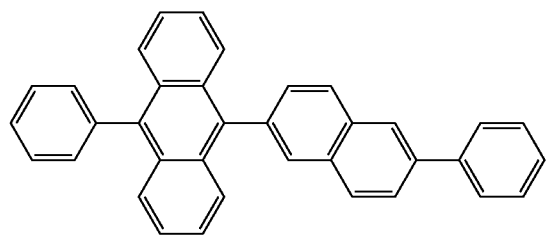
H32
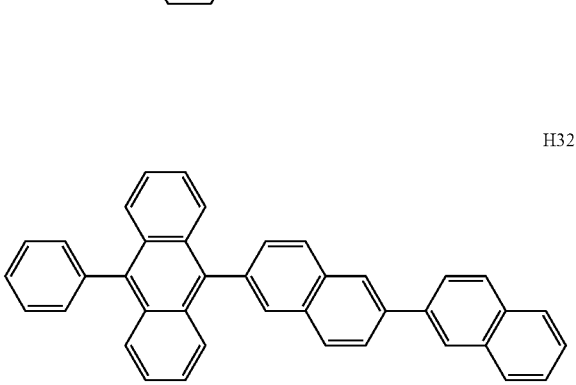
H33
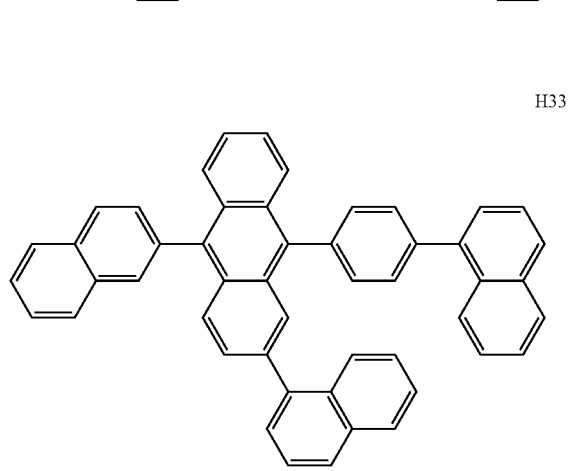
H34
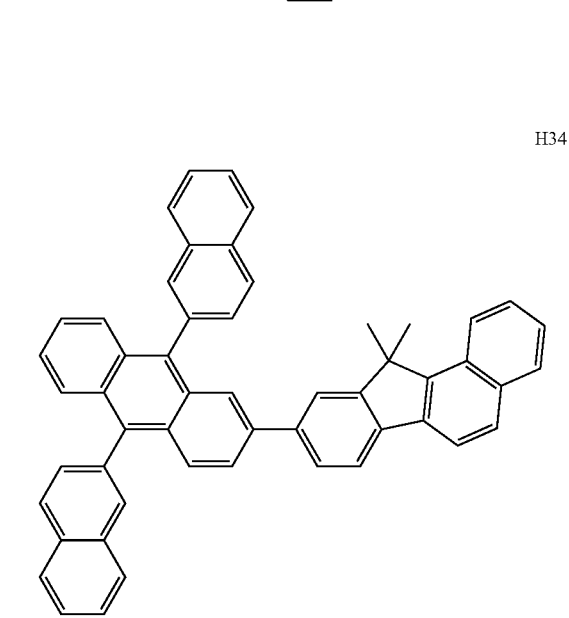

-continued
H35 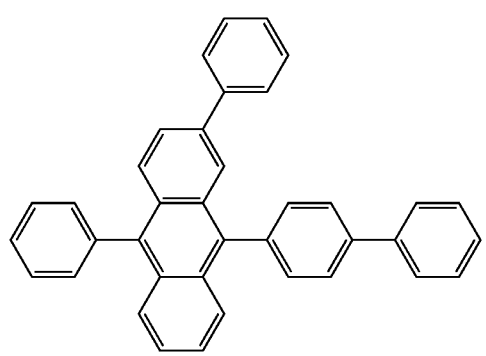
H36 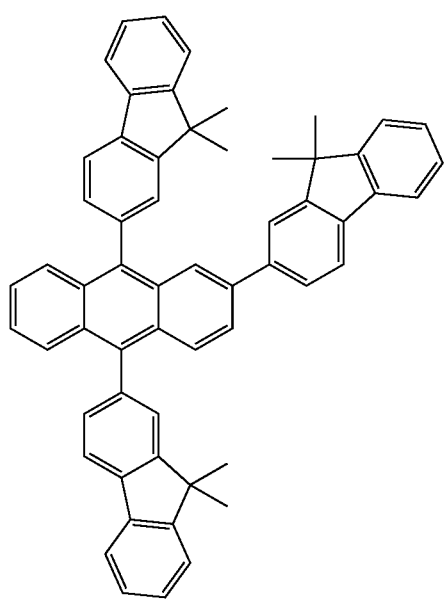
H37 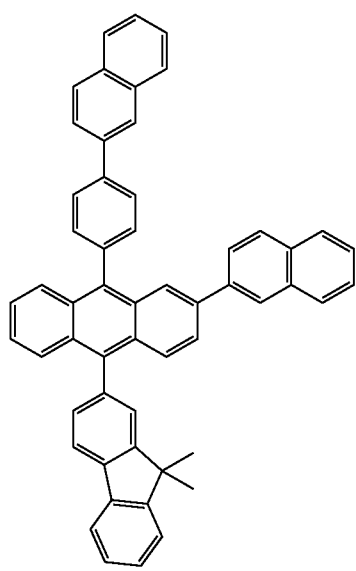
-continued
H38 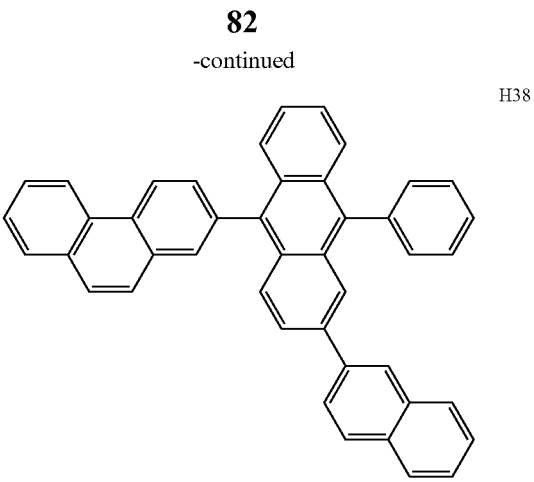
H39 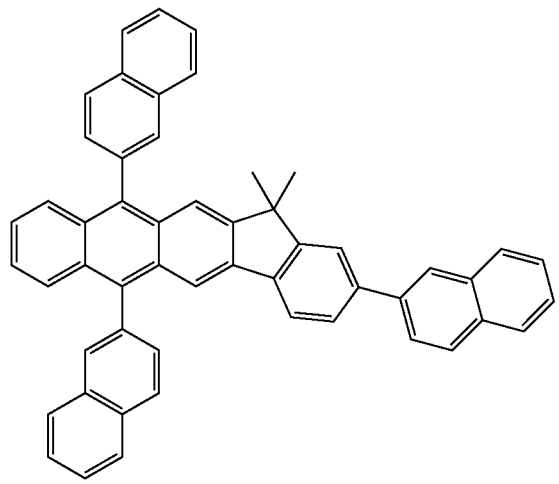
H40 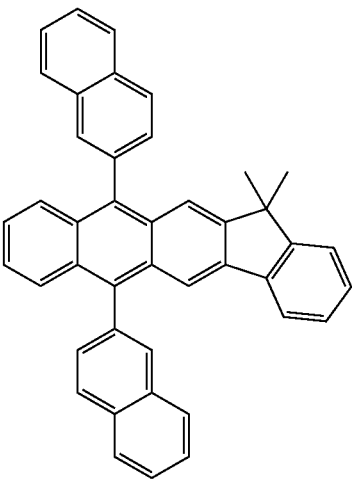

H41
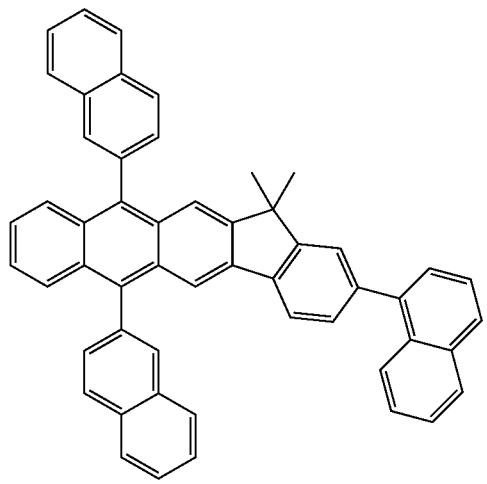
H42
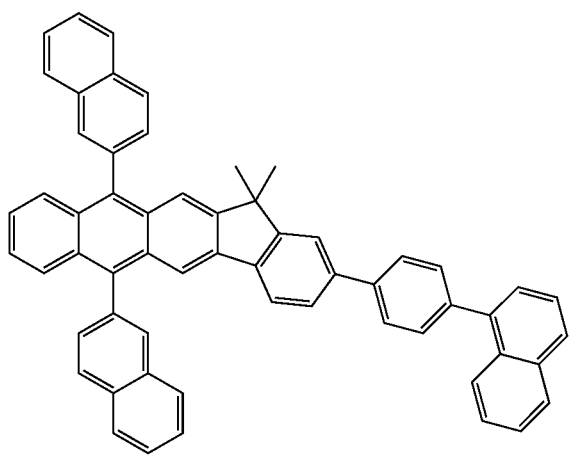
For example, the host may include at least one of compounds H43 to H49. However, embodiments are not limited thereto.
H43
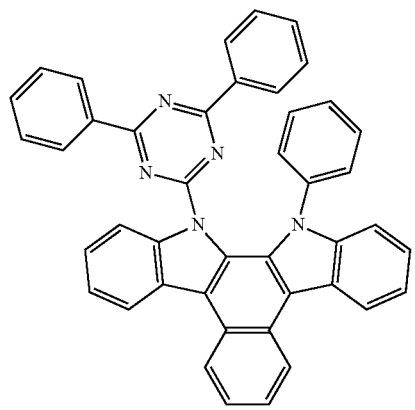
H44
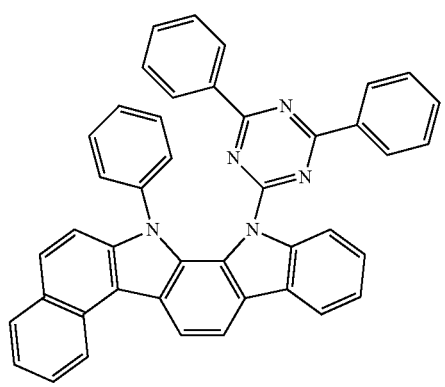
H45
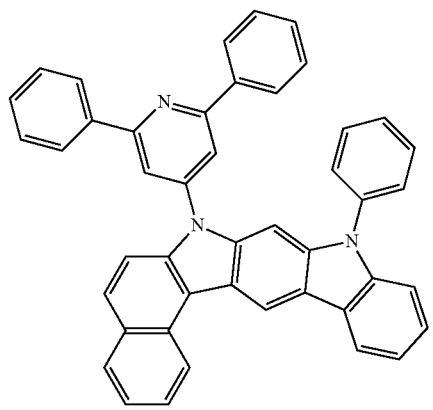
H46

-continued

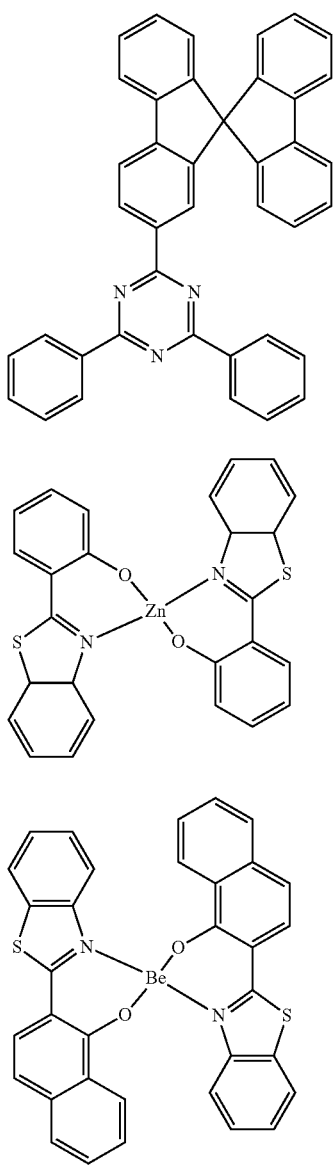

H47

H48

H49

The dopant may include at least one of a fluorescent dopant and a phosphorescent dopant.

The phosphorescent dopant may include an organometallic complex represented by Formula 401.

<Formula 401>

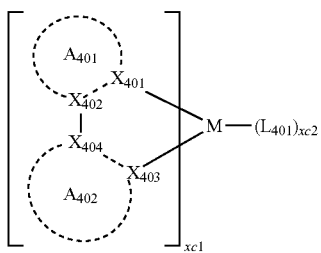

In Formula 401,

M may iridium (Ir), platinum (Pt), osmium (Os), titanium (Ti), zirconium (Zr), hafnium (Hf), europium (Eu), terbium (Tb), or thulium (Tm);

$X_{401}$ to $X_{404}$ may each independently be a nitrogen or a carbon;

rings $A_{401}$ and $A_{402}$ may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted a dibenzofuran, and a substituted or unsubstituted a dibenzothiophene;

at least one of substituents of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$), and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be 1, 2, or 3;

xc2 may be 0, 1, 2, or 3.

The $Q_{401}$ to $Q_{407}$, $Q_{411}$ to $Q_{417}$ and $Q_{421}$ to $Q_{427}$ may each independently be selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group.

For example, in Formula 401, $L_{401}$ may be a monovalent, divalent, or trivalent organic ligand. For example, $L_{401}$ in Formula 401 may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorous ligand (for example, phosphine or phosphite). However, embodiments are not limited thereto.

When $A_{401}$ in Formula 401 has at least two substituent groups, the at least two substituent groups of $A_{401}$ may be linked to each other to form a saturated or unsaturated ring.

When $A_{402}$ in Formula 401 has at least two substituents groups, the at least two substituent groups of $A_{402}$ 2 may be linked to each other to form a saturated or unsaturated ring.

When xc1 in Formula 401 is 2 or greater, a plurality of ligands

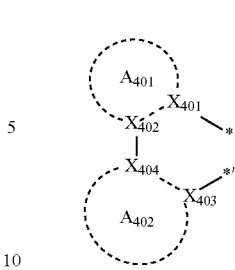

in Formula 401 may be identical to or different from each other. When xc1 in Formula 1 is 2 or greater, $A_{401}$ and $A_{402}$ may be linked to $A_{401}$ and $A_{402}$ of another adjacent ligand, respectively, directly or via a linking group (for example, a $C_1$-$C_5$ alkylene group, —N(R')— (where R' is a $C_1$-$C_{10}$ alkyl group or a $C_6$-$C_{20}$ aryl group), or C(=O)—).

The phosphorescent dopant may include at least one of Compounds PD1 to PD74, but is not limited thereto.

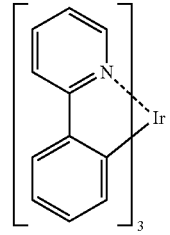

PD1

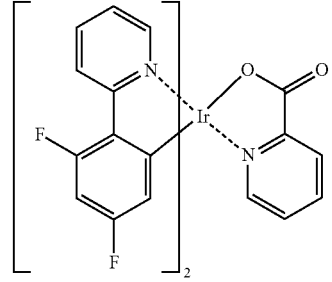

PD2

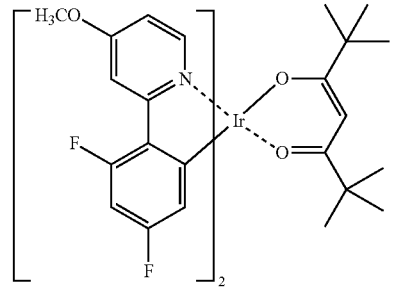

PD3

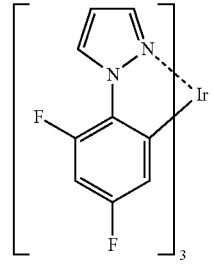

PD4

PD5 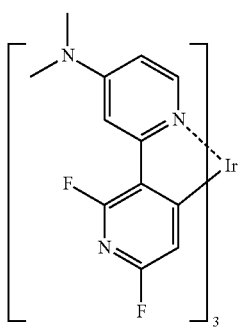
PD6 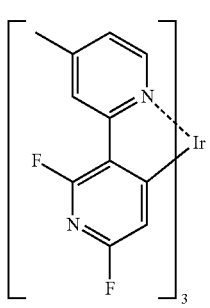
PD7 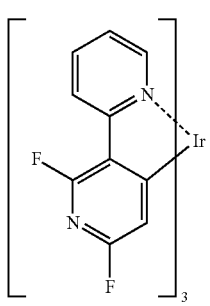
PD8 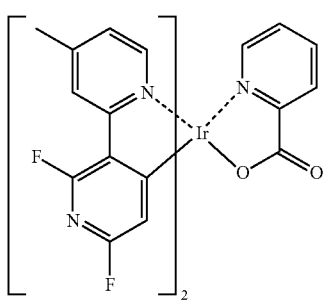
PD9 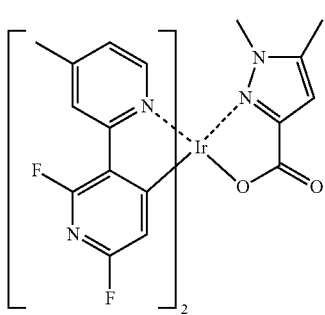
PD10 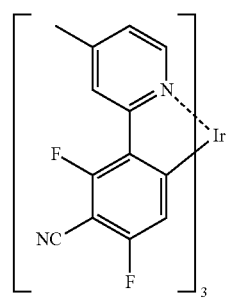
PD11 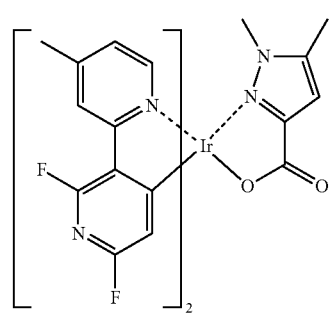
PD12 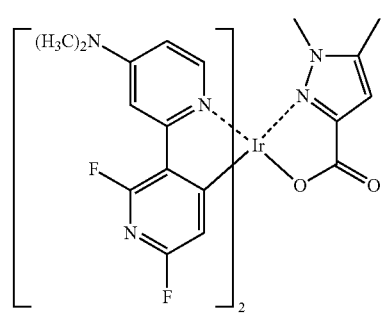
PD13 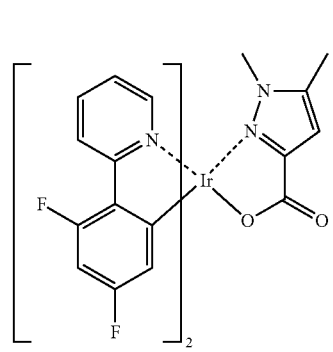
PD14 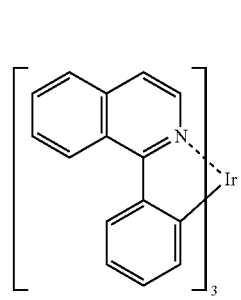

-continued
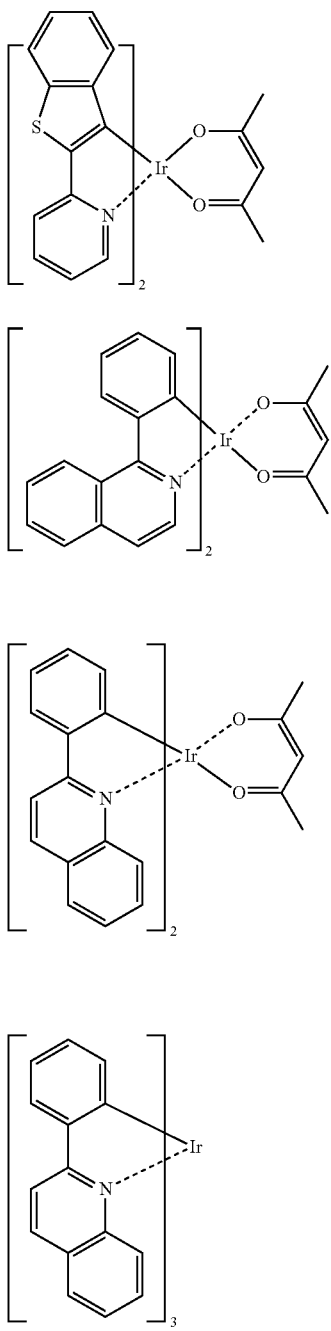
PD15
PD16
PD17
PD18
PD19
-continued
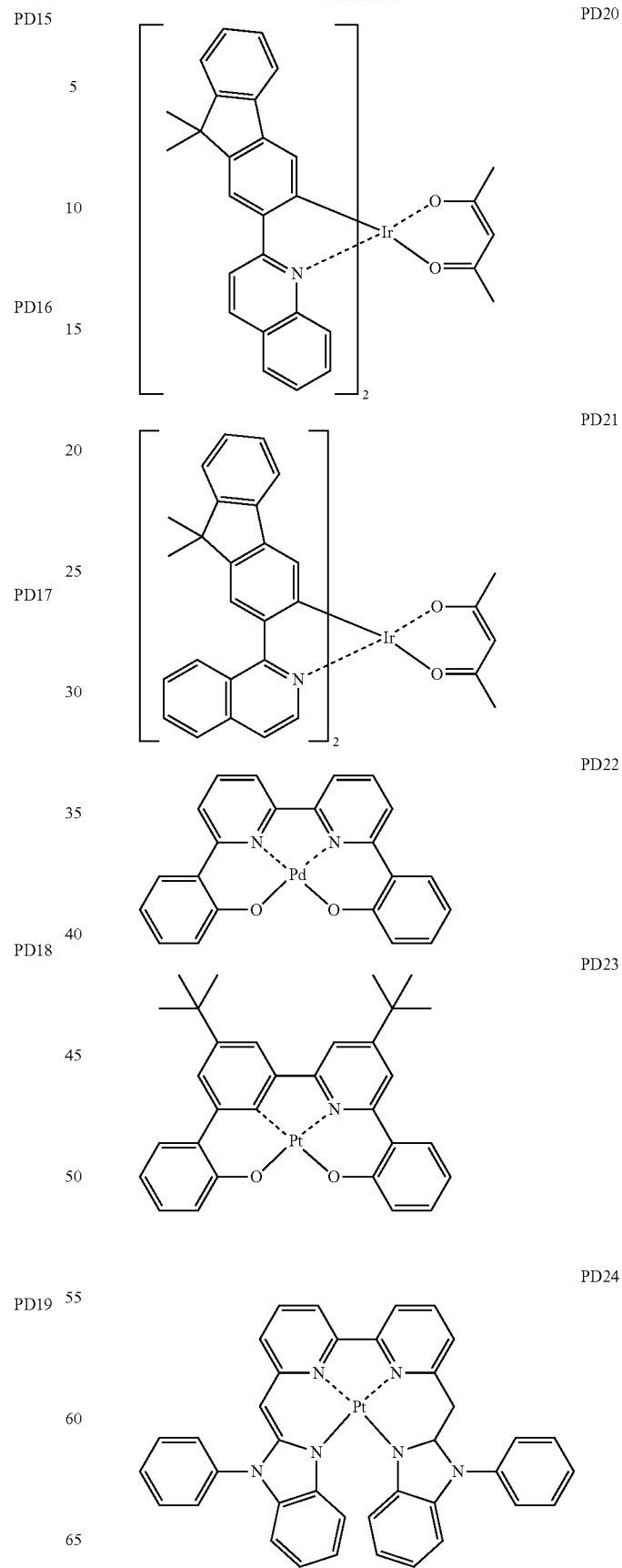
PD20
PD21
PD22
PD23
PD24

-continued
PD25
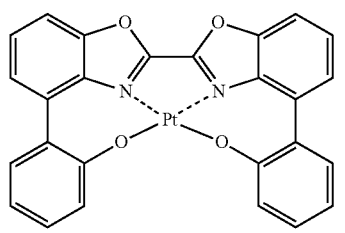
PD26
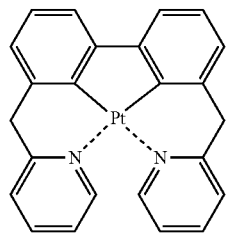
PD27
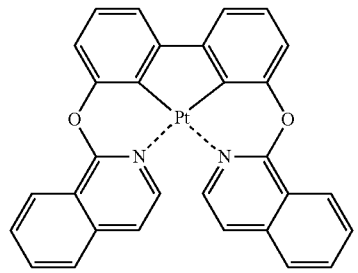
PD28
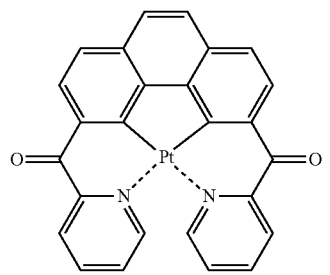
PD29
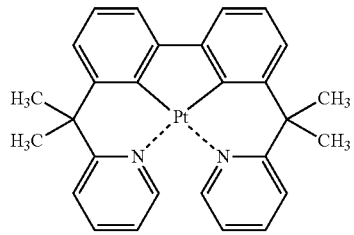
PD30
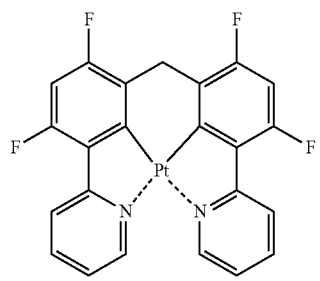
-continued
PD31
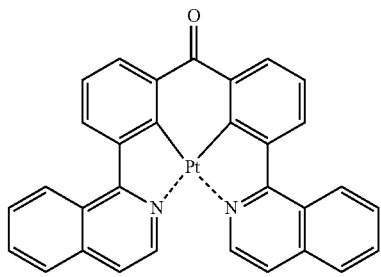
PD32
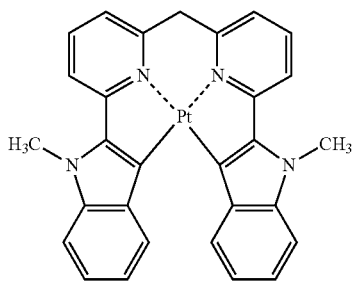
PD33
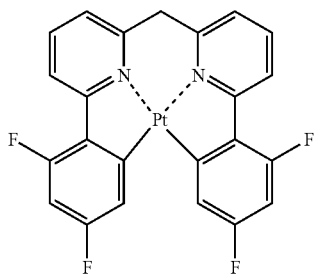
PD34
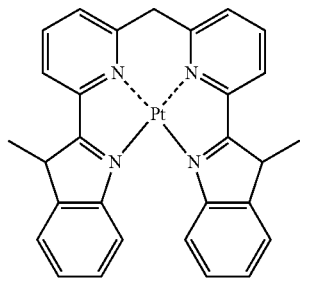
PD35
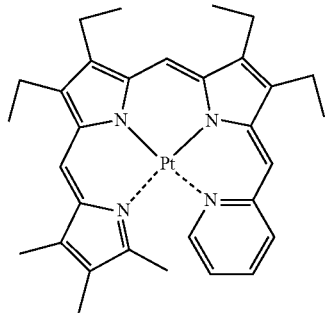

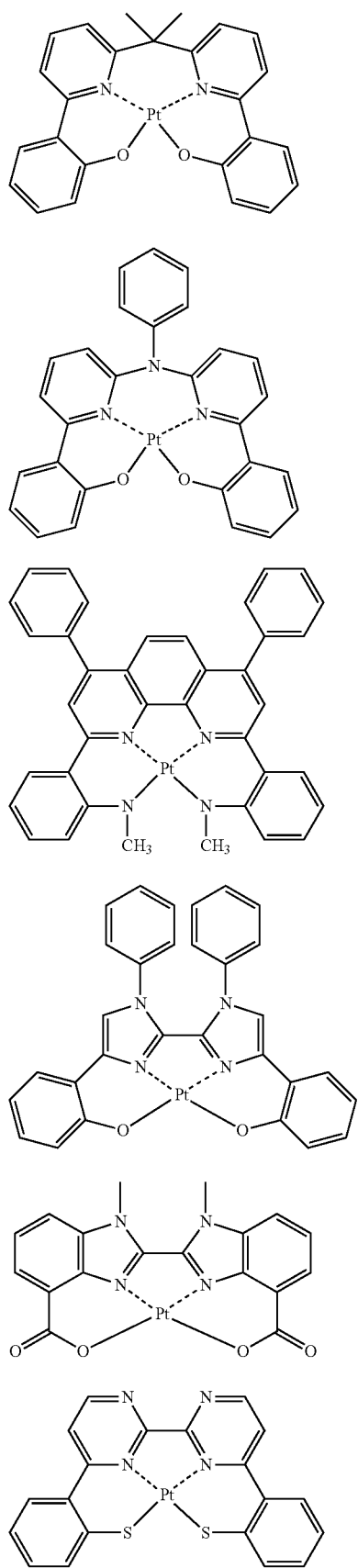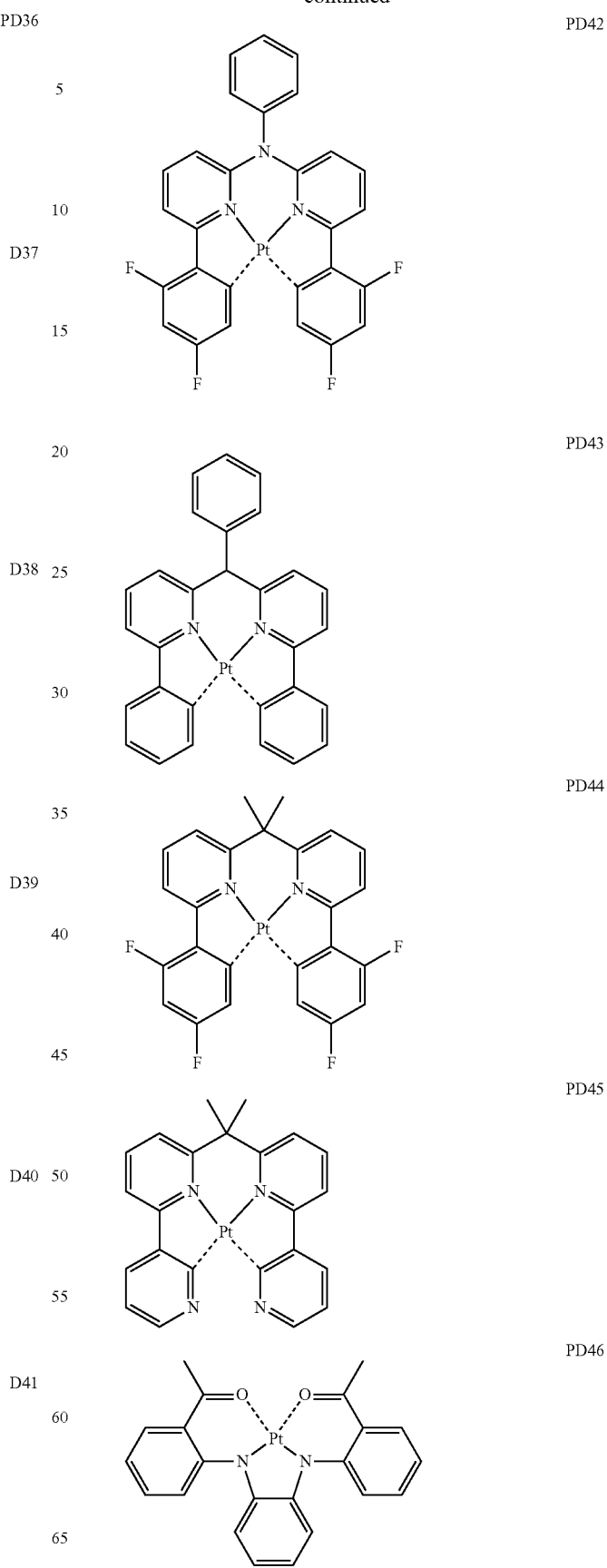

PD47
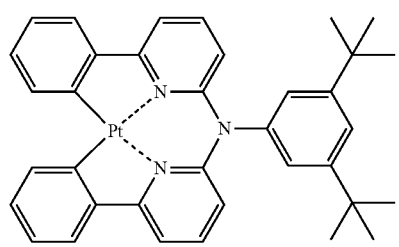
PD48
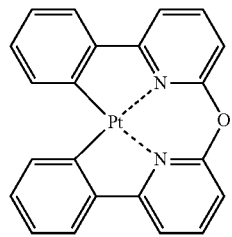
PD49
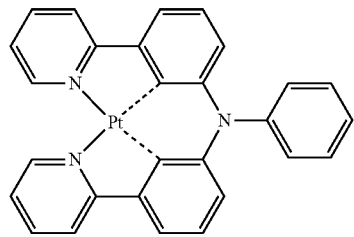
PD50
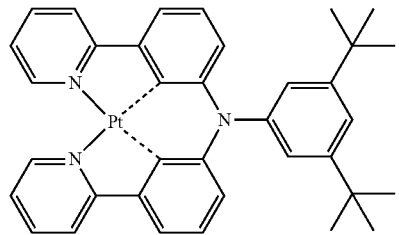
PD51
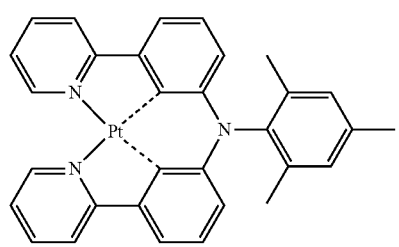
PD52
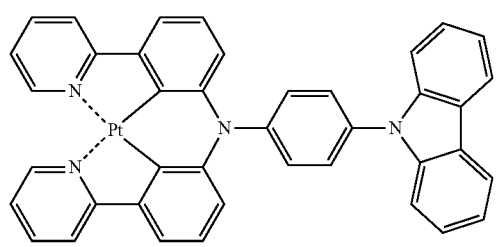
PD53
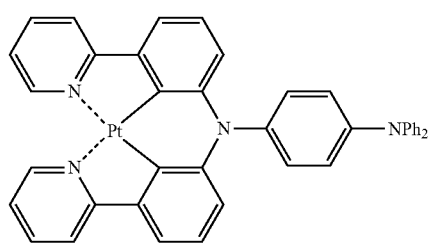
PD54
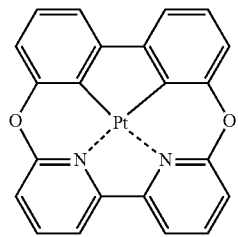
PD55
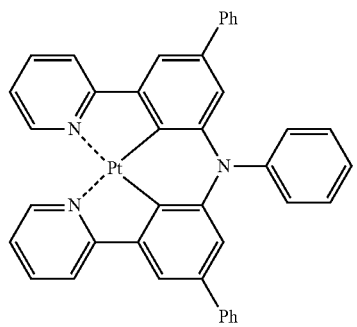
PD56
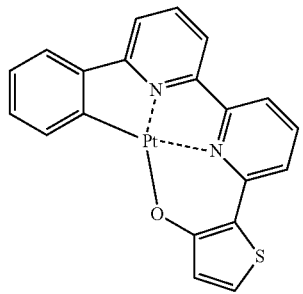
PD57
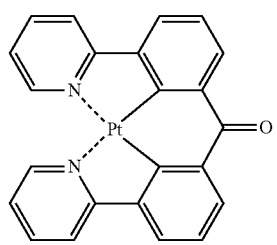

PD58
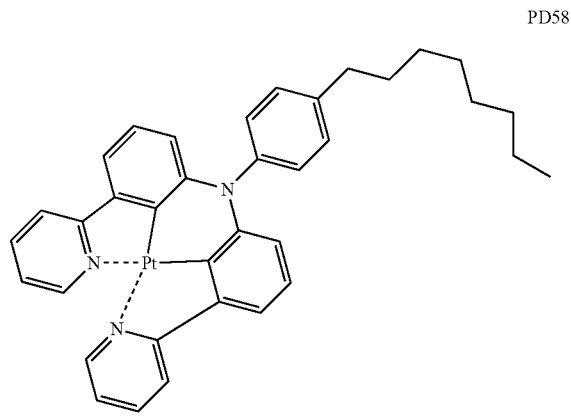
PD59
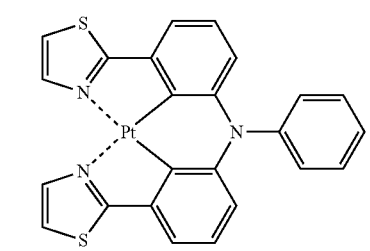
PD60
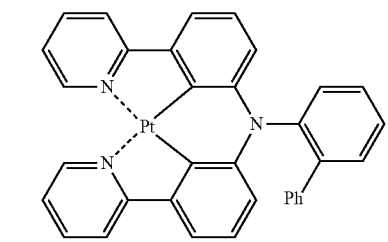
PD61
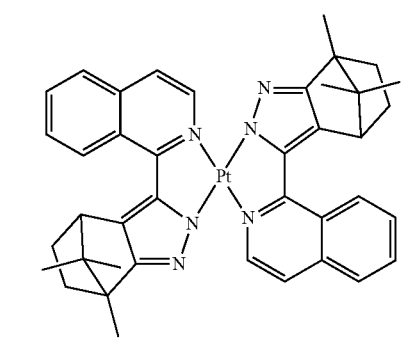
PD62
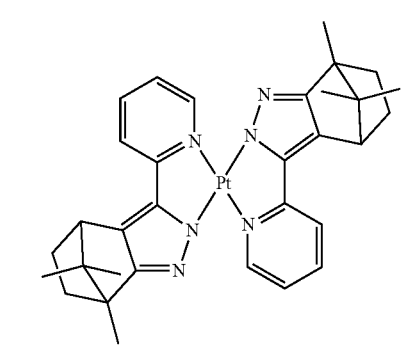
PD63
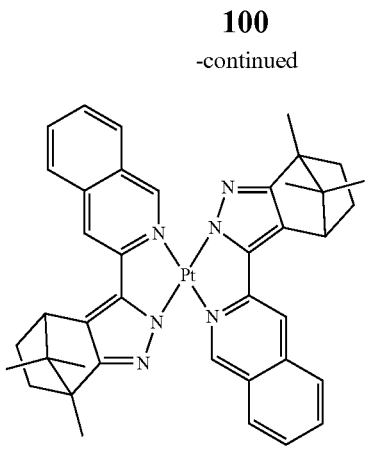
PD64
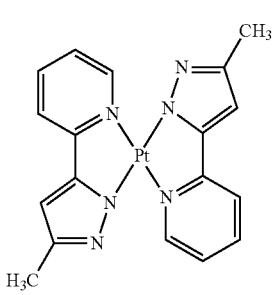
PD65
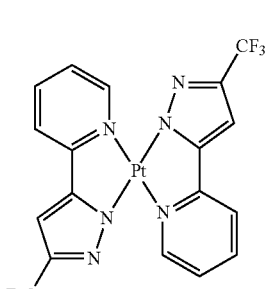
PD66
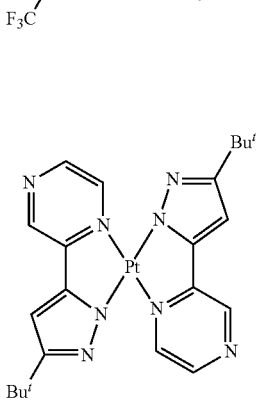
PD67
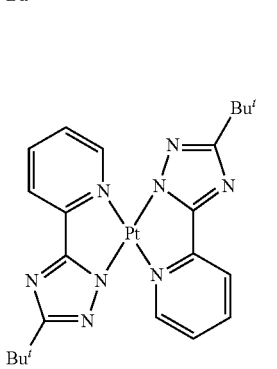

PD68
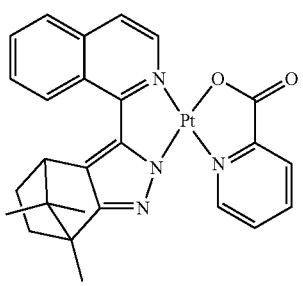
PD69
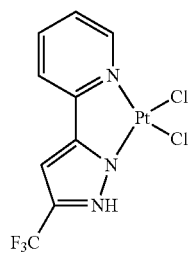
PD70
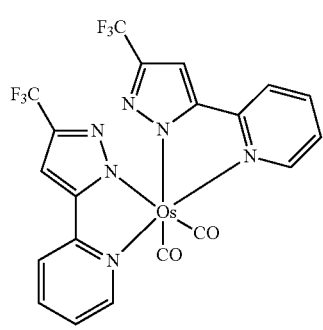
PD71
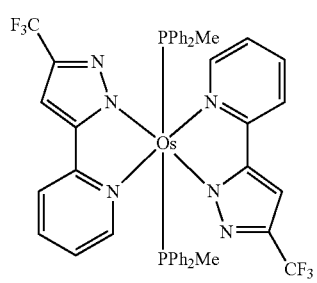
PD72
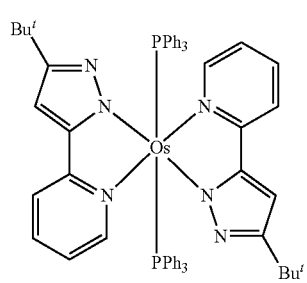
PD73
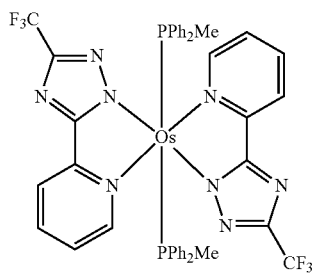
PD74
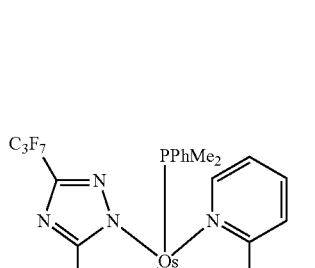
For example, the phosphorescent dopant may include PtOEP:
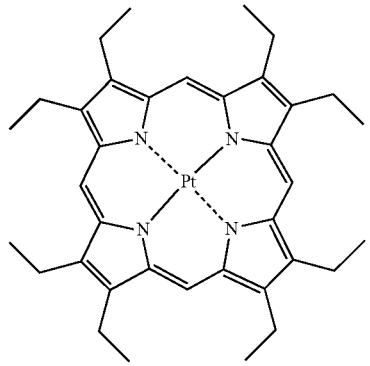
PtOEP
For example, the fluorescent dopant may further include at least one of DPAVBi, BDAVBi, TBPe, DCM, DCJTB, Coumarin 6, and C545T.

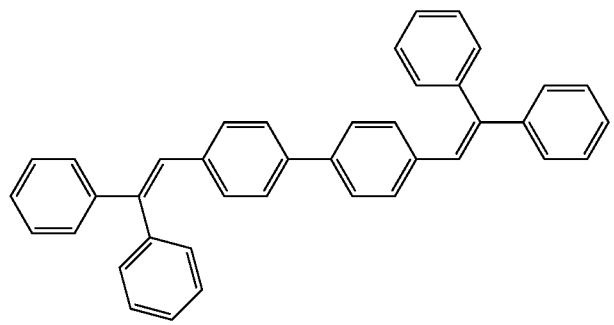
DPVBi
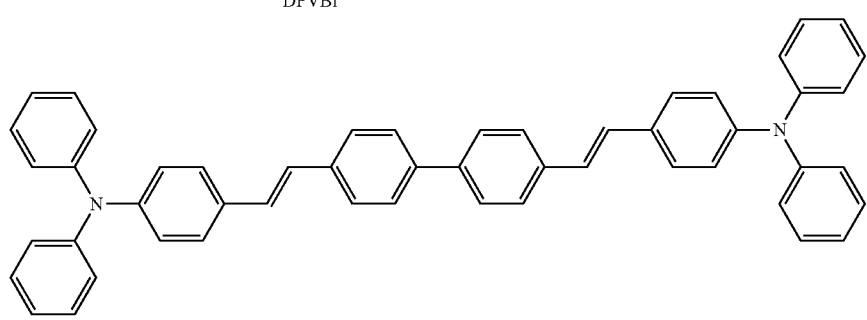
DPAVBi
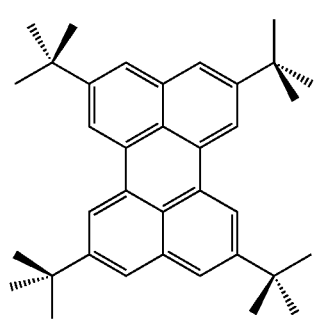
TBPe
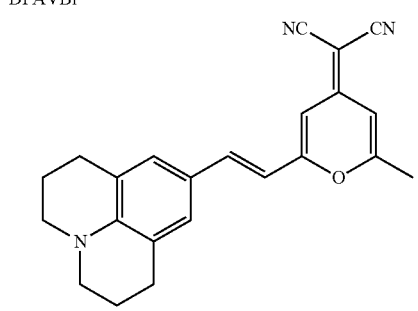
DCM
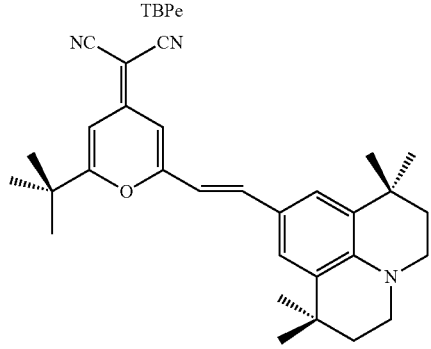
DCJTB
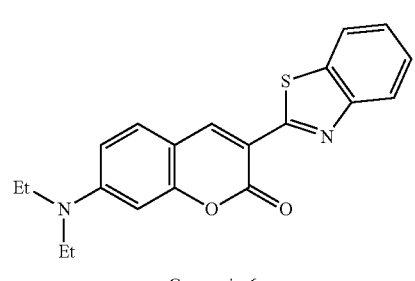
Coumarin 6
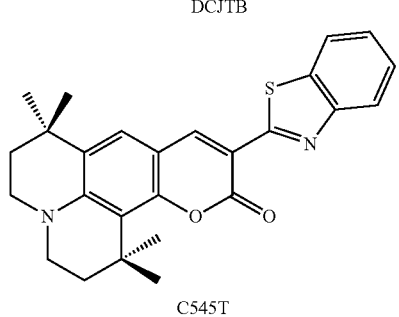
C545T For example, the fluorescent dopant may include a compound represented by Formula 501.

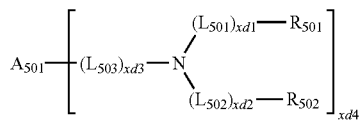
<Formula 501>

In Formula 501,

Ar$_{501}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$), wherein $Q_{501}$ to $Q_{503}$ may each independently be selected from a hydrogen, $C_1$-$C_{60}$alkyl group, a $C_2$-$C_{60}$alkenyl group, a $C_6$-$C_{60}$ aryl group, and a $C_1$-$C_{60}$ heteroaryl group;

L$_{501}$ to L$_{503}$ may be the same as those for L$_{201}$ defined herein;

R$_{501}$ and R$_{502}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazoly group, a triazinyl group, a dibenzofuranyl group, and a dibenzothio group, and a phenyl group, a naphthyl group, a fluorenyl group, spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothio group, each substituted with at least one selected from a phenyl group, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group;

xd1 to xd3 may each independently be selected from 0, 1, 2, and 3; and xb4 may be selected from 1, 2, 3, and 4.

For example, the fluorescent host may include at least one of Compounds FD1 to FD9.

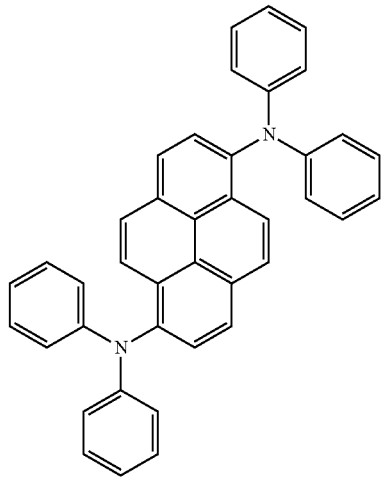
FD1

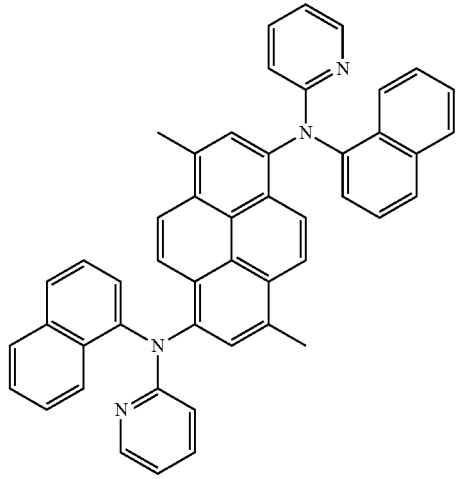
FD2

-continued
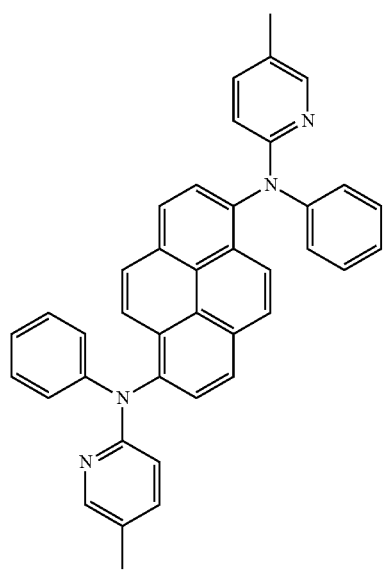
FD3
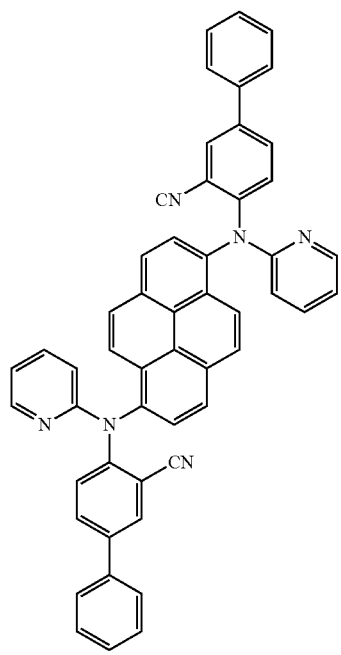
FD4
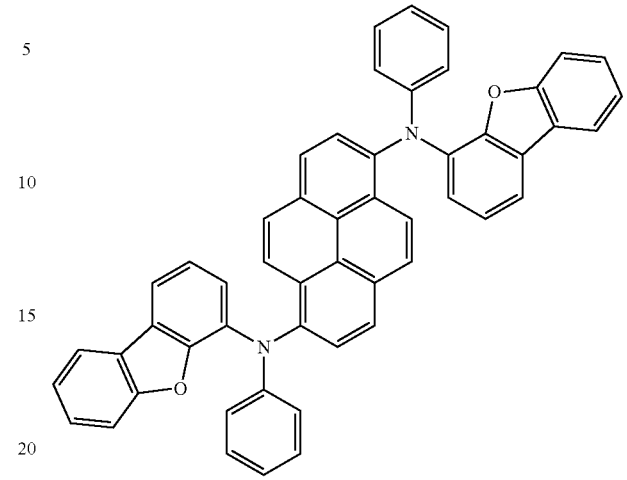
FD5
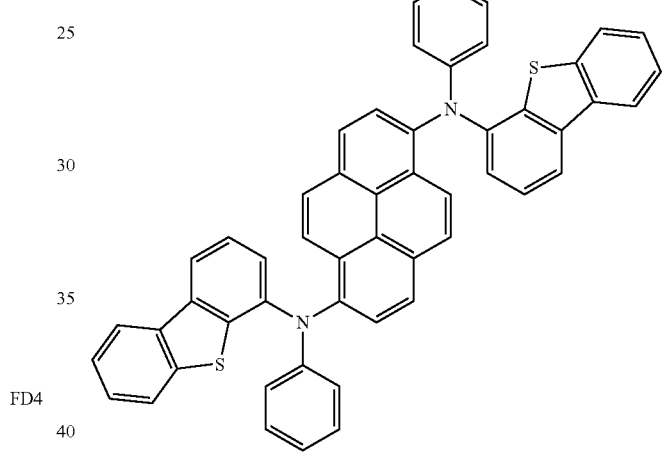
FD6
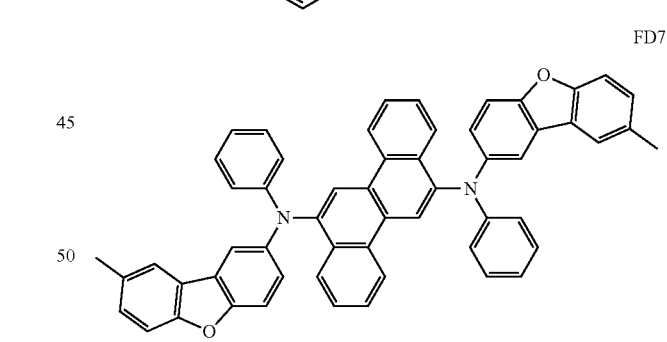
FD7
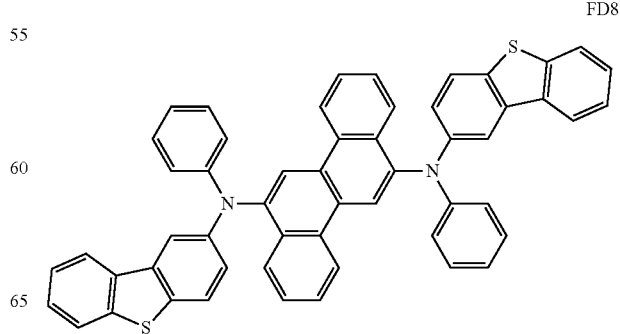
FD8

<Compound FD9>

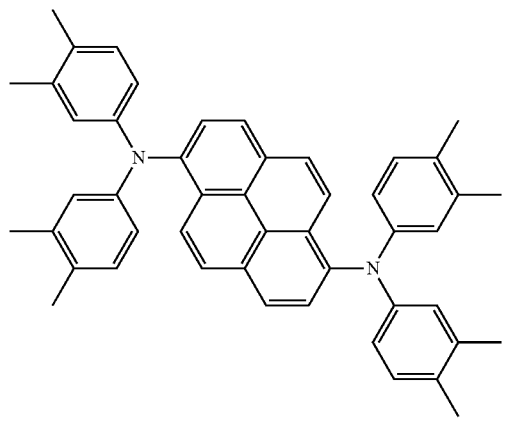

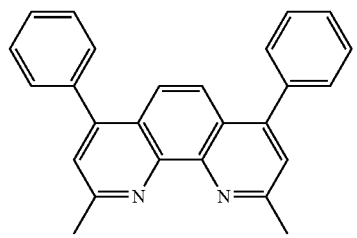

BCP

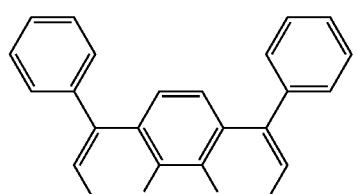

Bphen

The amount of the dopant in the EML may be from about 0.01 parts to about 15 parts by weight based on 100 parts by weight of the host, but is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

Next, the electron transport region may be disposed on the EML.

The electron transport region may include at least one of a HBL, an ETL, and an EIL. However, embodiments are not limited thereto.

In some embodiments, the electron transport region may have a structure including an ETL/EIL, or a HBL/ETL/EIL, wherein the layers forming a structure of the electron transport region may be sequentially stacked on the EML in the order stated above. However, embodiments are not limited thereto:

In some embodiments, the organic layer 150 of the organic light-emitting device 10 may include the electron transport region between the EML and the second electrode 190, and at least one of the condensed cyclic compounds of Formulae 1A and 1B may be in the electron transport region.

The electron transport region may include a HBL. When the EML includes a phosphorescent dopant, the HBL may prevent diffusion of triplet excitons or holes into the ETL from the EML.

When the electron transport region includes a HBL, the HBL may be formed on the EML by using any of a variety of methods, for example, by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL, and accordingly will not be described in detail.

For example, the HBL may include at least one of BCP below and Bphen below. However, embodiments are not limited thereto.

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The electron transport region may include an ETL. The ETL may be formed on the EML or the HBL by using any of a variety of methods, for example, by using vacuum deposition, spin coating, casting, Langmuir-Blodgett (LB) deposition, inkjet printing, laser printing, laser induced thermal imaging (LITI), or the like. When the ETL is formed using vacuum deposition or spin coating, the deposition and coating conditions for forming the ETL may be similar to the above-described deposition and coating conditions for forming the HIL, and accordingly will not be described in detail.

In some embodiments, the organic layer 150 of the organic light-emitting device may include an electron transport region between the EML and the second electrode 190, wherein the electron transport region may include an ETL, and the ETL may include at least one of the condensed cyclic compounds of Formula 1.

The ETL may further include at least one of BCP, Bphen Alq$_3$, Balq, TAZ, and NTAZ, in addition to at least one of the condensed cyclic compounds of Formula 1.

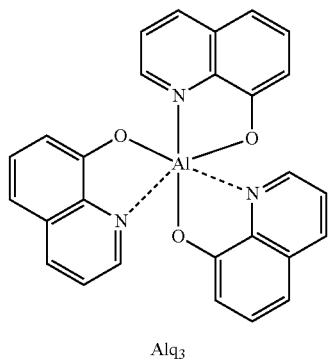

Alq$_3$

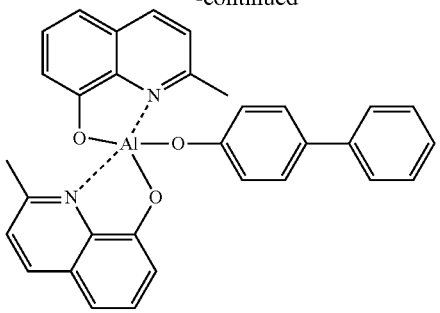

BAlq

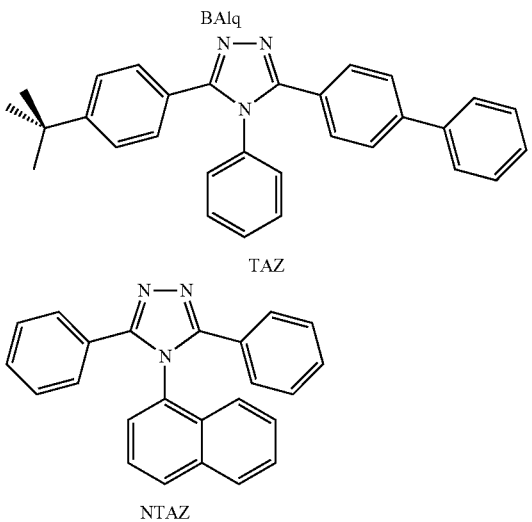

TAZ

NTAZ

The thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 below (lithium quinolate (LiQ)), or compound ET-D2.

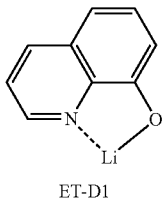

ET-D1

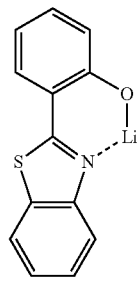

ET-D2

The electron transport region may include an EIL that may facilitate injection of electrons from the second electrode 190.

The EIL may be formed on the ETL by using any of a variety of methods, for example, by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL, and accordingly will not be described in detail.

The EIL may include at least one selected from LiF, NaCl, CsF, $Li_2O$, BaO, and LiQ.

A thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 are lithium (Li), magnesium (Mg), aluminum (Al), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a reflective electrode, a semi-transmissive electrode, or a transmissive electrode.

Although the organic light-emitting device of FIG. 1 is described above, embodiments are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a hydrocarbon group including at least one carbon double bond in the middle or terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a hydrocarbon group including at least one carbon triple bond in the middle or terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_1$-$C_{10}$ heterocycloalkyl group refers to a monovalent monocyclic group having 1 to 10 carbon atoms in which at least one hetero atom selected from N, O, P, and S is included as a ring-forming atom (ring member atom). Non-limiting examples of the $C_1$-$C_{10}$ heterocycloalkyl group are a tetrahydrofuranyl group and a tetrahydrothiophenyl group. A $C_1$-$C_{10}$ heterocycloalkylene group refers to a divalent group having the same structure as the $C_1$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_1$-$C_{10}$ heterocycloalkenyl group used herein refers to a monovalent monocyclic group having 1 to 10 carbon atoms that includes at least one double bond in the ring and in which at least one hetero atom selected from N, O, P, and S is included as a ring-forming atom. Non-limiting examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_1$-$C_{60}$ heteroaryl group refers to a monovalent, aromatic carbocyclic aromatic group having 1 to 60 carbon atoms in which at least one hetero atom selected from N, O, P, and S is included as a ring-forming atom, and 1 to 60 carbon atoms. A $C_1$-$C_{60}$ heteroarylene group refers to a divalent, aromatic carbocyclic group having 1 to 60 carbon atoms in which at least one hetero atom selected from N, O, P, and S is included as a ring-forming atom. Non-limiting examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl and the $C_1$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms and the entire molecule has non-aromaticity. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which carbon atoms (for example, 1 to 60 carbon atoms) and a hetero atom selected from N, O, P, and S are as ring-forming atoms and the entire molecule has non-aromaticity. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

As used herein, at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed cyclic group, the substituted divalent non-aromatic hetero-condensed cyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic hetero-condensed polycyclic group, may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{20}$ heterocycloalkenylene group, the substituted $C_6$-$C_{60}$ heteroarylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$), a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), or —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovarenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The acronym "Ph" used herein refers to phenyl, the acronym "Me" used herein refers to methyl, the acronym "Et" used herein refers to ethyl, and the acronym "ter-Bu" or "Bu$^t$" used herein refers to tert-butyl.

One or more embodiments, which include condensed cyclic compounds, and organic light-emitting devices including the same, will now be described in detail with reference to the following examples. However, these examples are only for illustrative purposes and are not intended to limit the scope of the one or more embodiments. In the following synthesis example, the expression that "'B' instead of 'A' was used" means that the amounts of 'B' and 'A' were the same in equivalent amounts.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 3: Synthesis of Compound 2

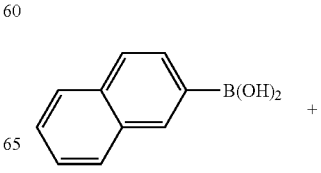

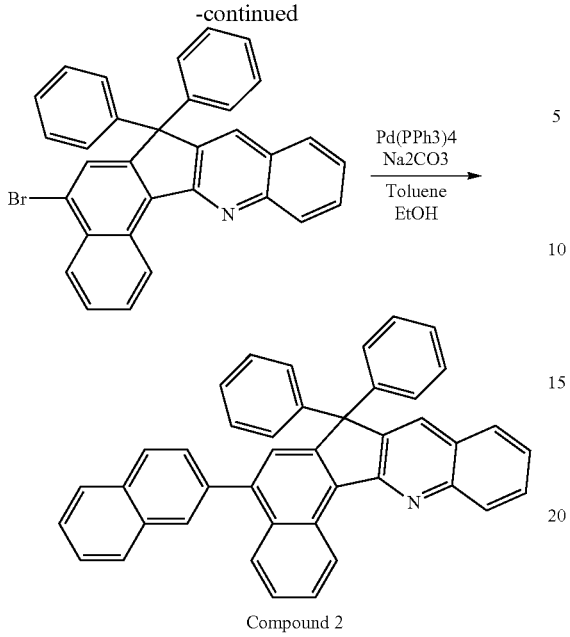

Compound 2

0.67 g (1 eq, 1.30 mmol) of 5-bromo-7,7-diphenyl-7H-benzo[6,7]indeno[1,2-b]quinoline, 0.24 g (1.1 eq, 1.43 mmol) of naphthalen-2-ylboronic acid, and 0.06 g (0.04 eq, 0.052 mmol) of Tetrakis(triphenylphosphine)palladium(0) were put into a container, vacuum-dried, and then purged with nitrogen gas. After 13 mL of toluene was added into the reaction vessel to dissolve the reactant compounds, 6.5 mL of ethanol and 6.5 mL (10 eq, 13.0 mmol) of a 2.0M aqueous sodium carbonate solution were added thereto and stirred under reflux at about 80° C. for about 3 hours. After termination of the reaction, the reaction product was washed with distilled water, followed by extraction with ethyl acetate to obtain an organic layer. This organic layer was dried using magnesium sulfate, followed by filtration using a Celite and column chromatography to obtain 0.760 g of Compound 8 (5-(naphthalen-2-yl)-7,7-diphenyl-7H-benzo[6,7]indeno[1,2-b]quinoline) (Yield: 75%).

$^1$H NMR: 8.52 (2H), 8.02 (6H), 7.73 (3H), 7.59 (6H), 7.33 (6H), 7.11 (4H).

APCI-MS (m/z): 548[M+]

Example 1

A Corning 15Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting ITO glass substrate was mounted into a vacuum deposition device.

After m-MTDATA was vacuum-deposited on the ITO anode of the ITO glass substrate to form an HIL having a thickness of 600 Å, NPB was deposited on the HIL to form a HTL having a thickness of about 300 Å, and then ADN (host) and Compound FD9 (dopant) were co-deposited in a weight ratio of 95:5 on the HTL to form an EML having a thickness of about 200 Å.

Then, Compound 2 was deposited on the EML to form an ETL having a thickness of about 300 Å, and then LiF was deposited on the ETL to form an EIL having a thickness of about 10 Å. Then, Al was deposited on the EIL to form a cathode having a thickness of about 1000 Å, thereby completing the manufacture of an organic light-emitting device.

<Compound FD9>

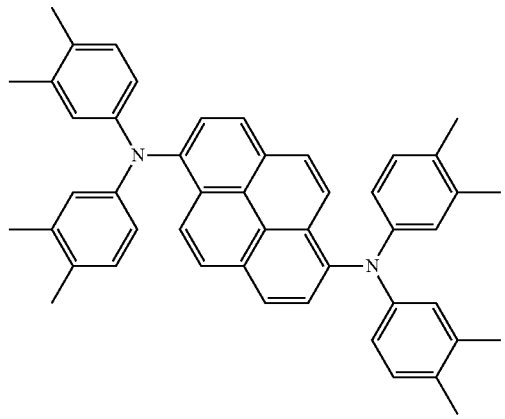

Examples 2 to 5 and Comparative Examples 1 and 2

Organic light-emitting devices were manufactured in the same manner as in Example 1, except that compounds in Table 1, instead of Compound 2, were used to form the ETL.

Evaluation Example 1

Driving voltages, colors, efficiencies, and lifetimes ($T_{95}$) of the organic light-emitting devices of Examples 1 to 5 and Comparative Examples 1 and 2 were evaluated using a Keithley Source-Measure Unit (SMU 236) and a PR650 (Spectroscan) Source Measurement Unit. (available from Photo Research, Inc.). The results are shown in Table 1. The lifetime ($T_{95}$) was measured as the time taken until a measured initial luminance at 1000 nit (assumed as 100%) was reduced to 95% after operation. The efficiencies and lifetimes of the organic light-emitting devices of Examples 1 to 5 and Comparative Example 1 in Table 1 are relative ones with respect to the efficiency and lifetime of the organic light-emitting device of Comparative Example 2.

TABLE 1

| Example No. | Electron transport layer | Color | Efficiency | Lifetime ($T_{95}$) |
|---|---|---|---|---|
| Example 1 | Compound 2 | Blue | 1 | 2.1 |
| Example 2 | Compound 14 | Blue | 1 | 1.0 |
| Example 3 | Compound 26 | Blue | 1.3 | 1.7 |
| Example 4 | Compound 43 | Blue | 1.2 | 1.4 |
| Example 5 | Compound 60 | Blue | 1.35 | 0.85 |
| Comparative Example 1 | Compound A | Blue | 0.9 | 1.1 |
| Comparative Example 2 | Alq$_3$ | Blue | 1 | 1 |

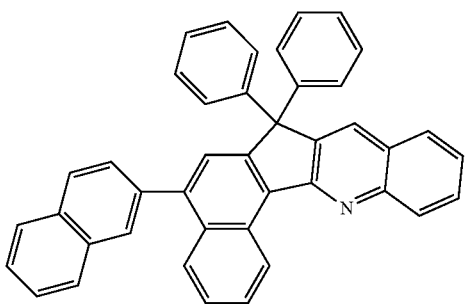

2

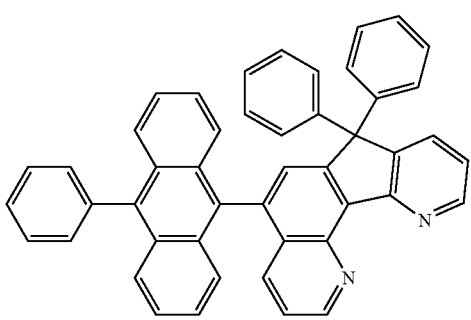

14  15

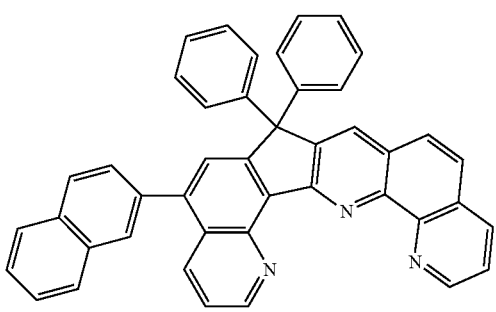

26

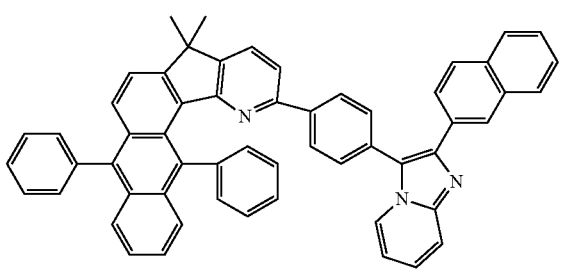

43

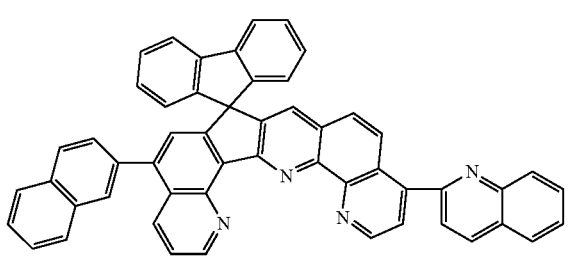

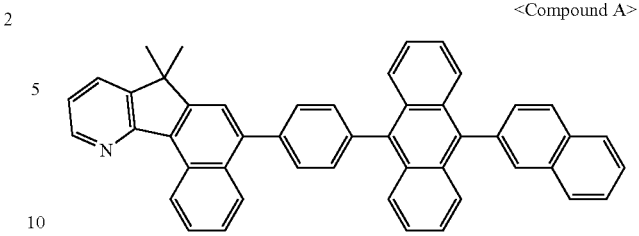

<Compound A>

Referring to Table 1, the organic light-emitting devices of Examples 1 to 5 were found to have improved efficiency and/or lifetime compared to the organic light-emitting device of Comparative Examples 1 and 2.

As described above, according to the one or more of the above embodiments, an organic light-emitting device including a condensed cyclic compound of Formula 1 may have a low driving voltage, a high efficiency, a high luminance, and a long lifetime.

As described above, embodiments are directed to a condensed cyclic compound and an organic light-emitting device including the same.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims.

What is claimed is:

1. A condensed cyclic compound represented by Formula 1:

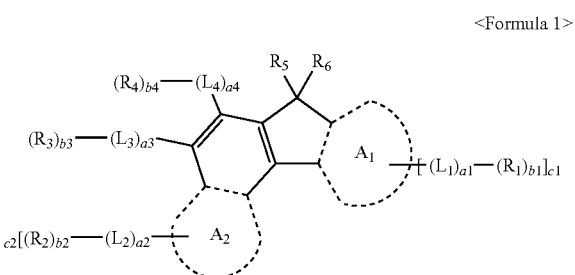

<Formula 1> wherein, in Formula 1, $A_1$ ring is a $C_2$-$C_{20}$ heterocyclic group including at least one N as a ring member atom, and $A_2$ ring is a $C_6$-$C_{20}$ cyclic group, or a $C_2$-$C_{20}$ heterocyclic group including at least one N as a ring member atom, wherein $A_2$ ring is not a benzene when $A_1$ ring is a pyridine, $L_1$ to $L_4$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, a fluoranthenylene group, a triphenylenylene group, a pyrenylene group, a chrysenylene group, a naphthacenylene group, a phenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one of a deuterium, —F, —Cl, —Br, I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C20 alkyl group, a C1-C20 alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a1 to a4 are each independently selected from 0, 1, 2, and 3, $R_1$ to $R_4$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a pentacenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a triazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, a thiadiazolyl group, an imidazopyridinyl group, and an imidazopyrimidinyl group; and Si($Q_3$)($Q_4$)($Q_5$), wherein $Q_3$ to $Q_5$ are each independently selected from a $C_1$-$C_{20}$ alkyl group, a $C_1$-$C_{20}$ alkoxy group, a phenyl group, and a naphthyl group, $R_5$ and $R_6$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), b1 to b4 are each independently an integer selected from 0 to 3, c1 and c2 are each independently an integer selected from 0 to 10, and at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted a divalent non-aromatic condensed polycyclic group, the substituted a divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), or —B($Q_{36}$)($Q_{37}$);

wherein $Q_1$ to $Q_7$, $Q_{11}$ to $Q_{17}$, $Q_{21}$ to $Q_{27}$ and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound as claimed in claim 1, wherein:

the $A_1$ ring is a pyridine, and the $A_2$ ring is a naphthalene, a pyridine, a pyrimidine, a quinoline, an isoquinoline, a benzoquinoline, a quinoxaline, a quinazoline, or a phenanthroline; or the $A_1$ ring is a pyrimidine, a quinoline, an isoquinoline, a benzoquinoline, a quinoxaline, a quinazoline, or a phenanthroline, and the $A_2$ ring is a benzene, a naphthalene, a pyridine, a pyrimidine, a quinoline, an isoquinoline, a benzoquinoline, a quinoxaline, a quinazoline, or a phenanthroline.

3. The condensed cyclic compound as claimed in claim 1, wherein:

the $A_1$ ring is a pyridine, and the $A_2$ ring is a naphthalene or a pyridine; or the $A_1$ ring is a quinoline, a benzoquinoline, or a phenanthroline, and the $A_2$ ring is a benzene, a naphthalene, a pyridine, or a quinoline.

4. The condensed cyclic compound as claimed in claim 1, wherein, $L_1$ to $L_4$ are each independently selected from groups represented by Formulae 3-1 to 3-7 and 3-10 to 3-33:

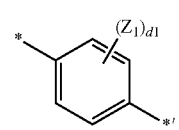

Formula 3-1

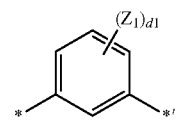

Formula 3-2

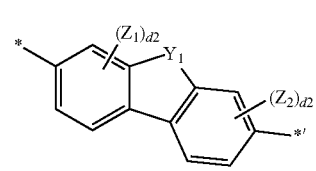

Formula 3-3

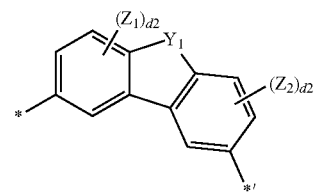

Formula 3-4

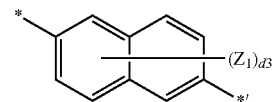

Formula 3-5

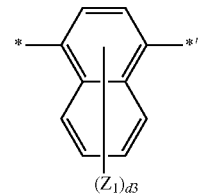

Formula 3-6

129
-continued
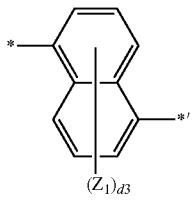
Formula 3-7
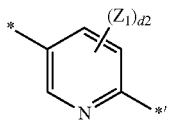
Formula 3-10
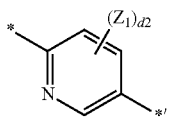
Formula 3-11
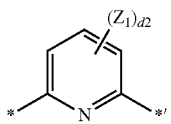
Formula 3-12
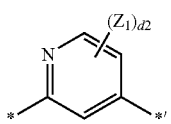
Formula 3-13
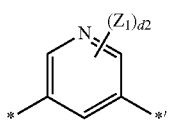
Formula 3-14
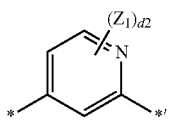
Formula 3-15
Formula 3-16
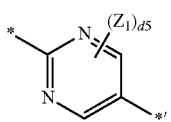
Formula 3-17
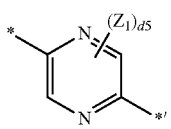
Formula 3-18
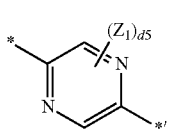
Formula 3-19
130
-continued
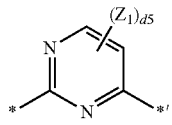
Formula 3-20
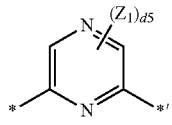
Formula 3-21
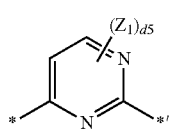
Formula 3-22
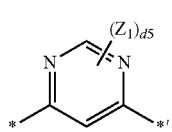
Formula 3-23
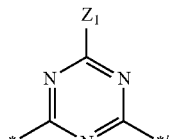
Formula 3-24
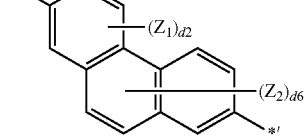
Formula 3-25
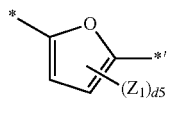
Formula 3-26
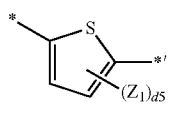
Formula 3-27
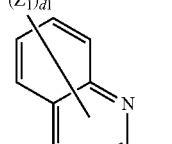
Formula 3-28
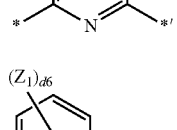
Formula 3-29
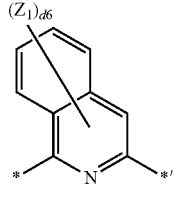

-continued

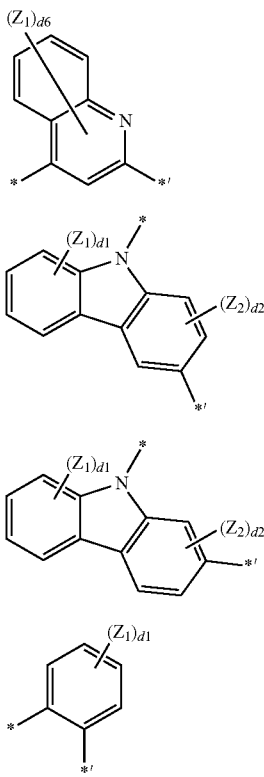

Formula 3-30

Formula 3-31

Formula 3-32

Formula 3-33 wherein, in Formulae 3-1 to 3-7 and 3-10 to 3-33,
$Y_1$ is O, S, $C(Z_3)(Z_4)$, $N(Z_5)$, or $Si(Z_6)(Z_7)$,
$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
d1 is an integer selected from 1 to 4,
d2 is an integer selected from 1 to 3,
d3 is an integer selected from 1 to 6,
d4 is an integer selected from 1 to 8,
d5 is 1 or 2,
d6 is an integer selected from 1 to 5 and
and *' are binding sites with an adjacent atom.

5. The condensed cyclic compound as claimed in claim 1, wherein $L_1$ to $L_4$ are each independently selected from groups represented by Formulae 4-1 to 4-10 and 4-12 to 4-24:

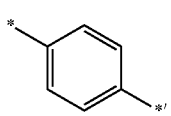

Formula 4-1

-continued

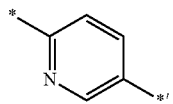

Formula 4-2

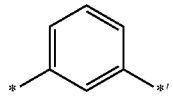

Formula 4-3

Formula 4-4

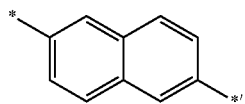

Formula 4-5

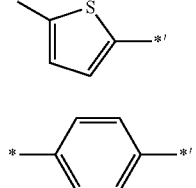

Formula 4-6

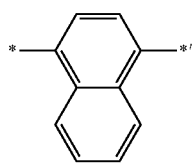

Formula 4-7

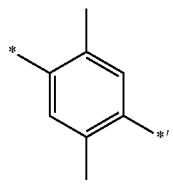

Formula 4-8

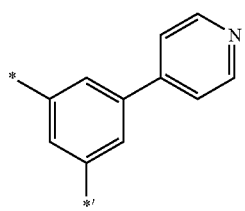

Formula 4-9

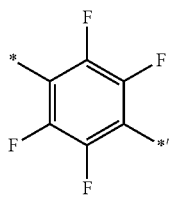

Formula 4-10

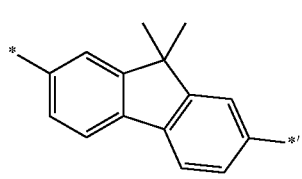

Formula 4-12

-continued

Formula 4-13
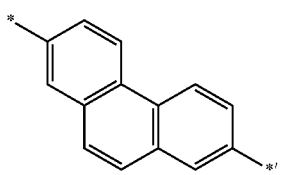

Formula 4-14
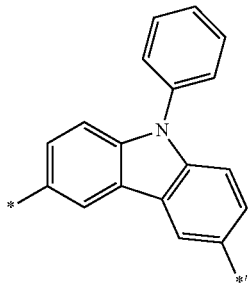

Formula 4-15
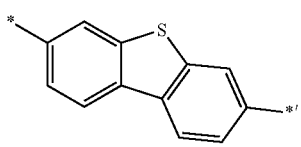

Formula 4-16
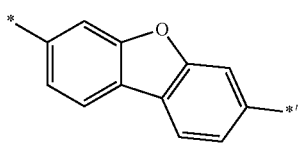

Formula 4-17
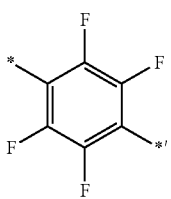

Formula 4-18
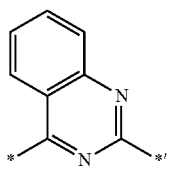

Formula 4-19
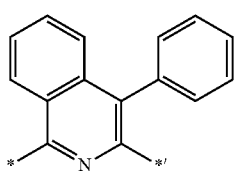

Formula 4-20
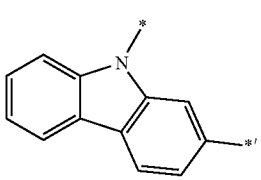

Formula 4-21
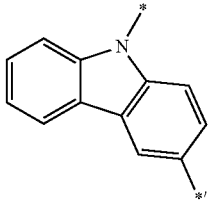

Formula 4-22
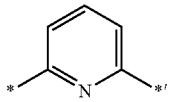

Formula 4-23
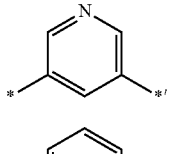

Formula 4-24 wherein, in Formulae 4-1 to 4-10 and 4-12 to 4-24, * and *' are binding sites with an adjacent atom.

6. The condensed cyclic compound as claimed in claim 1, wherein a1 to a4 are each independently 0 or 1.

7. The condensed cyclic compound as claimed in claim 1, wherein:

$R_5$ and $R_6$ are each independently selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

8. The condensed cyclic compound as claimed in claim 1, wherein:

$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group and an imidazopyrimidinyl group; and a phenyl group, a naphthyl group, a fluorenyl group, a spiro-fluorenyl group, a benzofluorenyl group, a dibenzofluorenyl group, a phenanthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

9. The condensed cyclic compound as claimed in claim 1, wherein $R_5$ and $R_6$ are each independently selected from a $C_1$-$C_{20}$ alkyl group and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group.

10. The condensed cyclic compound as claimed in claim 1, wherein:

$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by Formulae 6-1 to 6-5, 6-8 to 6-13, and 6-16 to 6-62, and $R_5$ and $R_6$ are each independently selected from a $C_1$-$C_{20}$ alkyl group, a $C_1$-$C_{20}$ alkoxy group, and groups represented by Formulae 6-1 to 6-62:

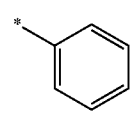

Formula 6-1

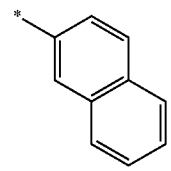

Formula 6-2

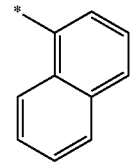

Formula 6-3

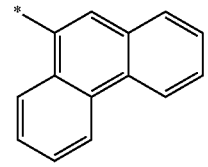

Formula 6-4

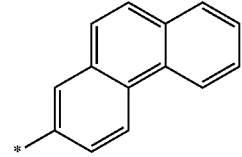

Formula 6-5

Formula 6-6

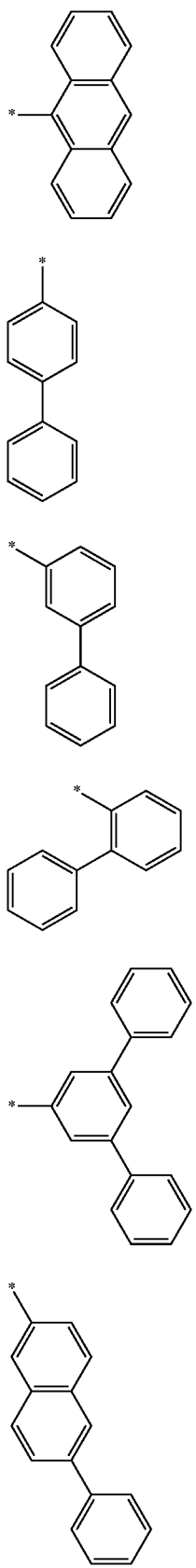
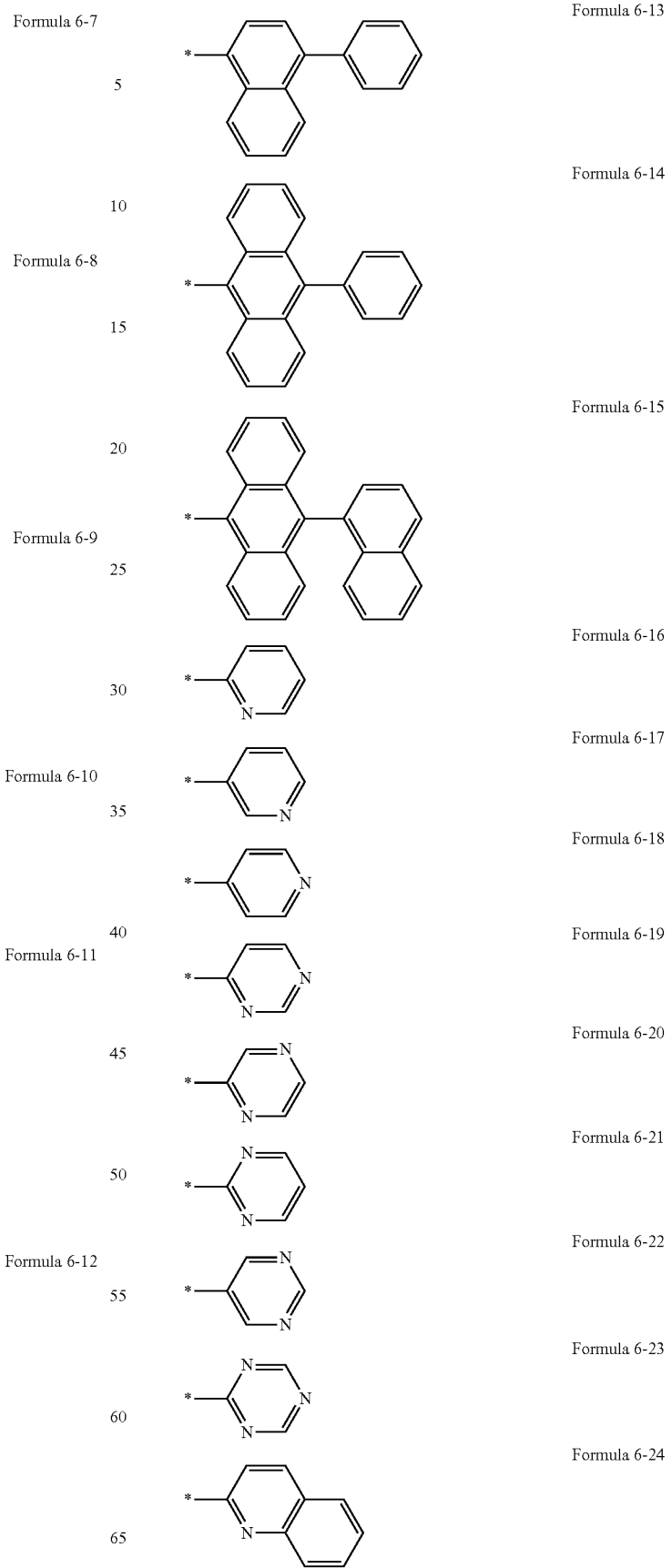

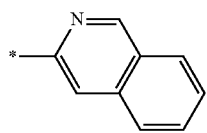
Formula 6-25
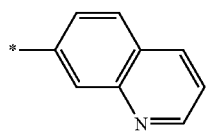
Formula 6-26
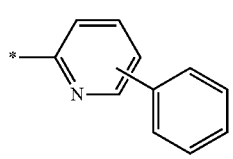
Formula 6-27
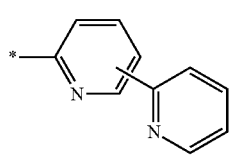
Formula 6-28
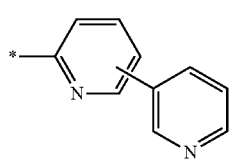
Formula 6-29
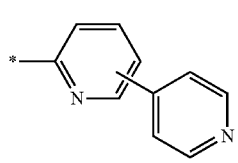
Formula 6-30
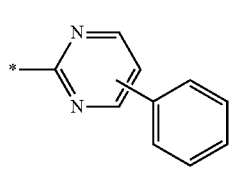
Formula 6-31
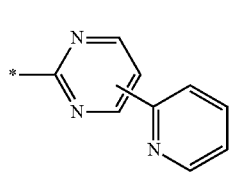
Formula 6-32
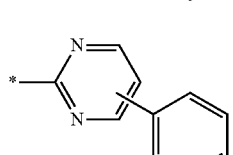
Formula 6-33
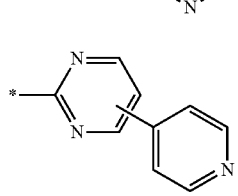
Formula 6-34
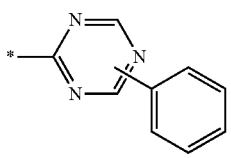
Formula 6-35
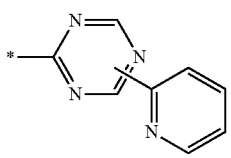
Formula 6-36
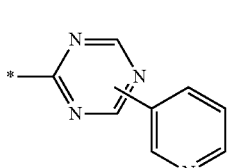
Formula 6-37
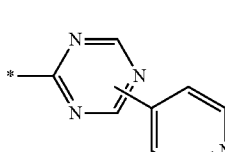
Formula 6-38
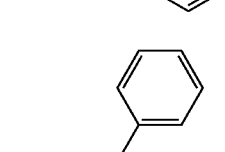
Formula 6-39
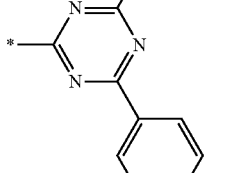
Formula 6-40
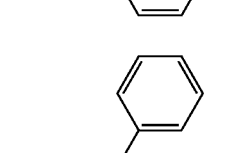
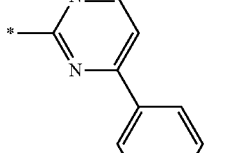
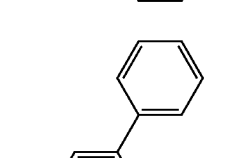
Formula 6-41
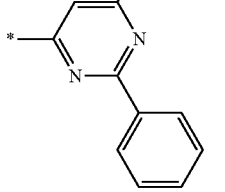

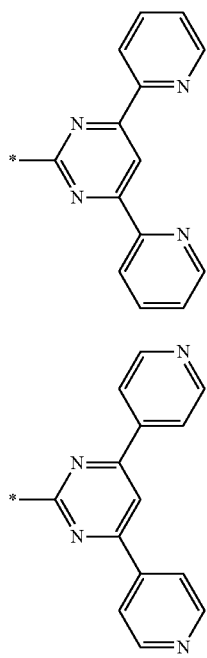 Formula 6-42
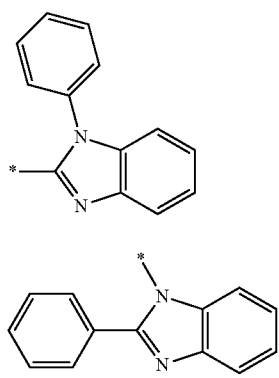 Formula 6-43
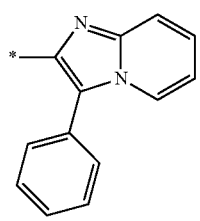 Formula 6-44
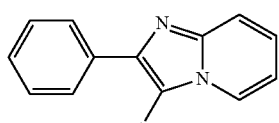 Formula 6-45
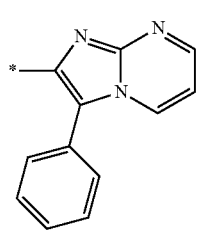 Formula 6-46
Formula 6-47
Formula 6-48
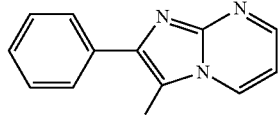 Formula 6-49
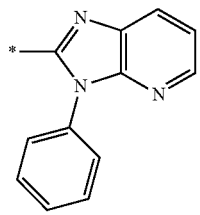 Formula 6-51
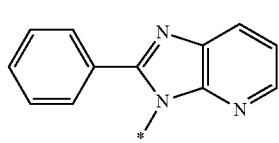 Formula 6-52
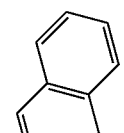 Formula 6-53
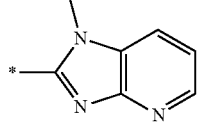 Formula 6-54
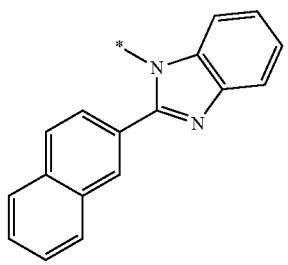 Formula 6-55
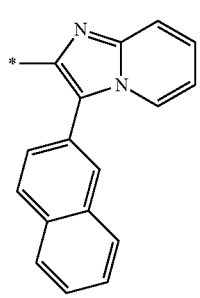

Formula 6-56

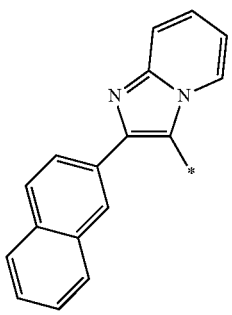

Formula 6-57

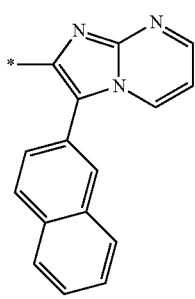

Formula 6-58

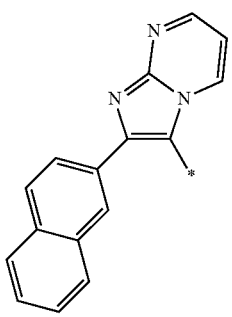

Formula 6-59

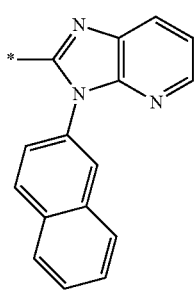

Formula 6-60

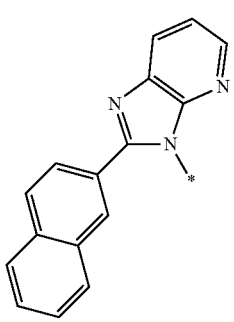

Formula 6-61

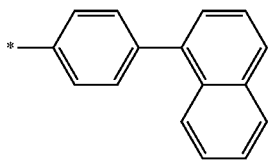

Formula 6-62

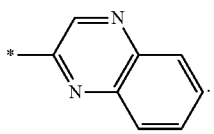

11. The condensed cyclic compound as claimed in claim 1, wherein:

$R_5$ and $R_6$ are each independently selected from a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, and $R_5$ and $R_6$ are linked to each other via a single bond or a substituted or unsubstituted $C_1$-$C_5$ alkylene group.

12. The condensed cyclic compound as claimed in claim 1, wherein the condensed cyclic compound of Formula 1 is represented by Formula 1A or 1B:

<Formula 1A>

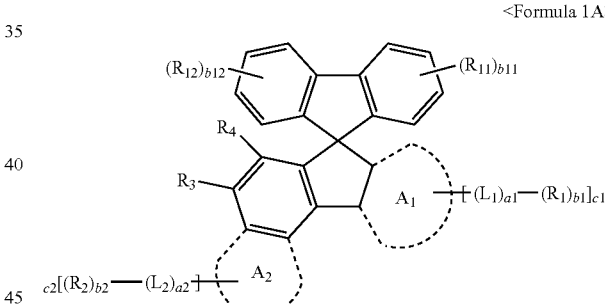

<Formula 1B>

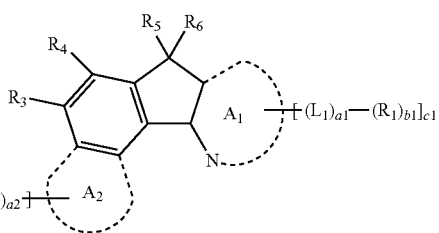

wherein, in Formulae 1A and 1B, $A_1$ ring, $A_2$ ring, $L_1$, $L_2$, a1, a2, $R_1$ to $R_6$, b1, b2, c1, and c2 are defined the same as those in claim 1; $R_{11}$ and $R_{12}$ are each independently defined the same as $R_1$ in claim 1; and b11 and b12 are each independently an integer selected from 1 to 4.

13. The condensed cyclic compound as claimed in claim 1, wherein the condensed cyclic compound of Formula 1 is represented by one of Formulae 1(1) to 1(13) and Formulae 1A(1) to 1A(13):

Formula 1(1)
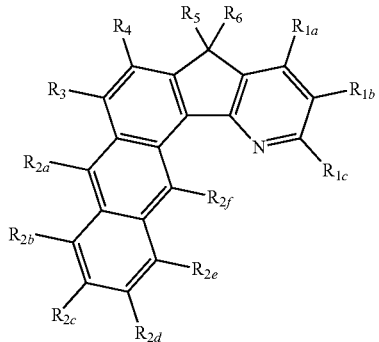
Formula 1(2)
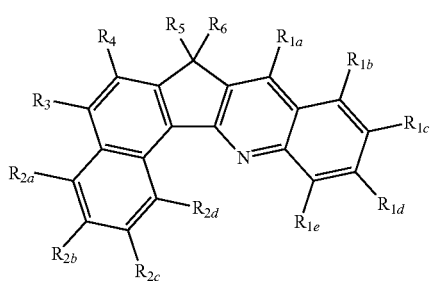
Formula 1(3)
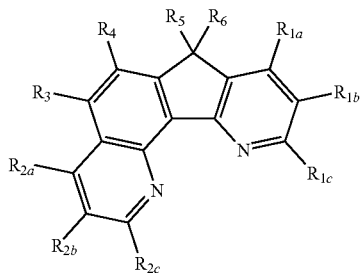
Formula 1(4)
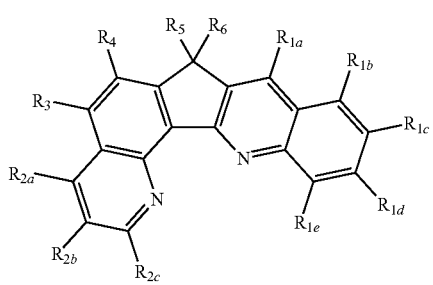
Formula 1(5)
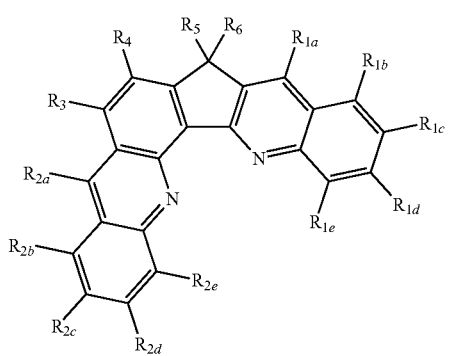
Formula 1(6)
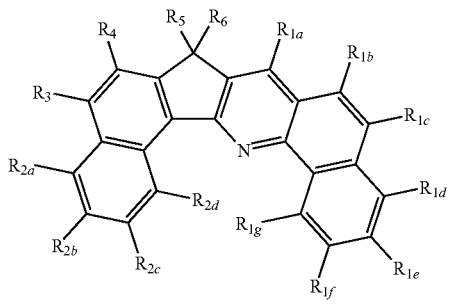
Formula 1(7)
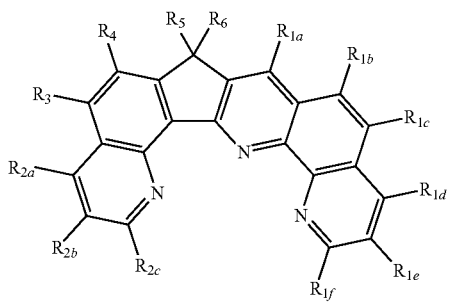
Formula 1(8)
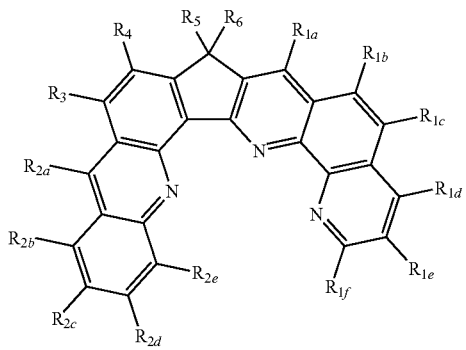
Formula 1(9)
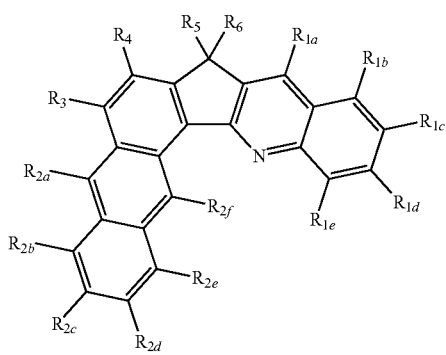

Formula 1(10)
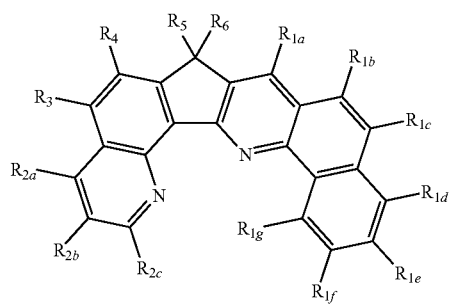
Formula 1A(1)
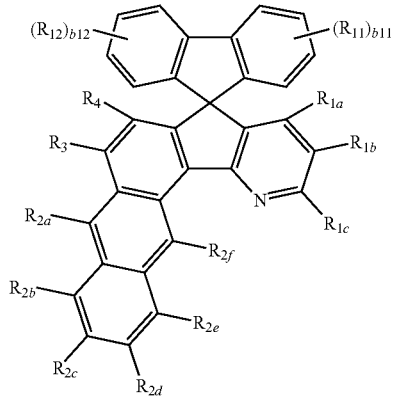
Formula 1(11)
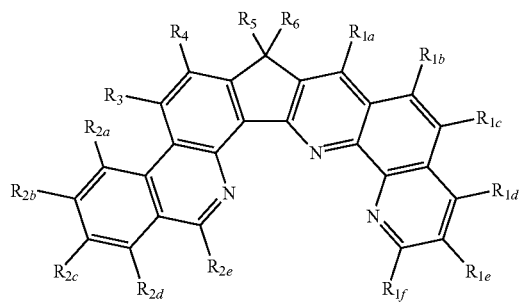
Formula 1A(2)
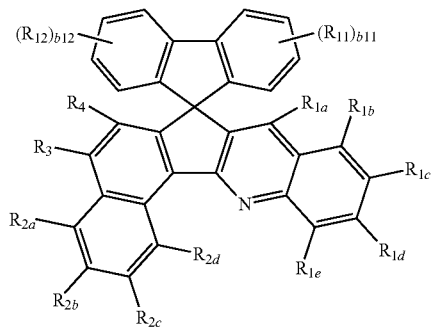
Formula 1(12)
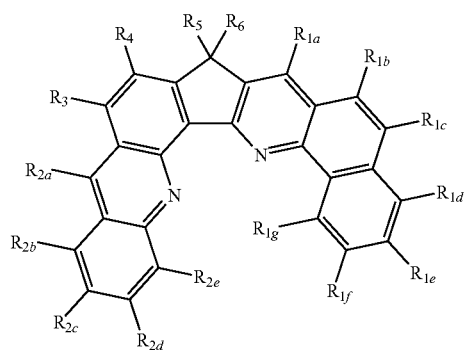
Formula 1A(3)
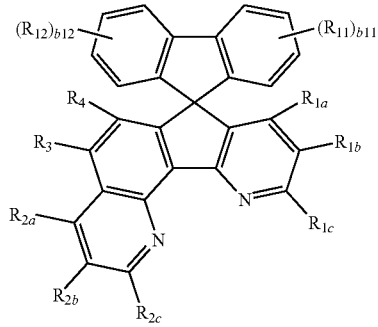
Formula 1(13)
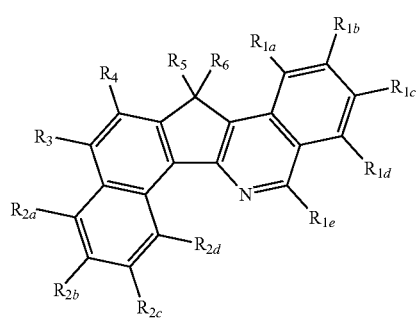
Formula 1A(4)
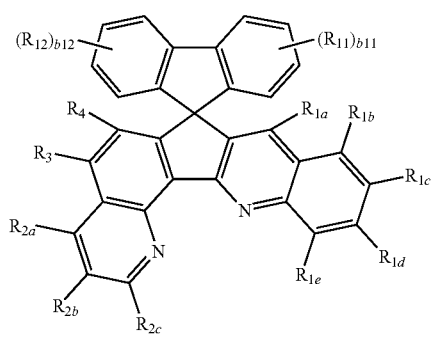

-continued
Formula 1A(5)
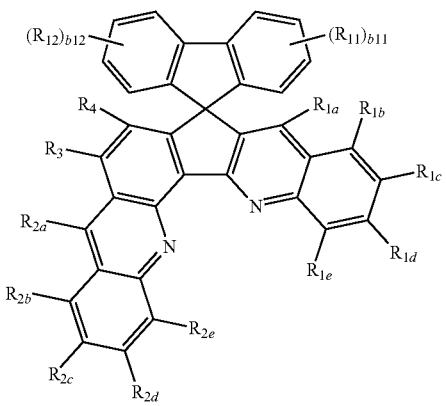
Formula 1A(6)
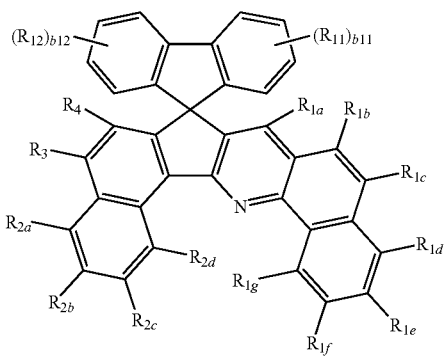
Formula 1A(7)
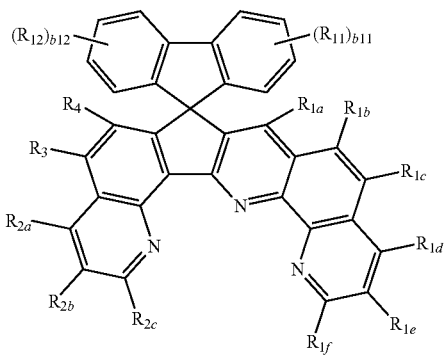
Formula 1A(8)
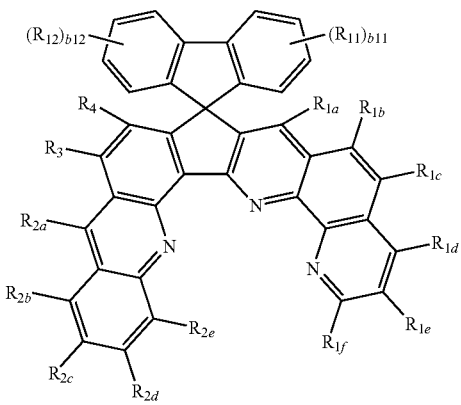
Formula 1A(9)
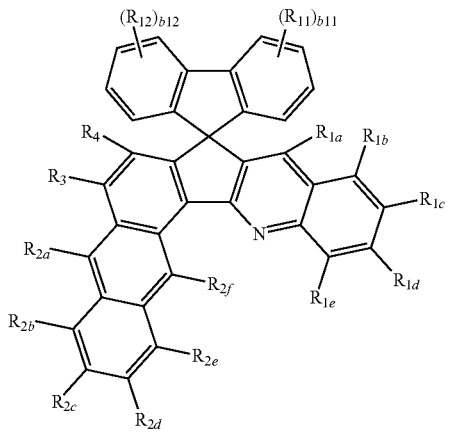
Formula 1A(10)
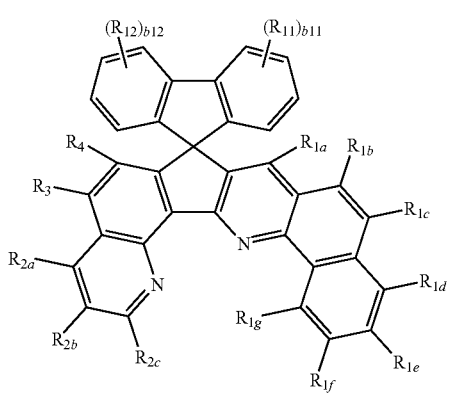
Formula 1A(11)
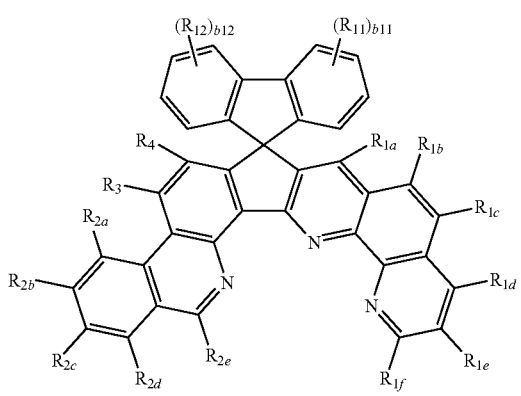

-continued

Formula 1A(12)

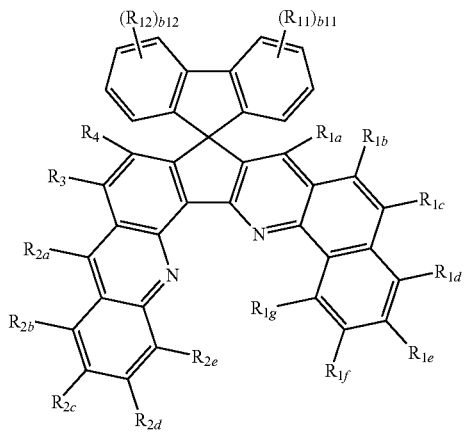

Formula 1A(13)

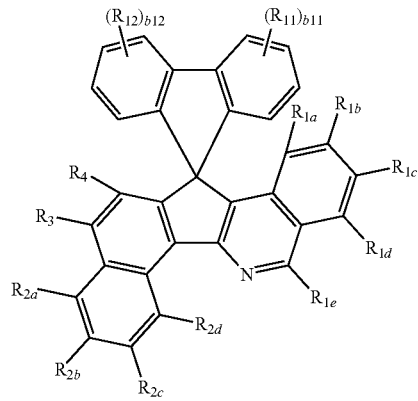

wherein, in Formulae 1(1) to 1(13) and Formula 1A(1) to 1A(13), $R_3$ and $R_4$ are defined the same as those in claim 1, $R_{1a}$ to $R_{1g}$, $R_{11}$, and $R_{12}$ are each independently defined the same as $R_1$ in claim 1, and $R_{2a}$ to $R_{2f}$ are each independently defined the same as $R_2$ in claim 1.

14. The condensed cyclic compound as claimed in claim 1, wherein the condensed cyclic compound is one of Compounds 1 to 12 and 16 to 66:

1

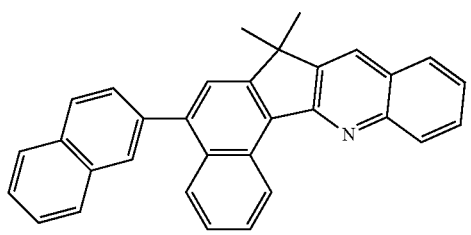

2

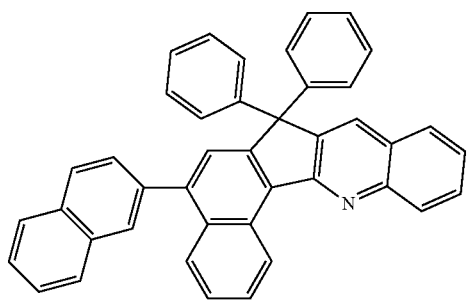

3

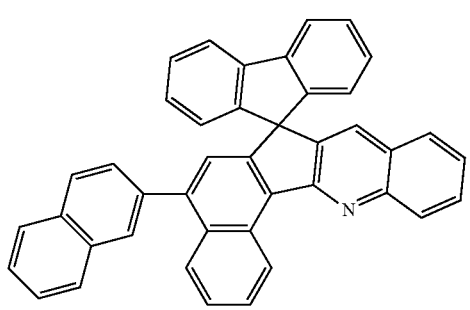

4

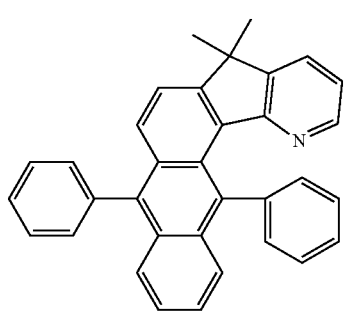

5
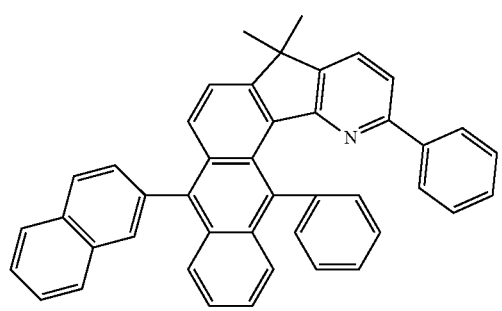
6
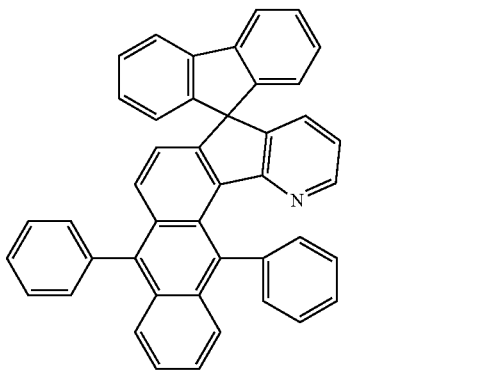
7
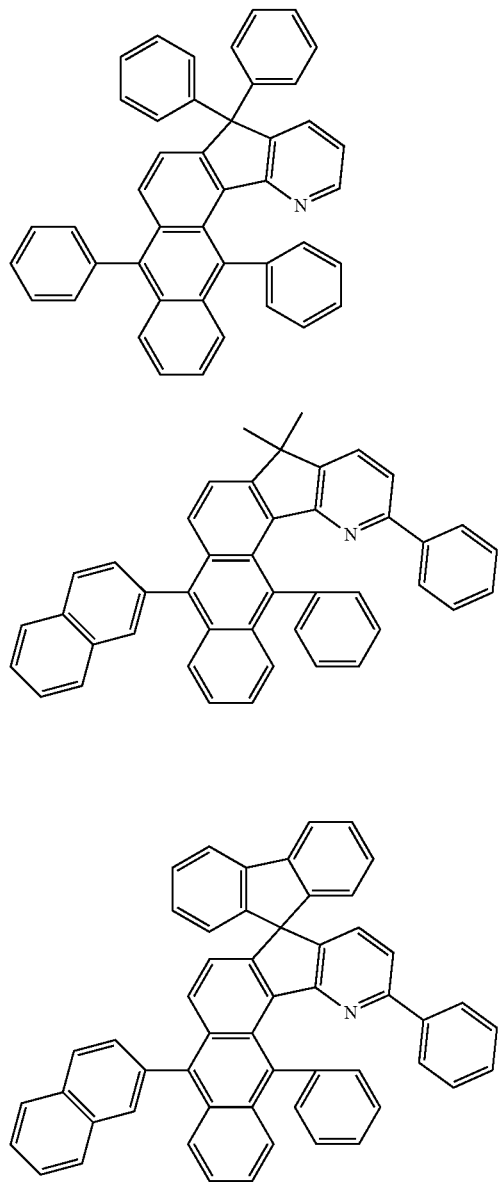
8
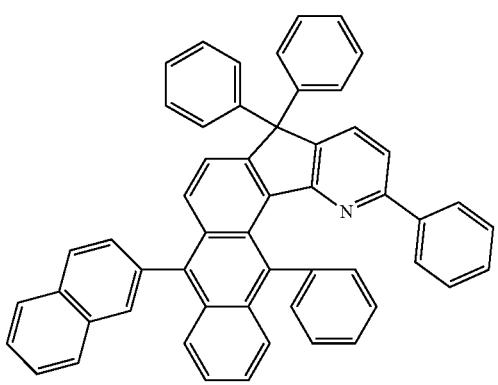
9
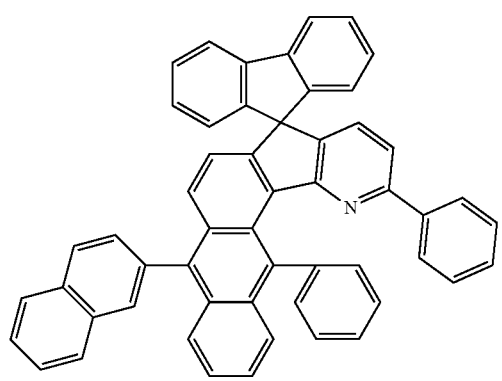
10
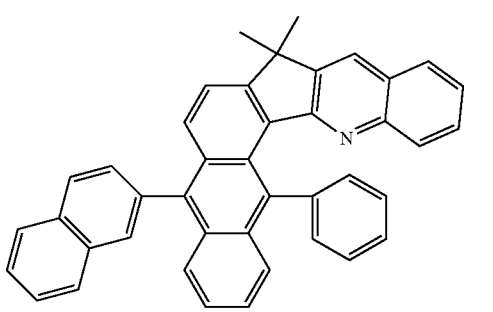
11
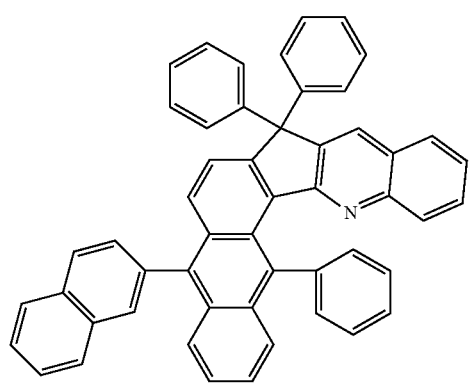
12
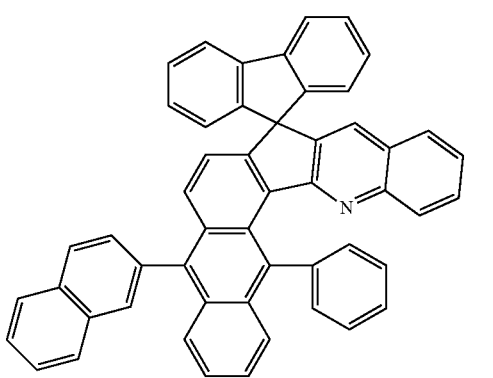

-continued
13
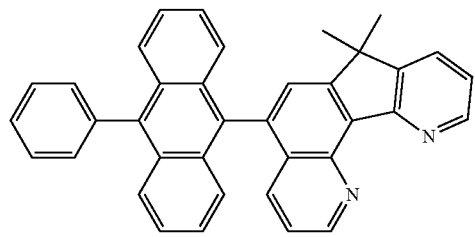
14
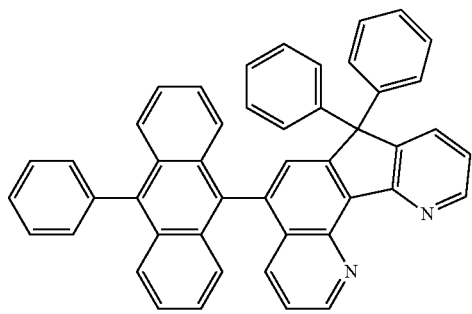
15
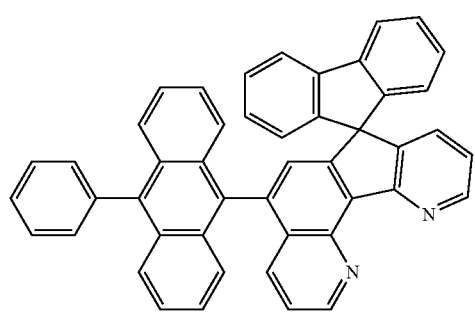
16
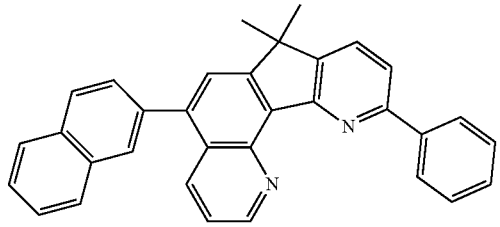
17
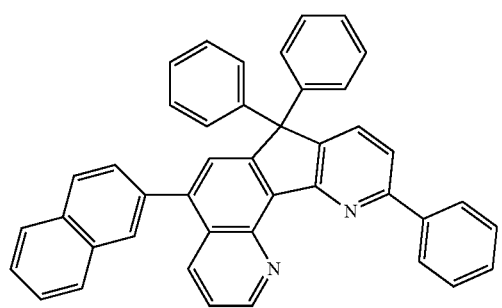
18
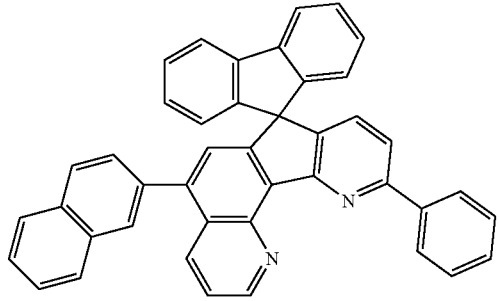
19
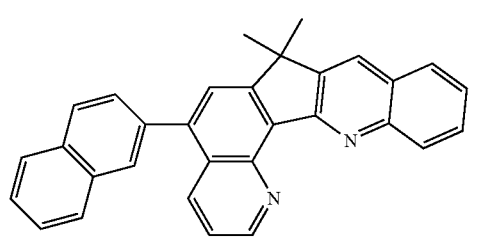
20
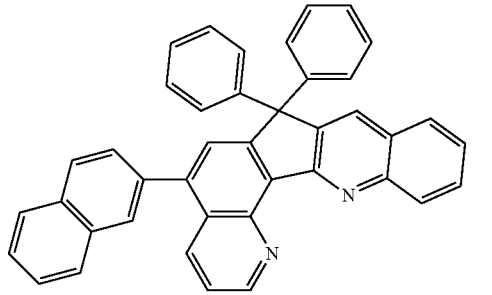
21
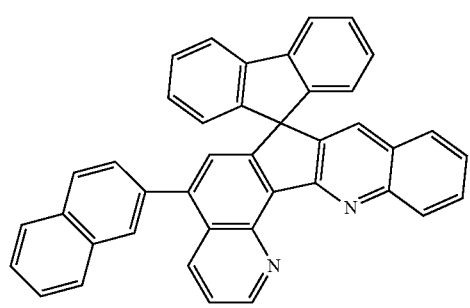
22
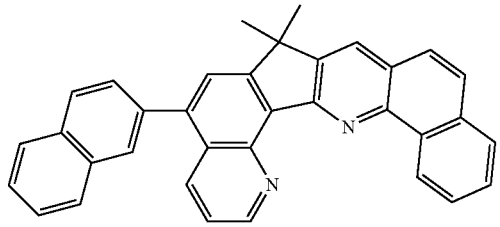

-continued
23
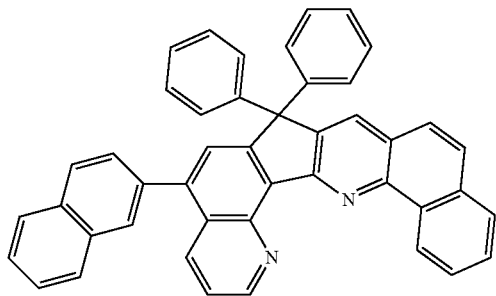
24
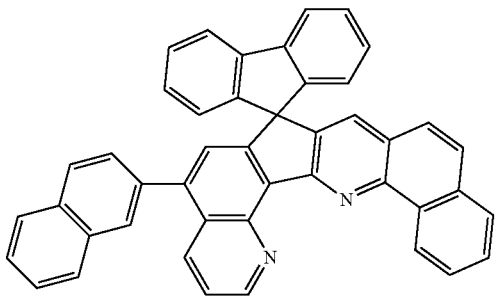
25
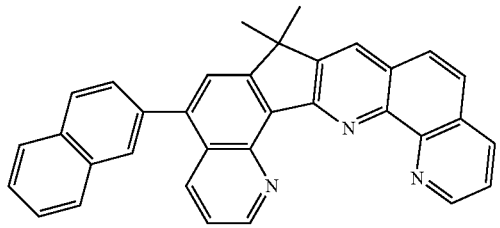
26
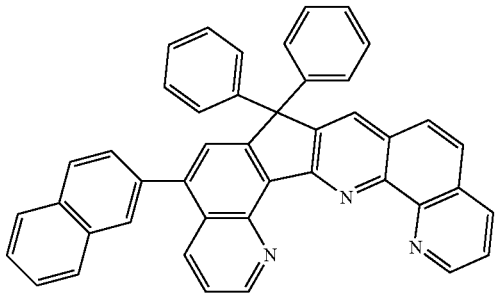
27
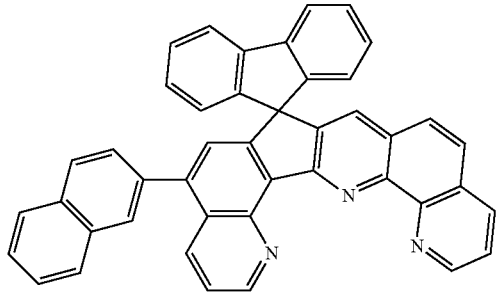
28
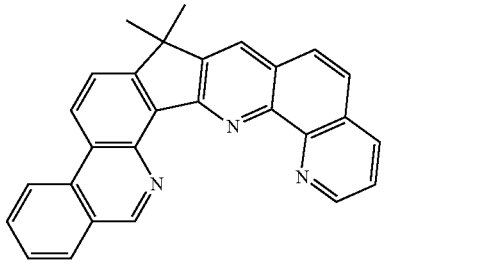
29
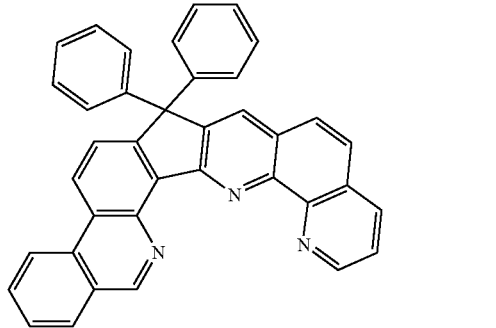
30
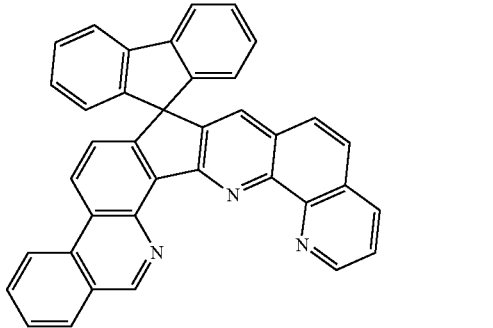
31
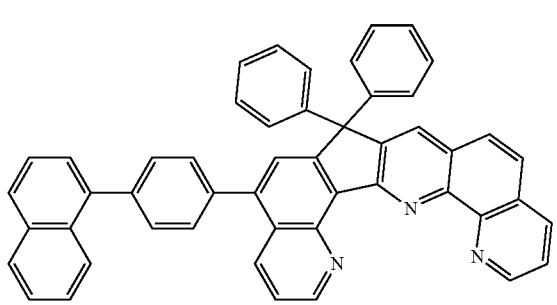
32
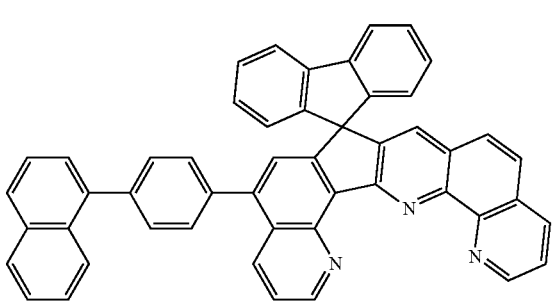

-continued
33
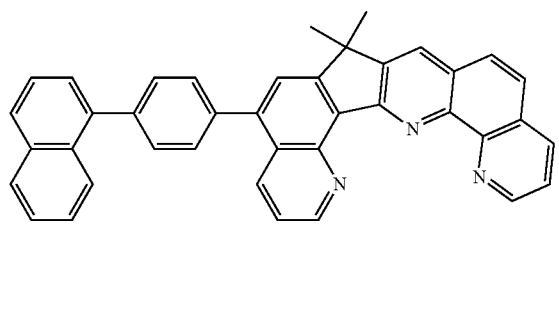
34
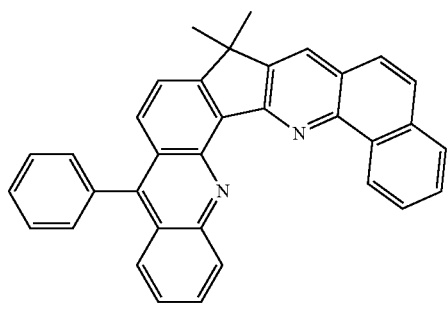
35
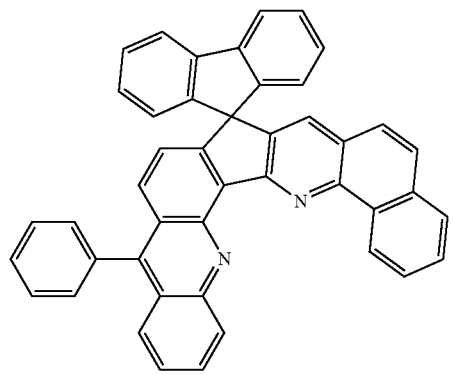
36
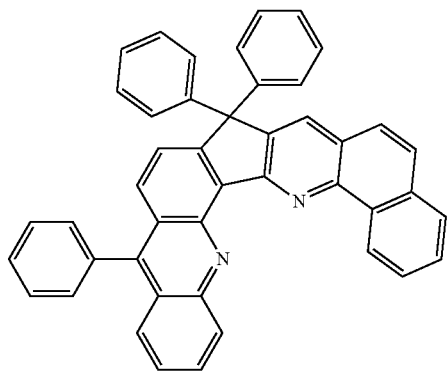
37
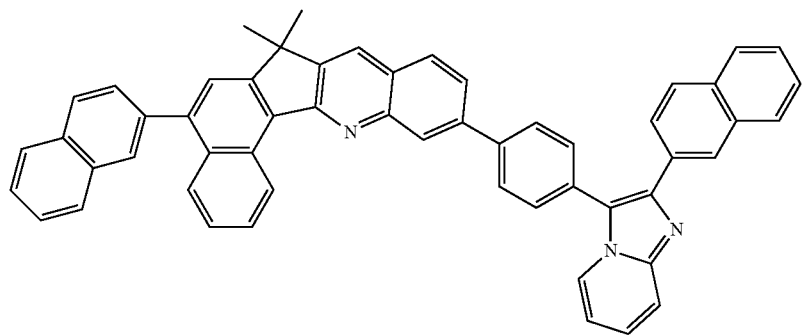
38
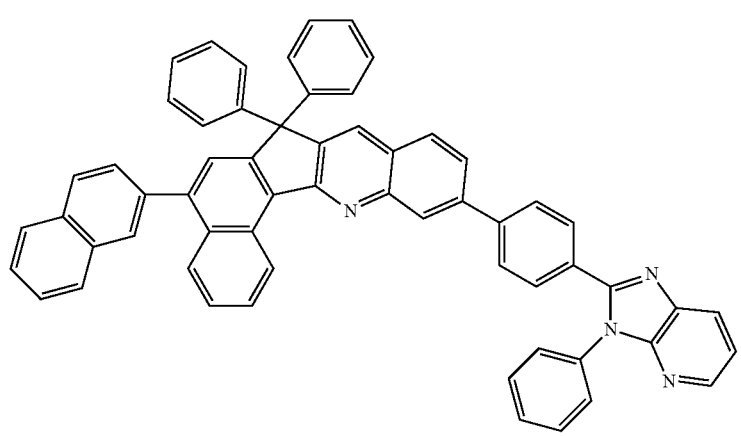

39
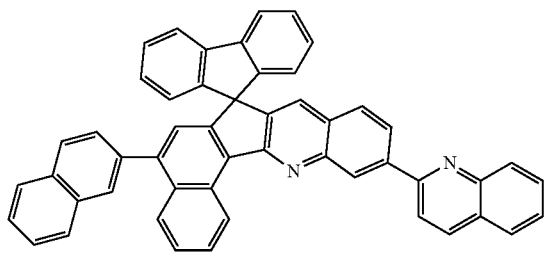
40
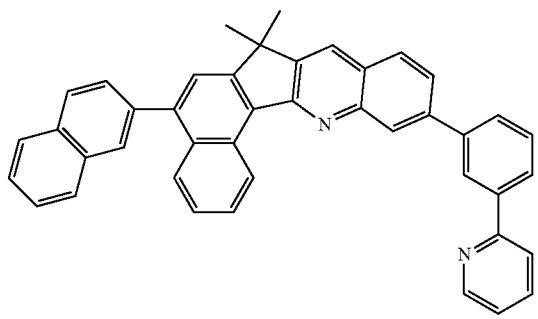
41
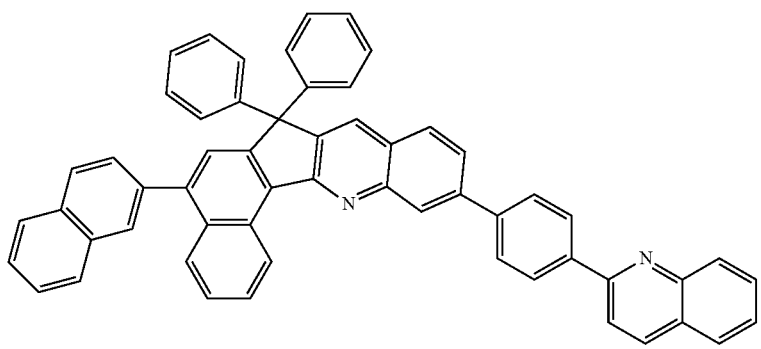
42
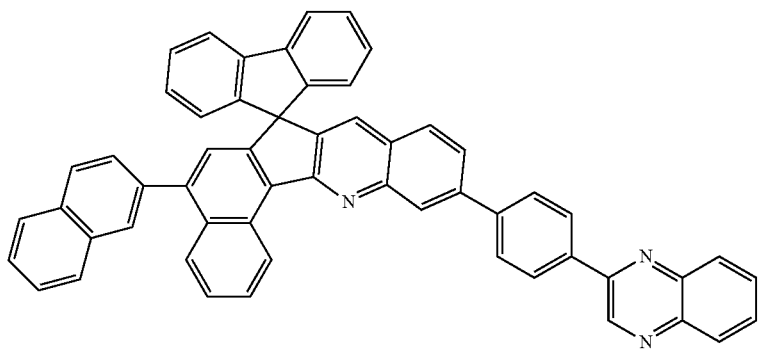
43
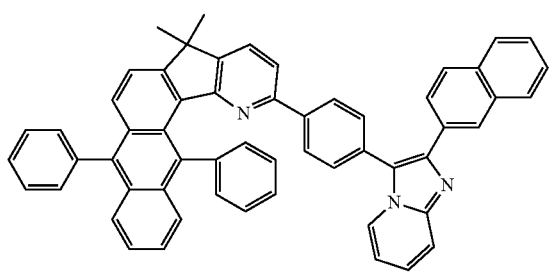
44
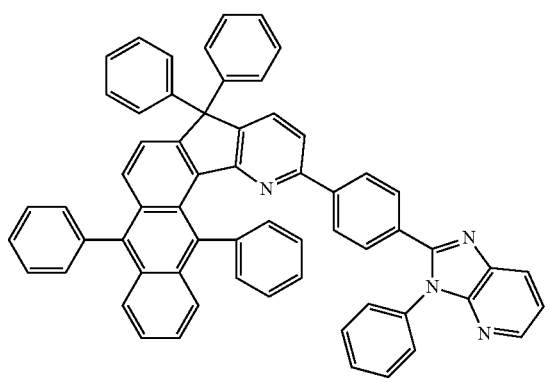

-continued
45
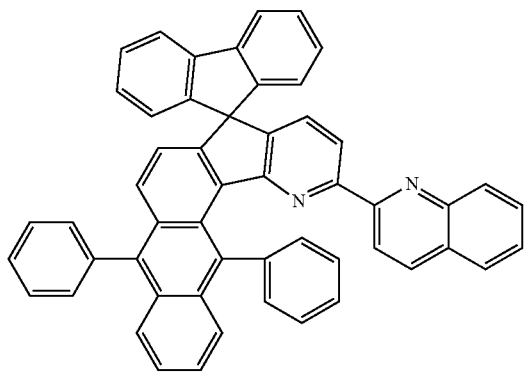
46
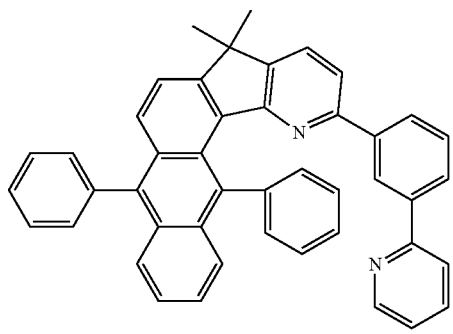
47
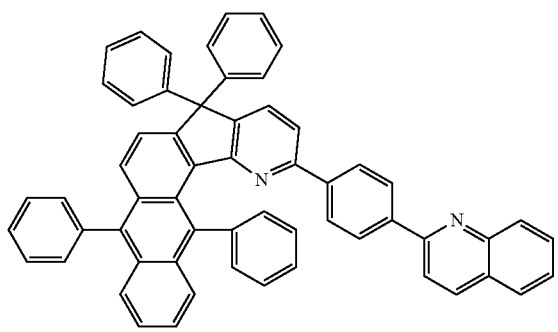
48
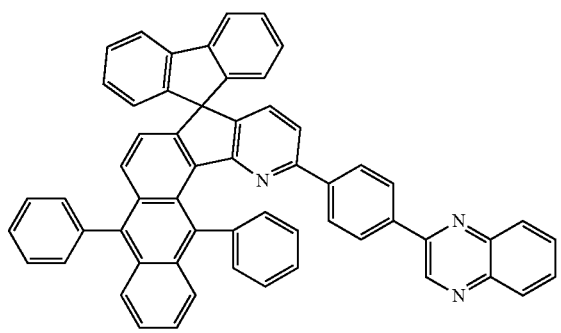
49
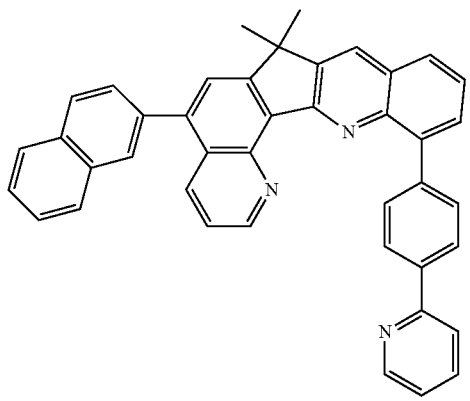
50
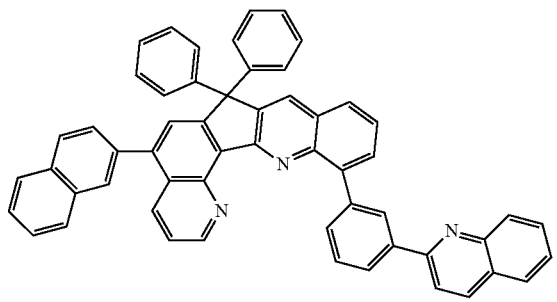
51
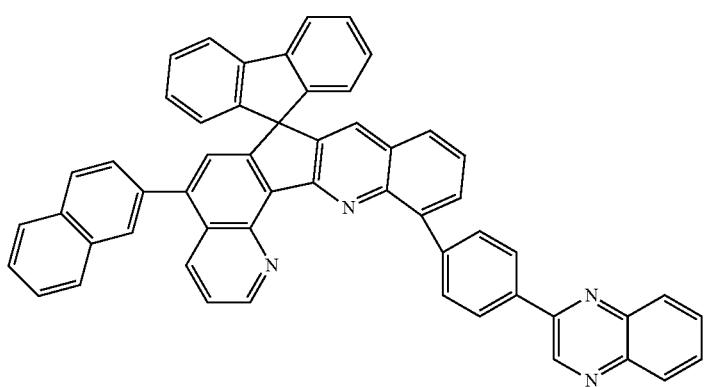

-continued
52
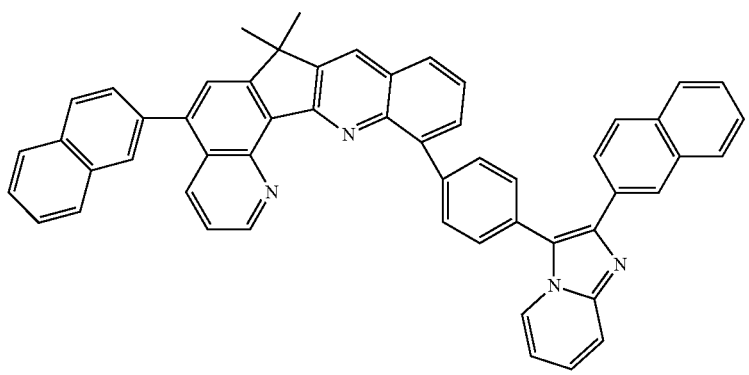
53
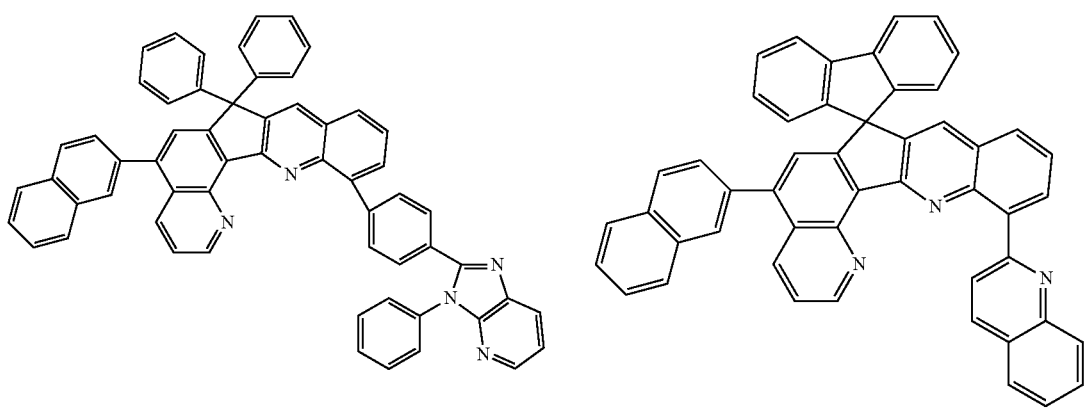
54
55
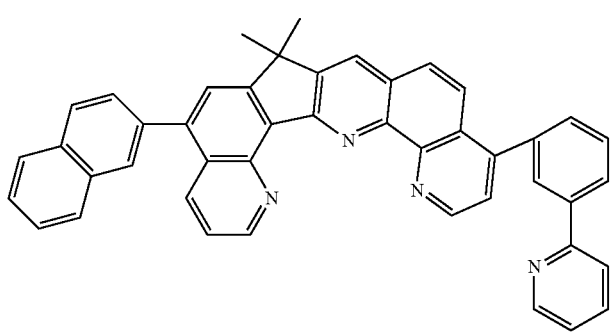
56
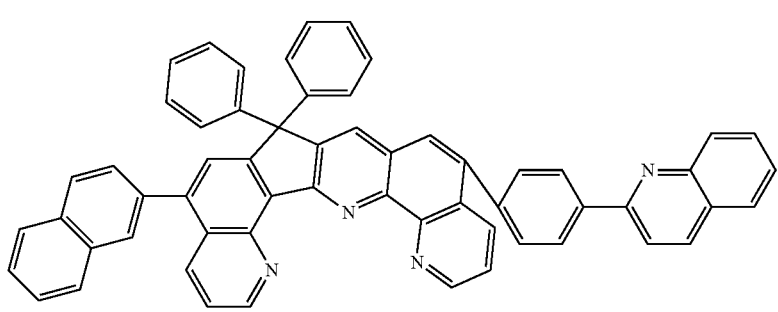

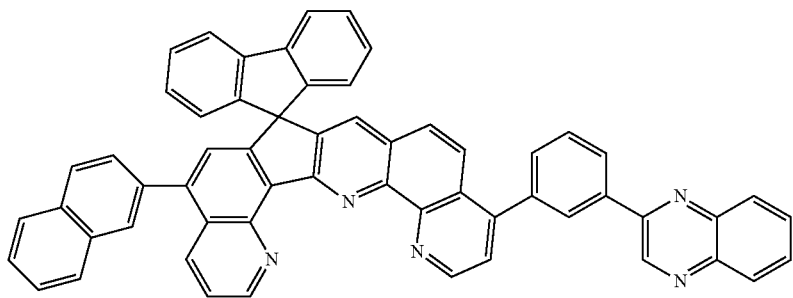
57
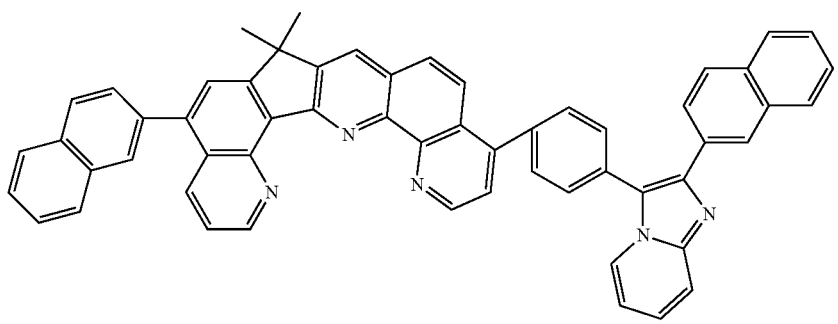
58
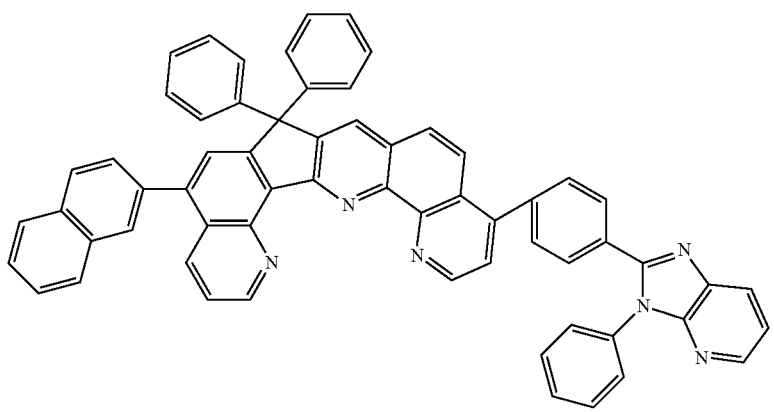
59
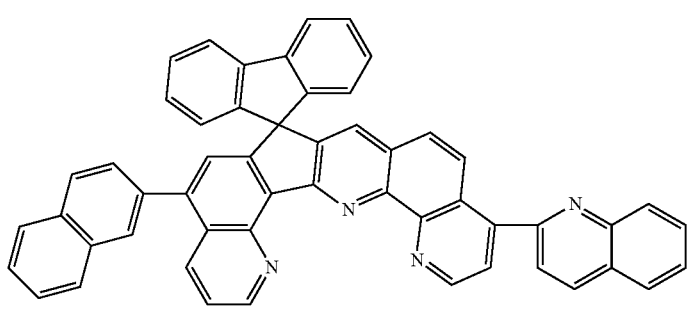
60

61
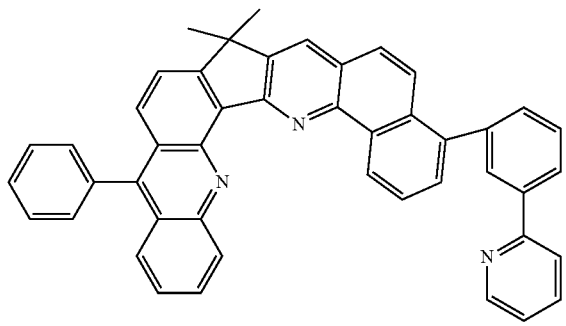
62
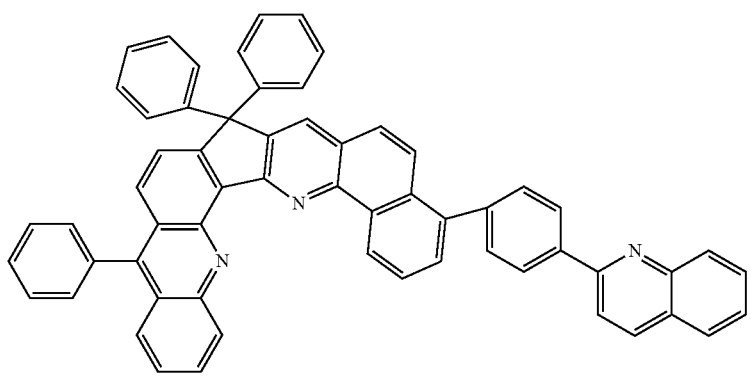
63
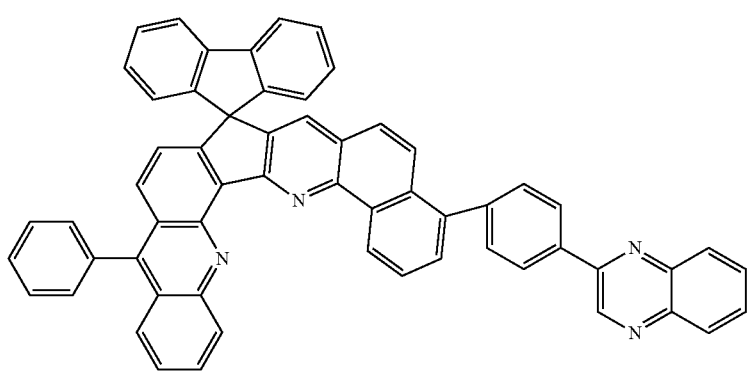
64
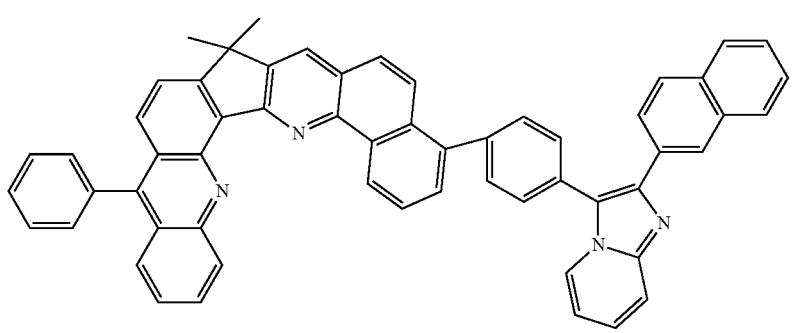

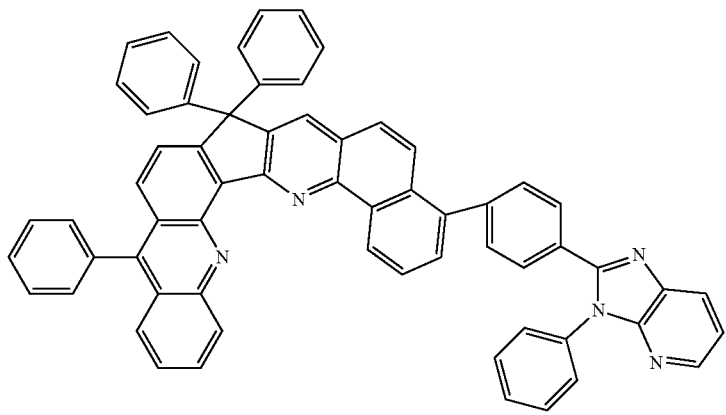

65

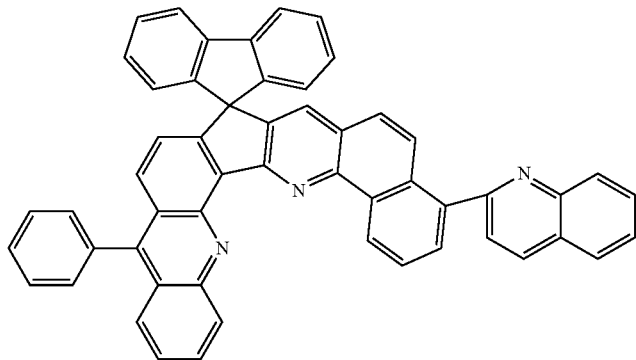

66

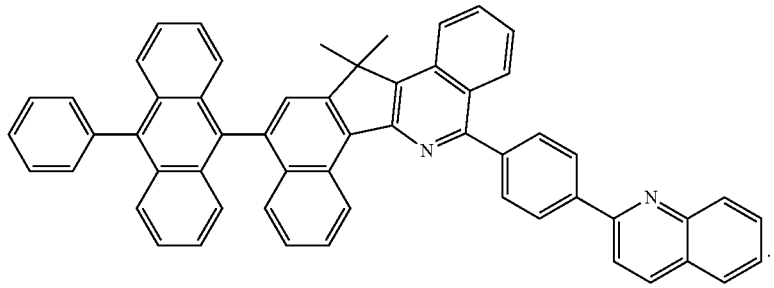

67

15. An organic light-emitting device, comprising:
a first electrode;
a second electrode disposed opposite to the first electrode; and
an organic layer disposed between the first electrode and the second electrode and comprising an emission layer, wherein the organic layer comprises at least one condensed cyclic compound as claimed in claim 1.

16. The organic light-emitting device as claimed in claim 15, wherein:
the first electrode is an anode,
the second electrode is a cathode, and
the organic layer includes:
i) a hole transport region disposed between the first electrode and the emission layer and including at least one of a hole injection layer, a hole transport layer, a buffer layer, and an electron blocking layer, and
ii) an electron transport region disposed between the emission layer and the second electrode and including at least one of a hole blocking layer, an electron transport layer, and an electron injection layer.

17. The organic light-emitting device as claimed in claim 16, wherein the electron transport region includes the at least one condensed cyclic compound.

18. The organic light-emitting device as claimed in claim 16, wherein the hole transport region includes at least one of a compound represented by Formula 201A and a compound represented by Formula 202A:

<Formula 201A>

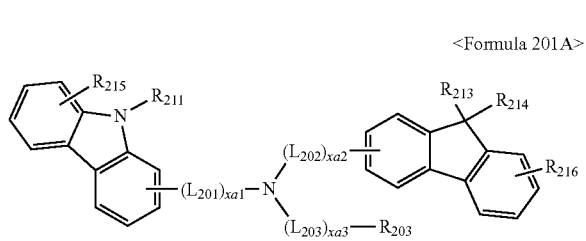

-continued

<Formula 202A>

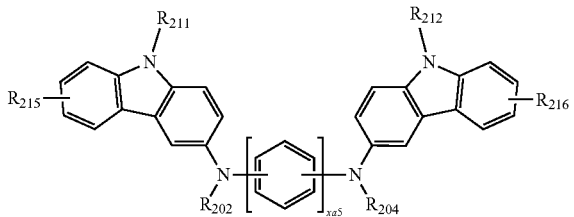

wherein, in Formulae 201A and 202A, $L_{201}$ to $L_{203}$ are each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xa1 to xa3 are each independently 0 or 1;

$R_{202}$ to $R_{204}$, $R_{211}$, and $R_{212}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group or a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{213}$ and $R_{214}$ are each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a carbazolyl group, and a triazinyl group, $R_{215}$ and $R_{216}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xa5 is 1 or 2.

* * * * *